US 8,167,789 B2

(12) United States Patent
Sato et al.

(10) Patent No.: US 8,167,789 B2
(45) Date of Patent: May 1, 2012

(54) IMAGE PROCESSING SYSTEM AND METHOD FOR BODY-INSERTABLE APPARATUS

(75) Inventors: Ryoji Sato, Fuchu (JP); Hironobu Takizawa, Hino (JP); Yasuharu Oda, Fuchu (JP); Katsuyoshi Taniguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 35 days.

(21) Appl. No.: 12/879,402

(22) Filed: Sep. 10, 2010

(65) Prior Publication Data
US 2011/0196201 A1   Aug. 11, 2011

Related U.S. Application Data

(63) Continuation of application No. PCT/JP2010/050556, filed on Jan. 19, 2010.

(30) Foreign Application Priority Data

Mar. 11, 2009  (JP) ................................ 2009-058657

(51) Int. Cl.
*A61B 1/00* (2006.01)
(52) U.S. Cl. .......................... 600/109; 600/117; 600/118
(58) Field of Classification Search .................. 600/101, 600/117, 118, 109, 424; 382/128
See application file for complete search history.

(56) References Cited

U.S. PATENT DOCUMENTS

| 7,122,001 | B2 * | 10/2006 | Uchiyama et al. | 600/103 |
| 7,636,092 | B2 * | 12/2009 | Horn et al. | 345/440 |
| 7,805,178 | B1 * | 9/2010 | Gat | 600/407 |
| 2004/0225223 | A1 * | 11/2004 | Honda et al. | 600/476 |
| 2004/0249291 | A1 * | 12/2004 | Honda et al. | 600/476 |
| 2005/0123179 | A1 * | 6/2005 | Chen et al. | 382/128 |
| 2006/0202998 | A1 | 9/2006 | Hirakawa et al. | |
| 2007/0161858 | A1 | 7/2007 | Homan et al. | |
| 2008/0086028 | A1 * | 4/2008 | Matsui | 600/109 |
| 2008/0172255 | A1 * | 7/2008 | Hirakawa et al. | 705/3 |

(Continued)

FOREIGN PATENT DOCUMENTS

JP    HEI11-104072    4/1999
(Continued)

OTHER PUBLICATIONS

English language abstract only of JP 10-020214.
(Continued)

*Primary Examiner* — John P Leubecker
(74) *Attorney, Agent, or Firm* — Scully, Scott, Murphy & Presser, P.C.

(57) ABSTRACT

An image processing system includes an orientation specifying unit that specifies orientation of the body-insertable apparatus at the time of capturing the image data with respect to a reference direction, a rotation correcting unit that performs rotation correction on image data based on the specified orientation, a screen generating unit that generates a screen displaying the image data, an average color bar generating unit that calculates an average color of the image data, generates an image of the calculated average color, and generates an average color bar in which images of the generated average colors are connected in accordance with order of the image data, and an organ image generating unit that generates an organ image obtained by superimposing the images of the average colors generated by the average color bar generating unit. The screen generating incorporates the average color bar and the organ image into the screen.

17 Claims, 63 Drawing Sheets

U.S. PATENT DOCUMENTS

2008/0292150 A1* 11/2008 Hirakawa .................. 382/128

FOREIGN PATENT DOCUMENTS

| | | |
|---|---|---|
| JP | 2001-17388 A | 1/2001 |
| JP | 2003-070728 | 3/2003 |
| JP | 2004-154176 | 6/2004 |
| JP | 2004-321603 A | 11/2004 |
| JP | 2005-168524 A | 6/2005 |
| JP | 2006-280792 | 10/2006 |
| JP | 2007-000608 | 1/2007 |
| JP | 3898781 B2 | 1/2007 |
| JP | 2007-075157 | 3/2007 |
| JP | 2008-043466 | 2/2008 |
| WO | WO 2007/023771 A1 | 3/2007 |
| WO | WO 2008/059773 A1 | 5/2008 |

OTHER PUBLICATIONS

English language abstract only of EP 2 090 215 A1.
International Search Report dated Apr. 20, 2010.

* cited by examiner

IMAGE PROCESSING SYSTEM AND METHOD FOR BODY-INSERTABLE APPARATUS

CROSS-REFERENCE TO RELATED APPLICATIONS

This application is a continuation of PCT international application Ser. No. PCT/JP2010/050556 filed on Jan. 19, 2010 which designates the United States, incorporated herein by reference, and which claims the benefit of priority from Japanese Patent Applications No. 2009-058657, filed on Mar. 11, 2009, incorporated herein by reference.

BACKGROUND OF THE INVENTION

1. Field of the Invention

The present invention relates to an image processing system, an external device, and an image processing method. More particularly, the invention relates to an image processing system having a body-insertable apparatus having imaging means, an external device, and an image processing method.

2. Description of the Related Art

Devices for observing the inside of a subject such as a human being or an animal include a tube-type endoscope and a capsule-type endoscope (hereinbelow, simply called a capsule endoscope). The tube-type endoscope includes an electronic endoscope whose tip is provided with a Charge Coupled Device (CCD) sensor and a fiber scope in which a bundle of optical fibers is inserted in a tube, and obtains images of the inside of a subject by inserting the tube from the mouse, the anus, or the like of the subject. On the other hand, the capsule endoscope has a size that a human, an animal, or the like can swallow the capsule endoscope. For example, the capsule endoscope is introduced orally to the inside of a subject and periodically captures images of the inside of the subject. The images of the inside of the subject captured are transmitted as wireless signals to an external receiving device. The observer individually or continuously reproduces a plurality of images obtained by the tube-type endoscope or the capsule endoscope and observes the images, thereby diagnosing the inside of the subject.

SUMMARY OF THE INVENTION

An image processing system according to an aspect of the present invention includes a body-insertable apparatus including an imaging unit that captures inside of a subject and an output unit that outputs image data obtained by the imaging unit to the outside; and an external device including an input unit that receives the image data, a first orientation specifying unit that specifies orientation of the body-insertable apparatus at the time of capturing the image data with respect to a reference direction, a rotation correcting unit that performs rotation correction on image data which is received by the input unit based on the orientation specified by the first orientation specifying unit, thereby aligning orientations of a plurality of pieces of image data, a screen generating unit that generates a screen displaying the image data subjected to the rotation correction in the rotation correcting unit, an average color bar generating unit that calculates an average color of the image data subjected to the rotation correction in the rotation correcting unit, generates an image of the calculated average color, and generates an average color bar in which images of the generated average colors are connected in accordance with order of the image data, and an organ image generating unit that generates an organ image, as an image of an organ in the subject, obtained by superimposing the images of the average colors generated by the average color bar generating unit, wherein the screen generating unit generates the screen in which the average color bar generated by the average color bar generating unit is incorporated, and incorporates the organ image generated by the organ image generating unit into the screen.

An image processing system according to another aspect of the present invention includes a body-insertable apparatus including an imaging unit that captures inside of a subject and an output unit that outputs image data obtained by the imaging unit to the outside; and an external device including an input unit that receives the image data, a first orientation specifying unit that specifies orientation of the body-insertable apparatus at the time of capturing the image data with respect to a reference direction, a rotation correcting unit that performs rotation correction on image data which is received by the input unit based on the orientation specified by the first orientation specifying unit, thereby aligning orientations of a plurality of pieces of image data, a screen generating unit that generates a screen displaying the image data subjected to the rotation correction in the rotation correcting unit, and a rotation amount image generating unit that generates a rotation amount image visually displaying a rotation amount used for the rotation correction for each of the image data, wherein the screen generating unit generates the screen in which the rotation amount image generated by the rotation amount image generating unit is incorporated.

An external device according to still another aspect of the present invention includes an input unit that receives image data obtained by a body-insertable apparatus including an imaging unit that captures inside of a subject; an orientation specifying unit that specifies orientation of the body-insertable apparatus at the time of capturing the image data with respect to a reference direction; a rotation correcting unit that performs rotation correction on image data which is received by the input unit based on the orientation specified by the orientation specifying unit, thereby aligning orientations of a plurality of pieces of image data; a screen generating unit that generates a screen displaying the image data subjected to the rotation correction in the rotation correcting unit; an average color bar generating unit that calculates an average color of the image data subjected to the rotation correction in the rotation correcting unit, generates an image of the calculated average color, and generates an average color bar in which images of the generated average colors are connected in accordance with order of the image data; and an organ image generating unit that generates an organ image, as an image of an organ in the subject, obtained by superimposing the images of the average colors generated by the average color bar generating unit, wherein the screen generating unit generates the screen in which the average color bar generated by the average color bar generating unit is incorporated, and incorporates the organ image generated by the organ image generating unit in the screen.

An external device according to still another aspect of the present invention includes an input unit that receives image data obtained by a body-insertable apparatus including an imaging unit that captures inside of a subject; an orientation specifying unit that specifies orientation of the body-insertable apparatus at the time of capturing the image data with respect to a reference direction; a rotation correcting unit that performs rotation correction on image data which is received by the input unit on the basis of the orientation specified by the orientation specifying unit, thereby aligning orientations of a plurality of pieces of image data; a screen generating unit that generates a screen displaying the image data subjected to the rotation correction in the rotation correcting unit; and a rotation amount image generating unit that generates a rotation amount image visually displaying a rotation amount used for the rotation correction for each of the image data, wherein the screen generating unit generates the screen in which the rotation amount image generated by the rotation amount image generating unit is incorporated.

An image processing method according to still another aspect of the present invention includes receiving image data obtained by a body-insertable apparatus including an imaging unit that captures inside of a subject; specifying orientation of the body-insertable apparatus at the time of capturing the image data with respect to a reference direction; performing rotation correction on the image data based on the specified orientation, thereby aligning orientations of a plurality of pieces of image data; generating a screen displaying the image data subjected to the rotation correction; calculating an average color of the image data subjected to the rotation correction, generating an image of the calculated average color, and generating an average color bar in which images of the generated average colors are connected in accordance with order of the image data; and generating an organ image, as an image of an organ in the subject, obtained by superimposing the images of the average colors generated at the generating the average color bar, wherein the generating the screen, includes generating the screen in which the generated average color bar is incorporated, and incorporating the generated organ image.

An image processing method according to still another aspect of the present invention includes receiving image data obtained by a body-insertable apparatus including an imaging unit that captures inside of a subject; specifying orientation of the body-insertable apparatus at the time of capturing the image data with respect to a reference direction; performing rotation correction on image data which is received by the input unit on the basis of the specified orientation, thereby aligning orientations of a plurality of pieces of image data; generating a screen displaying the image data subjected to the rotation correction; and generating a rotation amount image visually displaying a rotation amount used for the rotation correction for each of the image data, wherein the generating the screen includes generating the screen in which the generated rotation amount image is incorporated.

An image processing system according to still another aspect of the present invention includes a body-insertable apparatus including an imaging means for capturing inside of a subject and an output means for outputting image data obtained by the imaging unit to the outside; and an external device including an input means for receiving the image data, an orientation specifying means for specifying orientation of the body-insertable apparatus at the time of capturing the image data with respect to a reference direction, a rotation correcting means for performing rotation correction on image data which is received by the input means based on the orientation specified by the orientation specifying means, thereby aligning orientations of a plurality of pieces of image data, a screen generating means for generating a screen displaying the image data subjected to the rotation correction by the rotation correcting means, an average color bar generating means for calculating an average color of the image data subjected to the rotation correction by the rotation correcting means, generating an image of the calculated average color, and generating an average color bar in which images of the generated average colors are connected in accordance with order of the image data, and an organ image generating means for generating an organ image, as an image of an organ in the subject, obtained by superimposing the images of the average colors generated by the average color bar generating means, wherein the screen generating means generates the screen in which the average color bar generated by the average color bar generating means is incorporated, and incorporates the organ image generated by the organ image generating means into the screen.

An image processing system according to still another aspect of the present invention includes a body-insertable apparatus including an imaging means for capturing inside of a subject and an output means for outputting image data obtained by the imaging means to the outside; and an external device including an input means for receiving the image data, an orientation specifying means for specifying orientation of the body-insertable apparatus at the time of capturing g the image data with respect to a reference direction, a rotation correcting means for performing rotation correction on image data received by the input means based on the orientation specified by the orientation specifying means, thereby aligning orientations of a plurality of pieces of image data, a screen generating means for generating a screen displaying the image data subjected to the rotation correction in the rotation correcting means, and a rotation amount image generating means for generating a rotation amount image visually displaying a rotation amount used for the rotation correction for each of the image data, wherein the screen generating means generates the screen in which the rotation amount image generated by the rotation amount image generating means is incorporated.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
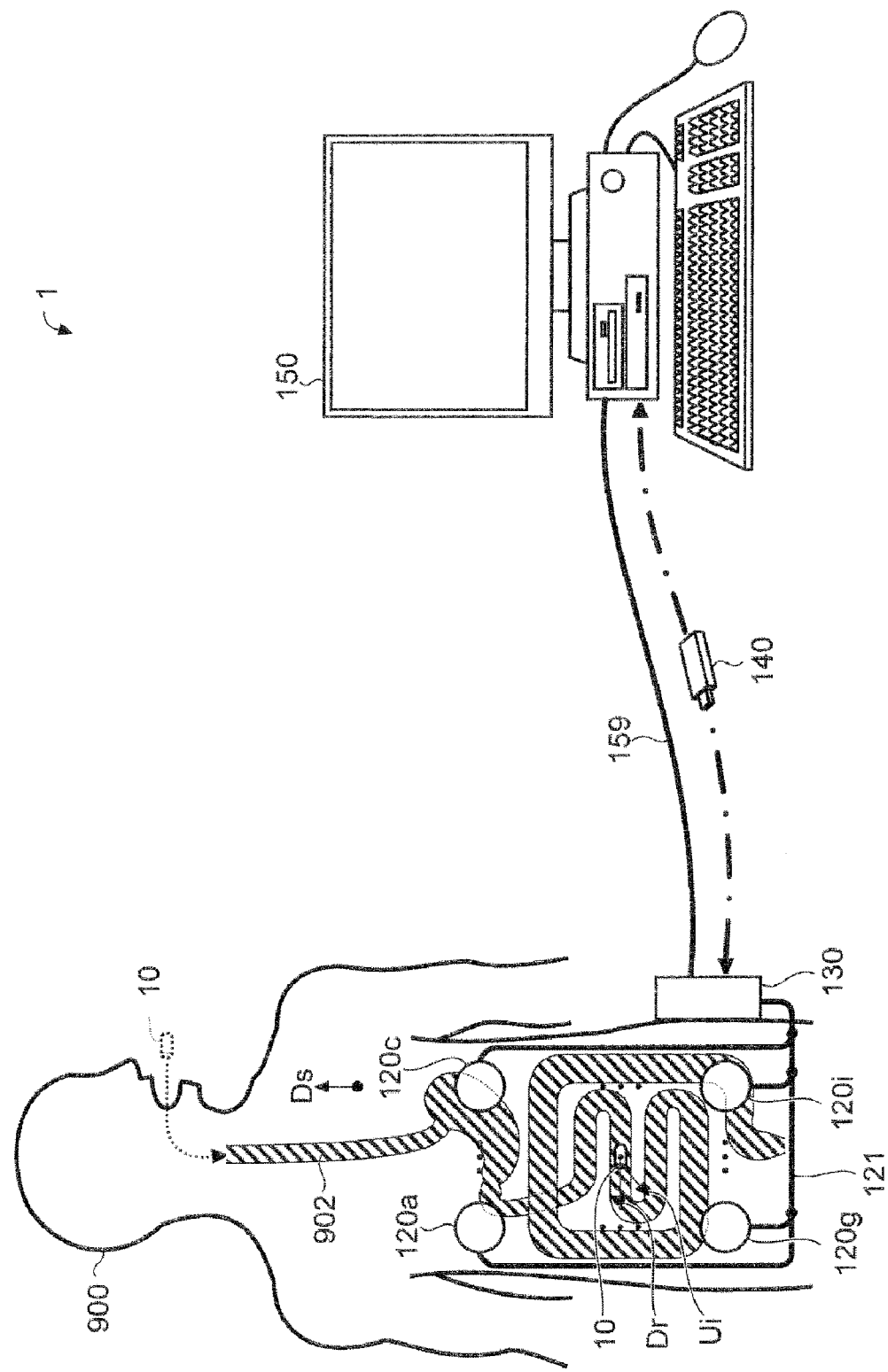
FIG. 1 is a schematic diagram showing a schematic configuration of a medical system according to a first embodiment.

Best modes for carrying out the present invention will be described in detail below with reference to the drawings. In the following description, the drawings just schematically show shapes, sizes, and positional relations to a degree that the content of the present invention can be understood. Therefore, the present invention is not limited only to the shapes, sizes, and positional relations shown in the drawings. In the drawings, to clearly show the configuration, a part of hatching in cross sections is omitted.

First Embodiment

In the following, the configuration and operation of a medical system 1 according to a first embodiment of the invention will be described in detail below with reference to the drawings. In the first embodiment, the case of using a capsule body-insertable apparatus (hereinbelow, called capsule medical device) 10 introduced in a subject 900 orally and capturing images of the inside of the subject 900 by executing imaging operation while traveling in a lumen 902 (refer to FIG. 1) from the stomach to the anus of the subject 900 will be described as an example. The invention, however, is not limited to the case but can be variously modified to, for example, the case of using a capsule medical device floating in liquid stored in a stomach, small intestine, large intestine, or the like of the subject 900 and the case of using a capsule medical device introduced by applying a magnetic field from the outside of the body to a magnet fixed in the capsule medical device.

Configuration

FIG. 1 is a schematic diagram showing a schematic configuration of the medical system 1 according to the first embodiment. As illustrated in FIG. 1, the medical system 1 has the capsule medical device 10 introduced in the subject 900, for example, via the oral route, a receiving device 130 for transmitting/receiving image data, a control instruction, and the like to/from the capsule medical device 10 by performing wireless communication with the capsule medical device 10, and a display device 150 for executing predetermined process on the image data received from the capsule medical device 10 by the receiving device 130 and displaying the processed image data to the observer. The receiving device 130 and the display device 150 are external devices disposed on the outside of the subject 900.

To the receiving device 130, a portable recording medium 140 such as a flash memory (registered trademark) or a smart card (registered trademark) can be inserted. In the portable recording medium 140, for example, image data and the like received from the capsule medical device 10 is stored. The observer moves the portable recording medium 140 from the receiving device 130 to the display device 150 and executes a predetermined process such as a process of reproducing image data stored in the portable recording medium 140 or a converting process by using the display device 150. As the display device 150, an information processor such as a personal computer or a workstation, a display such as a liquid crystal display or an organic EL display can be used.

Capsule Medical Device

Figure 2:
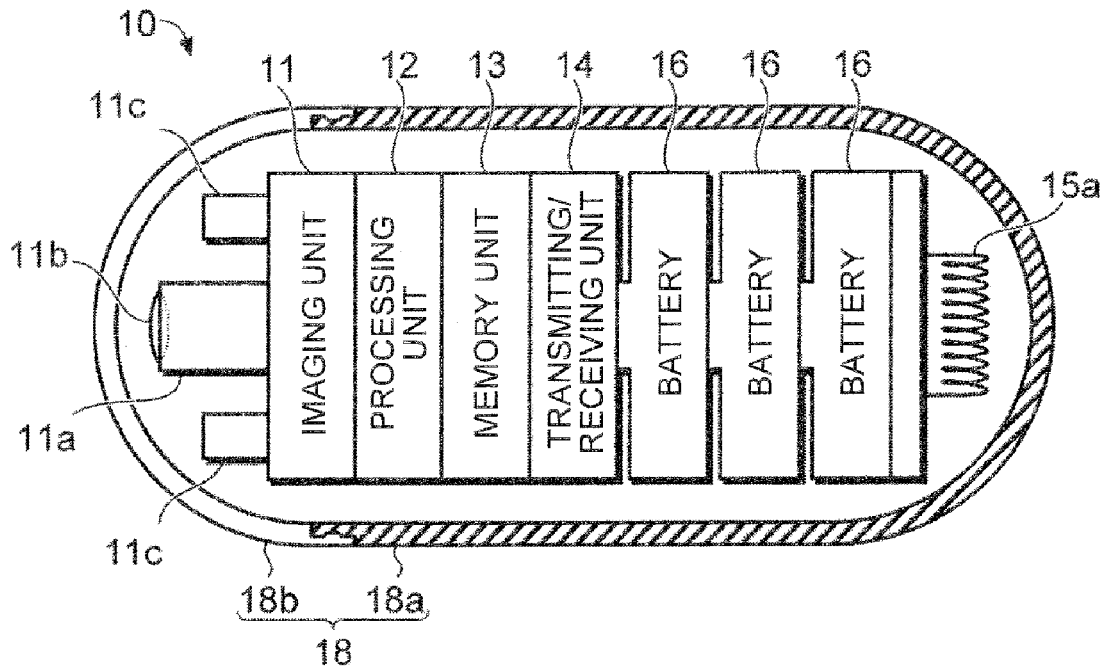
FIG. 2 is a block diagram showing a schematic internal configuration of a capsule medical device according to the first embodiment.
Figure 3:
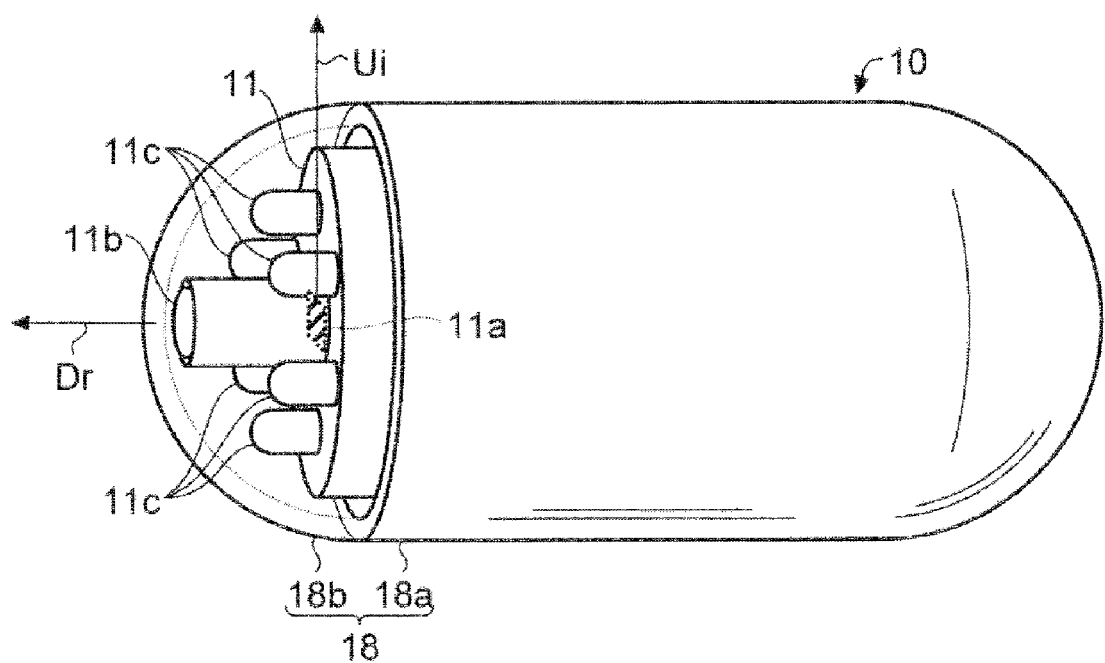
FIG. 3 is a perspective view illustrating schematic appearance of the capsule medical device according to the first embodiment.
Figure 4:
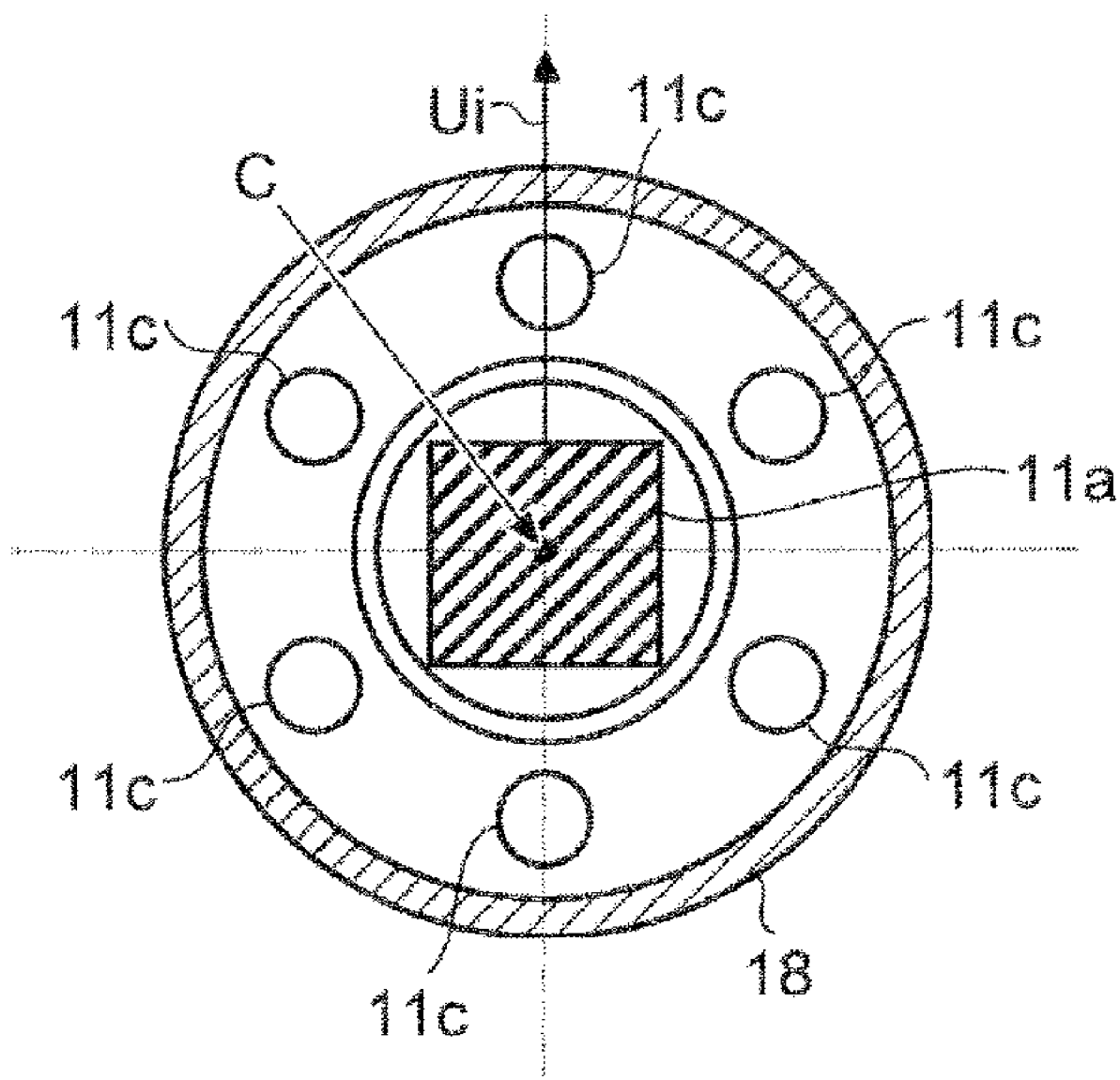
FIG. 4 is a cross section showing a sectional structure when the capsule medical device is cut in a plane including an imaging plane of a CCD array in an imaging unit according to the first embodiment.

An example of the schematic configuration of the capsule medical device 10 is shown in FIGS. 2 to 4. FIG. 2 is a block diagram showing a schematic internal configuration of the capsule medical device 10. FIG. 3 is a perspective view showing a schematic appearance of the capsule medical device 10. FIG. 4 is a cross section showing a sectional structure when the capsule medical device 10 is cut in a plane including an imaging plane of a CCD array 11a in an imaging unit 11.

As shown in FIG. 2, the capsule medical device 10 has: the imaging unit 11 for illuminating and imaging the inside of the subject 900, a processing unit 12 for executing a process on an image generated by the imaging unit 11 and other various processes, a memory unit 13 for storing the image data and the like processed by the processing unit 12, a transmitting/receiving unit 14 and an antenna 15a for transmitting/receiving a signal to/from the receiving device 130, and one or more batteries 16 for supplying power to the inside of the capsule medical device 10.

The imaging unit 11, the processing unit 12, the memory unit 13, the transmitting/receiving unit 14, and the battery 16 are housed in a water-tight casing 18 made by a container 18a and a cap 18b. As shown in FIG. 3, one end of the container 18a has a hemispherical dome shape and the other end has an almost cylindrical shape or a semielliptical shape which is open. On the other hand, the cap 18b has a hemispherical shape and is fit in the opening of the container 18a, thereby water-tightly sealing the casing 18. At least the cap 18b is made of transparent resin or the like.

The imaging unit 11 is imaging means for imaging the inside of the subject 900 and includes an LED 11c for illuminating the inside of the subject 900, a CCD array 11a in which Charge Coupled Devices (CCDs) as light emitting elements are arranged in a matrix, an objective lens 11b disposed on the light reception face side of the CCD array 11a, and a drive circuit (not shown) for driving the LED 11c and a drive circuit (not shown) for driving the CCD array 11a. The imaging unit 11 periodically operates (for example, twice per second), thereby imaging the inside of the subject 900 and generating image data. The generated image data is read by the drive circuit and supplied to the processing unit 12 in an almost real-time manner.

The processing unit 12 executes predetermined signal process on input image data and supplies the processed image data to the transmitting/receiving unit 14. The transmitting/receiving unit 14 mainly functions as output means for outputting image data captured by the imaging unit 11 to the receiving device 130 on the outside. Therefore, the image data subjected to the predetermined signal process by the processing unit 12 is transmitted by radio in an almost real-time manner from the transmitting/receiving unit 14 to the receiving device 130 via the antenna 15a. The invention, however, is not limited to the case. Image data subjected to the predetermined image signal process may be stored in the memory unit 13 and, after the capsule medical device 10 is taken from the subject 900, the image data may be taken from the memory unit 13. Preferably, to the transmitted/stored image data, for example, a time stamp is added by the processing unit 12 so that imaging time, imaging timing, and the like are known.

As shown in FIGS. 1, 3, and 4, the LED 11c and the CCD array 11a are disposed in the casing 18 so that an illuminating/imaging direction Dr is directed to the outside of the casing 18 via the transparent cap 18b. The CCD array 11a is disposed in an almost center in a section perpendicular to the longitudinal direction of the casing 18. On the other hand, a plurality of LEDs 11c are disposed point-symmetrical or line-symmetrical so as to surround the CCD array 11a in the section. In the first embodiment, a direction in a plane parallel to the light reception face of the CCD array 11a is set as a specified direction Ui of the capsule medical device 10. For clarification of explanation, a certain direction is set to a direction which passes through the center C of the light reception face of the COD array 11a and is an upward direction on a screen in the case of displaying an image generated by the CCD array 11a as it is on, for example, the display device 150. Therefore, in the invention, in the case of displaying image data read from the COD array 11a as it is on the display device 150, the specified direction Ui and the upward direction Du on the screen (refer to FIG. 8) coincide with each other.

As the antenna 15a of the capsule medical device 10, for example, an antenna having directivity is used. In the first embodiment, a loop antenna is used as the antenna 15a. However, the invention is not limited to the loop antenna. Any antenna is applicable as long as it can detect the direction of the antenna 15a with respect to a reference (in the first embodiment, as an example, a direction connecting the head and the foot of the subject 900, in the following, called a reference direction Ds) on the basis of the phase, strength, or the like in an antenna 120 as an observation point, of an electromagnetic wave (hereinbelow, including electric wave) generated from the antenna 15a of the capsule medical device 10 as a signal source.

The antenna 15a having the directivity is fixed on the inside of the casing 18. The antenna 15a is fixed in the casing 18 so that the center line of the loop of the antenna 15a (corresponding to the symmetrical axis of an electric field distribution shape of the electromagnetic wave generated by the antenna 15a) and the longitudinal direction of the capsule medical device 10 do not become parallel to each other. Consequently, even in the case where the capsule medical device 10 rotates using the center line in the longitudinal direction as an axis, the orientation of the specified direction Ui of the capsule medical device 10 with respect to the reference direction Ds can be specified on the basis of the phase, strength, or the like of the electromagnetic wave in a plurality of observation points in the receiving device 130.

Preferably, the orientation of the center line of the antenna 15a having directivity is made coincide with the orientation of the specified direction Ui. Since the orientation of the reference direction Ds of the antenna 15a can be used directly as the orientation with respect to the reference direction Ds of the specified direction Ui, the process in the receiving device 130 which will be described later can be lessened.

Receiving Device

Figure 5:
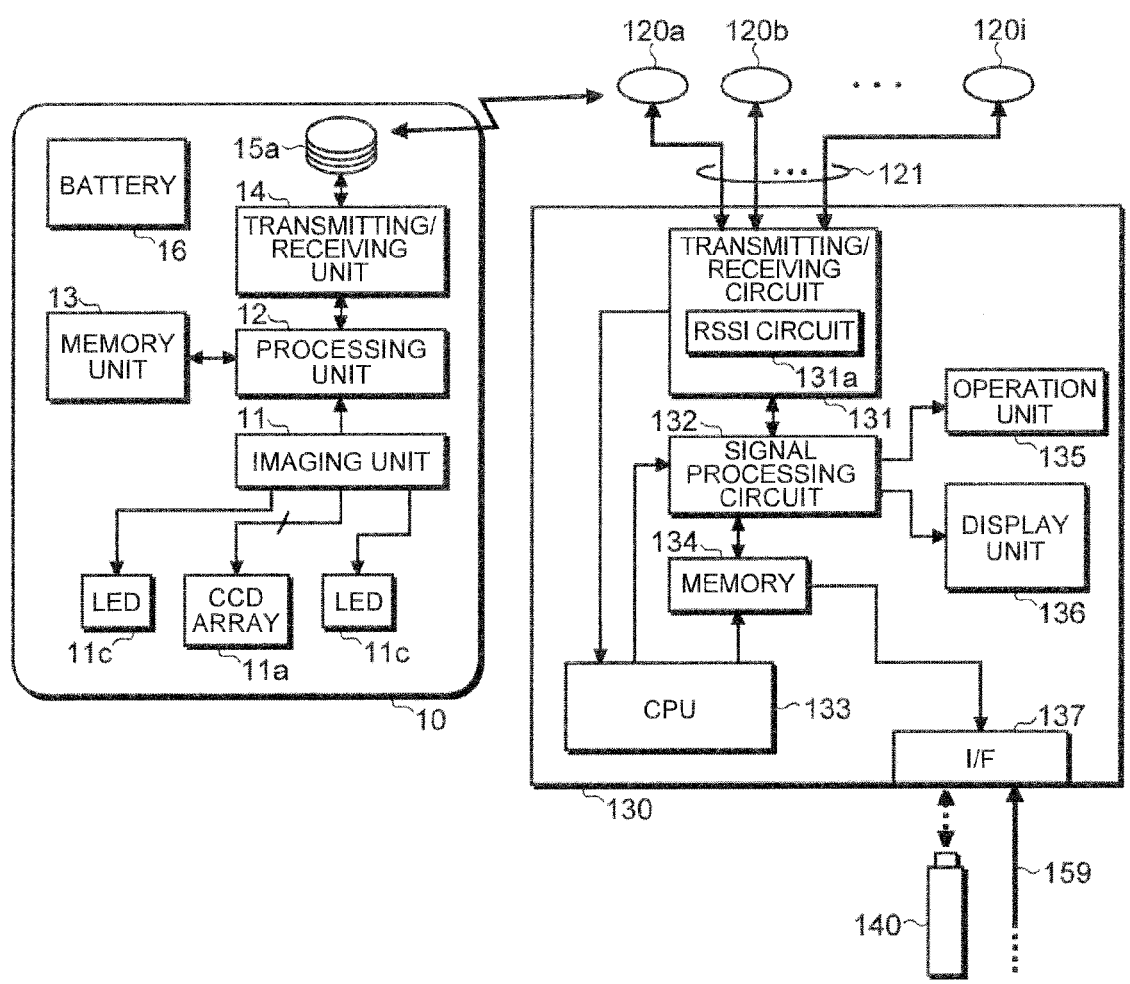
FIG. 5 is a block diagram showing an example of a schematic configuration of a receiving device according to the first embodiment.
Figure 6:
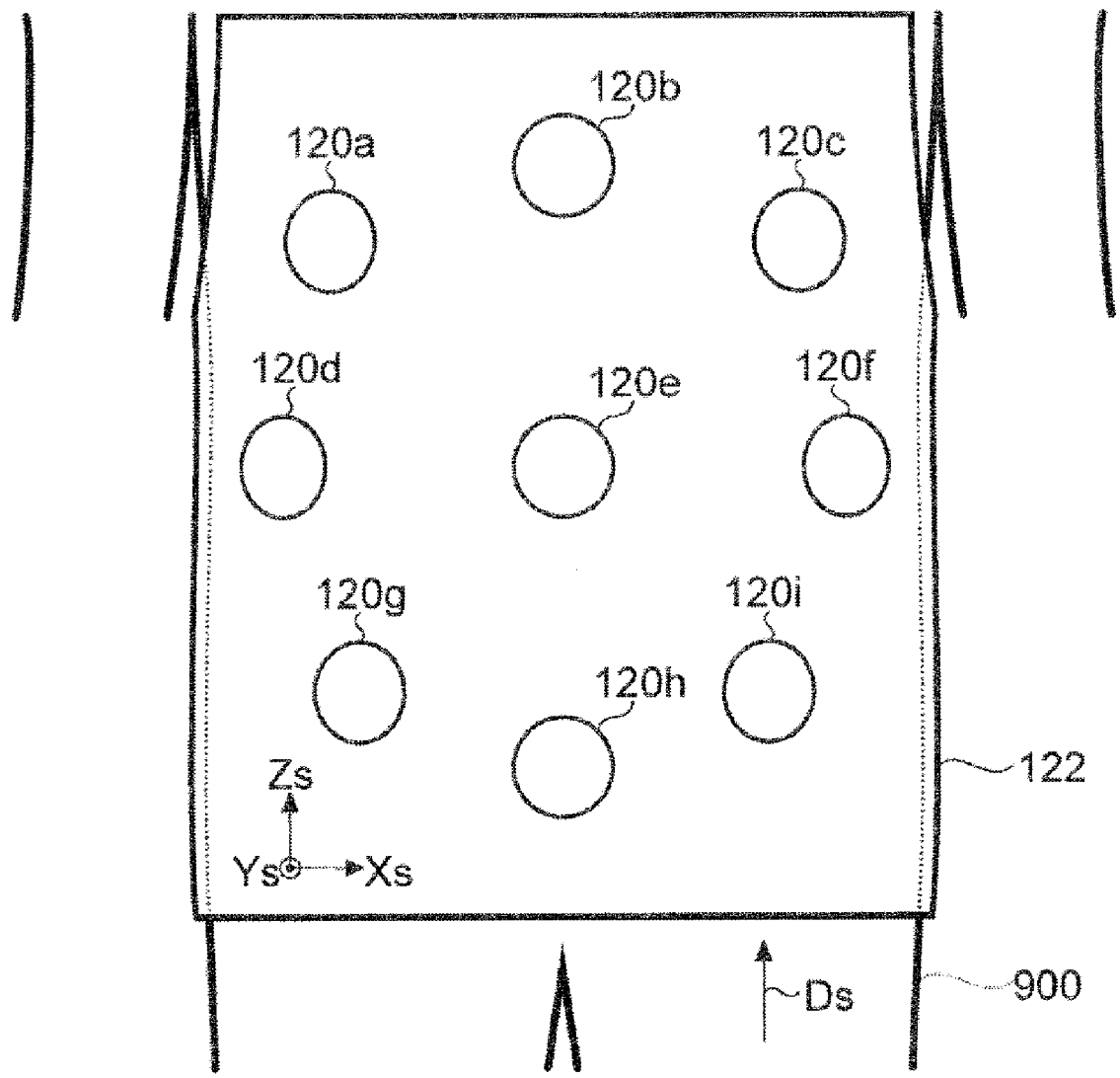
FIG. 6 is a diagram showing an example of arrangement of antennas on the receiving device side according to the first embodiment.

As shown in FIGS. 1 and 6, image data transmitted by radio from the capsule medical device 10 is received by a plurality of antennas 120a to 120i (hereinbelow, reference numeral of arbitrary one of the antennas 120a to 120i will be set as 120) disposed on the surface of the subject 900 and input to the receiving device 130 disposed on the outside of the subject 900 via a cable 121. An example of a schematic configuration of the receiving device 130 according to the first embodiment is shown in the block diagram of FIG. 5.

As shown in FIG. 5, the receiving device 130 has a transmitting/receiving circuit 131 for transmitting/receiving a signal to/from the capsule medical device 10 via the antenna 120, a signal processing circuit 132 for executing a predetermined process on the signal (particularly, image data) input from the transmitting/receiving circuit 131, a memory 134 for storing the image data or the like subjected to the predetermined process, and an operation unit 135 and a display unit 136 realizing the Graphical User Interface (GUI) function for making the observer enter various operations and instructions to the capsule medical device 10 and the receiving device 130. The transmitting/receiving circuit 131 also has a function of phase detecting means which detects the phase in each of the antennas 120a to 120i, of an electromagnetic wave transmitted from the antenna 15a of the capsule medical device 10. The transmitting/receiving circuit 131 also has, as strength detecting means detecting strength in each of the antennas 120a to 120i, of the electromagnetic wave transmitted from the antenna 15a of the capsule medical device 10, for example, a Received Signal Strength Indicator (RSSI) circuit 131a for detecting strength of the electromagnetic wave received in each of the antennas 120. That is, the transmitting/receiving circuit 131 also functions as strength/phase detecting means detecting strength and phase in each of the antennas 120a to 120i, of the electromagnetic wave transmitted from the antenna 15a of the capsule medical device 10.

The receiving device 130 also has a CPU 133 functioning as orientation specifying means estimating spatial spread (electric field distribution) of the electromagnetic wave from the phase of the electromagnetic wave in each of the antennas 120 detected by the transmitting/receiving circuit 131 and the strength in each of the antennas 120 detected by the RSSI circuit 131a and specifying orientation with respect to the reference direction Ds of the antenna 15a of the capsule medical device 10 (that is, orientation with respect to the reference direction Ds of the specified direction Ui).

In the first embodiment, the antenna 15a of the capsule medical device 10 functions as a signal source generating a sign (electromagnetic wave in the example) for orientation detection for specifying the orientation of the capsule medical device 10 (that is, tilt of the specified direction Ui) with respect to the reference direction Ds, the antenna 120 functions as an observation point for observing the sign (electromagnetic wave) for orientation detection generated from the signal source (antenna 15a), and the CPU 133 of the receiving device 130 functions as orientation specifying means specifying the orientation of the capsule medical device 10 (that is, tilt of the specified direction Ui) with respect to the reference direction Ds from the strength and phase of the sign (electromagnetic wave) for orientation detection observed at the observation point (antenna 120). For specification of the orientation of the capsule medical device 10 using the electromagnetic wave, for example, convergence calculation by iterative operation using the least square method.

The plurality of antennas 120a to 120i are, for example, dipole antennas, loop antennas, or the like and are fixed to a jacket 122 the subject 900 can wear as shown in FIG. 6. The number of antennas 120, an arrangement pattern, and an object to which the antennas 120 are fixed are not limited to those shown in FIG. 6 but can be variously modified as long as the number and the arrangement pattern by which the CPU 133 can estimate/specify the spatial spread (electric field distribution) of the electromagnetic wave (sign for orientation detection) emitted from the antenna 15a of the capsule medical device 10 as a signal source on the basis of the strength, phase, and the like of the electromagnetic wave (sign for orientation detection) observed at the antenna 120 as an observation point and the fixation object which can be substantially fixed to the subject 900 are used. In the description, the number of the antennas 120 is at least two.

The information of the orientation (hereinbelow, called orientation data) with respect to the reference direction Ds of the specified direction Ui specified by the CPU 133 is temporarily stored in association with image data received simultaneously or around the same time from the capsule medical device 10 into the memory 134. The memory 134 functions as a buffer temporarily storing image data.

After that, the image data and the orientation data stored in the memory 134 is either accumulated in the portable recording medium 140 via an interface (I/F) 137 or transmitted from the interface (I/F) 137 to the display device 150 via a communication cable 159 in an almost real-time manner. The interface 137 can be variously changed according to the data input/output method such as a Universal Serial Bus (USB) interface or a communication interface used for Local Area Network (LAN) or the like.

Display Device

Figure 7:
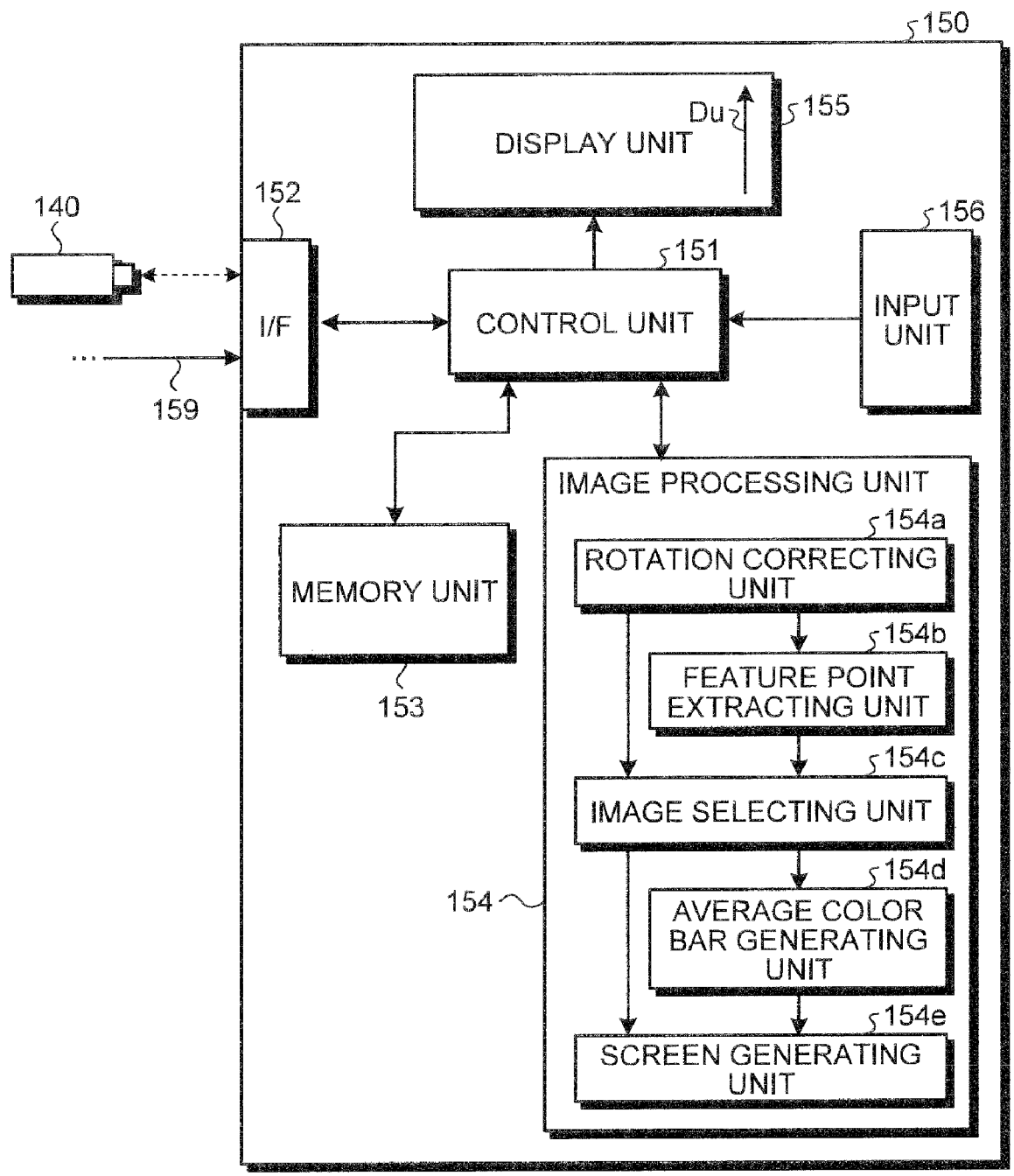
FIG. 7 is a block diagram showing an example of a schematic configuration of a display device according to the first embodiment.

As described above, the display device 150 is constructed by an information processor such as a personal computer or a workstation or a display such as a liquid crystal display or an organic EL display. As shown in FIGS. 1 and 7, the display device 150 has a control unit 151 for controlling operations and input/output of data in the display device 150, a memory unit 153 for temporarily storing image data and orientation data or the like input from an interface unit 152 via the portable recording medium 140 or the communication cable 159, an image processing unit 154 for executing a predetermined process on input image data and generating a screen provided to the observer, a display unit 155 for displaying the screen generated by the image processing unit 154, and an input unit 156 with which the observer enters various instructions on the basis of the screen displayed on the display unit 155. FIG. 7 is a block diagram showing a schematic configuration example of the display device 150 according to the first embodiment.

The interface unit 152 functions as input means that enters image data (including orientation data) from the capsule medical device 10 via the receiving device 130. The image data and the orientation data entered from the interface unit 152 is temporarily stored in the memory unit 153 via the control unit 151. After that, the image data and the orientation data is properly input to the image processing unit 154 and is subjected to a predetermined process. The processed image data may be stored again in, for example, the memory unit 153.

The image processing unit 154 executes a predetermined process which will be described later on the input image data and the orientation data and, after that, generates a GUI screen to be provided for the observer by using the processed image data. The GUI screen generated is supplied to the display unit 155 via the control unit 151 and displayed on the display unit 155. The display unit 155 and the input unit 156 provide the GUI function using the GUI screen being displayed to the observer. The observer selects a target function by inputting variously operations from the input unit 156 such as a mouse and a keyboard, and displays/reproduces a desired image on the display unit 155. The observer reads a displayed/reproduced image, thereby diagnosing the inside of the subject 900.

The image processing unit 154 will be described more specifically. As shown in FIG. 7, the image processing unit 154 includes a rotation correcting unit 154a for rotation-correcting image data, a feature point extracting unit 154b for extracting a feature point of image data, an image selecting unit 154c for selecting image data on the basis of the feature point extracted by the feature point extracting unit 154b, an average color bar generating unit 154d that generates an average color bar 60 by using the selected image data, and a screen generating unit (screen generating means) 154e that generates a GUI screen by using the selected image data and the average color bar 60.

The rotation correcting unit 154a is rotation-correcting means that rotation-corrects corresponding image data on the basis of the orientation of the capsule medical device 10 specified by the CPU 133 as the rotation specifying means, and rotation-corrects image data so that the tilts (hereinbelow, simply called rotation amounts) on the display plane of the reference direction Ds of each image with respect to the upward direction Du (refer to FIG. 8) of the screen coincide among a plurality of images.

In the first embodiment, each of image data pieces is rotation-corrected so that the reference direction Ds and the upward direction Du of the screen coincide with each other in all of images. A correction amount (that is, a rotation amount) at the time of the rotation correction can be specified from the tilt on the display plane of the specified direction Ui of each image with respect to the reference direction Ds. Specifically, by specifying how much the specified direction Ui turns with respect to the reference direction Ds in a plane parallel to the light reception face of the COD array 11a, the rotation amount (correction amount) used for the rotation correction can be specified. In other words, by projecting the reference direction Ds to the light reception face and obtaining the angle of the specified direction Ui with respect to the reference direction Ds after projection, the rotation amount A used for the rotation correction can be specified. The rotation correcting unit 154*a* rotation-corrects image data in accordance with the specified rotation amount, thereby making the reference direction Ds in the image data coincide with the upward direction Us of the screen. As a result, the orientation of a region in an image captured as a subject can be made coincide in a plurality of images. The image data subjected to the rotation correction may be held in, for example, the memory 134 or the like regardless of whether it is selected.

The feature point extracting unit 154*b* extracts a feature point of each image data subjected to the rotation correction (that is, on the frame unit basis) and supplies it as an extraction result to the image selecting unit 154*c*.

To the image selecting unit 154*c*, the image data subjected to the rotation correction is also entered. The image selecting unit 154*c* selects image data in which a scene change occurs or image data including a peculiar shape on the basis of the feature point extraction result entered from the feature point extracting unit 154*b*, and supplies it to the average color bar generating unit 154*d* and the screen generating unit 154*e*.

The average color bar generating unit 154*d* functions as average color generating means generating the average color bar 60 by calculating an average color of the image data subjected to the rotation correction and connecting generated images of average colors in accordance with the order of the image data. In the embodiment, the average color bar generating unit 154*d* generates an average color bar by using image data selected by the image selecting unit 154*c*. The details of the operation of the average color bar generating unit 154*d* and the average color bar 60 generated by the average color bar generating unit 154*d* will be described later.

Figure 8:
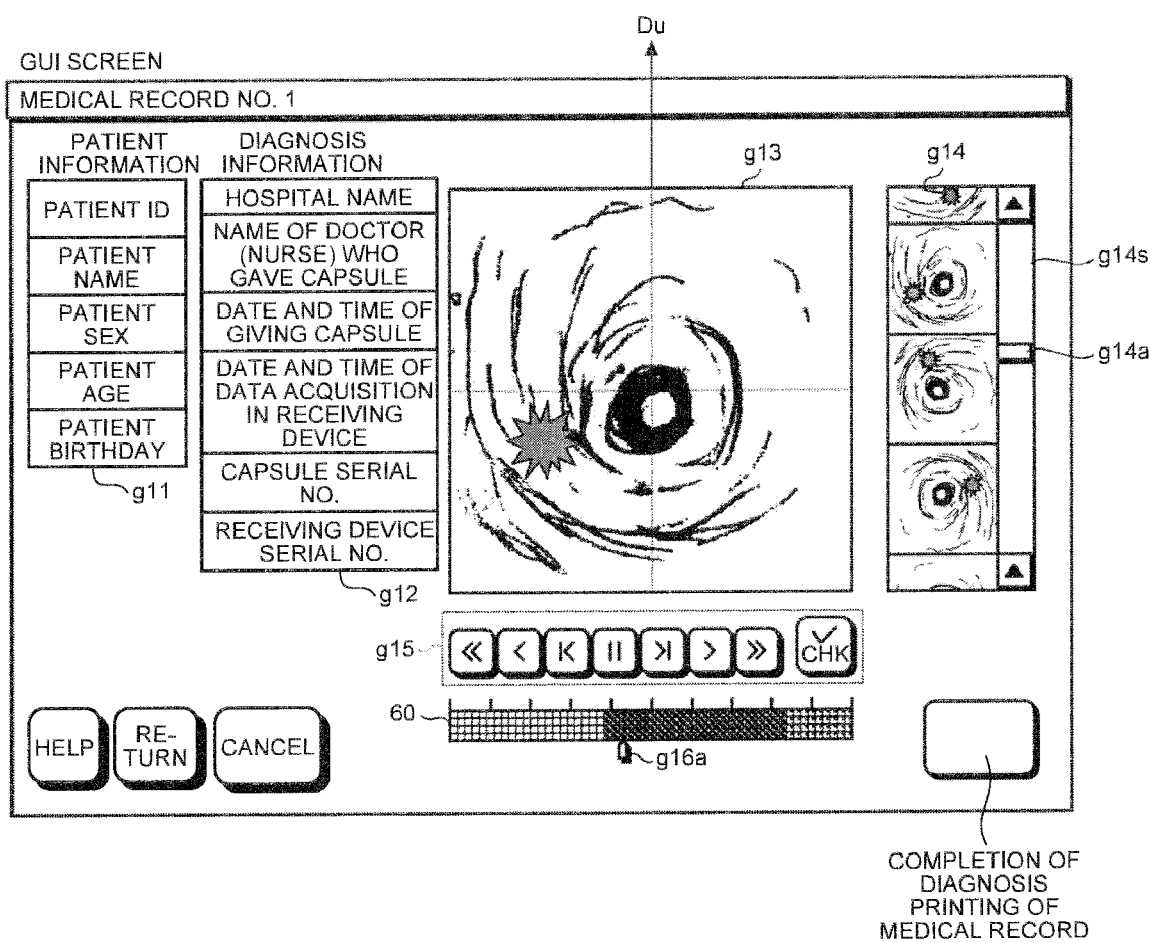
FIG. 8 is a diagram illustrating an example of a GUI screen generated according to the first embodiment.

The screen generating unit 154*e* generates, for example, a GUI screen as illustrated in FIG. 8. As shown in FIG. 8, in the GUI screen generated by the image processing unit 154, patient information g11, diagnosis information g12, a main image display region g13, a sub image display region g14, reproduction control buttons g15, and the average color bar 60 are incorporated. The observer switches an image displayed in the main image display region g13 by selecting the reproduction control buttons g15 by operating the input unit 156 such as the mouse. For example, in the case where the observer selects an image reproduction stop button (the "∥" button in the reproduction control buttons g15), using the image being displayed in the main image display region g13 as a center, reduction images preceding and subsequent to the image being displayed are displayed. The arrow Du direction in the main image display region g13 is the upward direction Du of the screen.

Further, in the sub image display region g14, a scroll bar g14*s* and a slider g14*a* are disposed adjacent to each other. The scroll bar g14*s* is linked to the time base of capturing timings of images successively obtained. Therefore, the observer can slide a reduction image displayed in the sub image display region g14 by moving the slider g14*a* along the scroll bar g14*s*.

Figure 10:
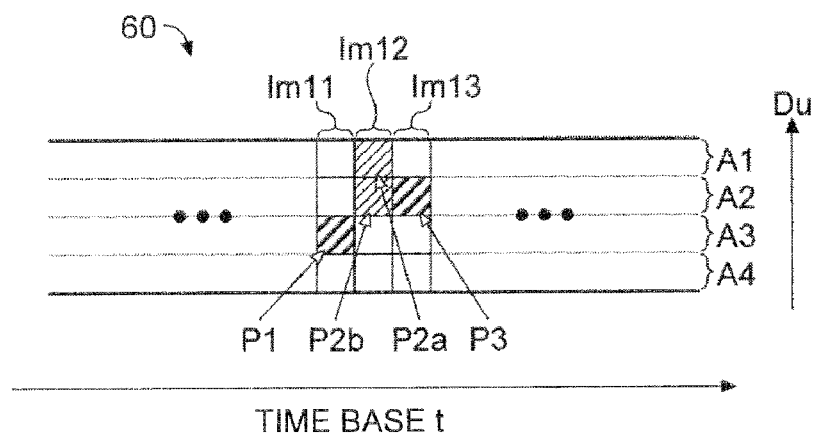
FIG. 10 is a diagram showing an example of an average color bar generated according to the first embodiment.
Figure 15:
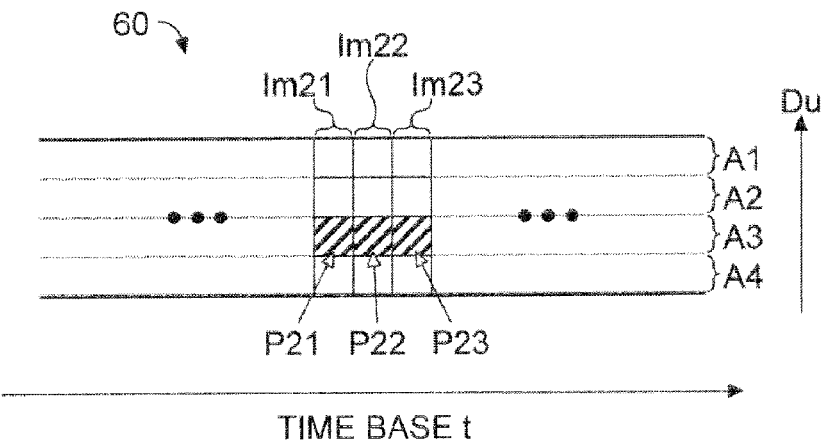
FIG. 15 is a diagram showing an example of an average color bar generated by using image data after the rotation correction in step S127 in FIG. 13.

The average color bar 60 is a GUI generated by generating images schematically expressing colors as characteristics of the images for all of image data and arranging the images along the time base "t" (refer to FIG. 10 or 15). The arrangement of images along the time base corresponds to, as a result, arrangement of images along the movement locus in the lumen 902 of the capsule medical device 10. The color as a feature of each image (average color) can be obtained by, for example, dividing a target image into a plurality of pieces (for example, four pieces) in the vertical direction and averaging colors at feature points in the divided regions. Therefore, the observer can visually recognize the place in the lumen 902, in which a region to be noted exists by reading the average color bar 60.

In the average color bar 60, the slider g16*a* indicating image data in a position on the time bar, which is presently displayed is currently expressed in the main image display region g13. The observer can switch image data to be displayed in the main image display region g13 to image data in a target position on the time base by moving the slider g16*a* by using the mouse or the like in the input unit 156.

Operation

Figure 9:
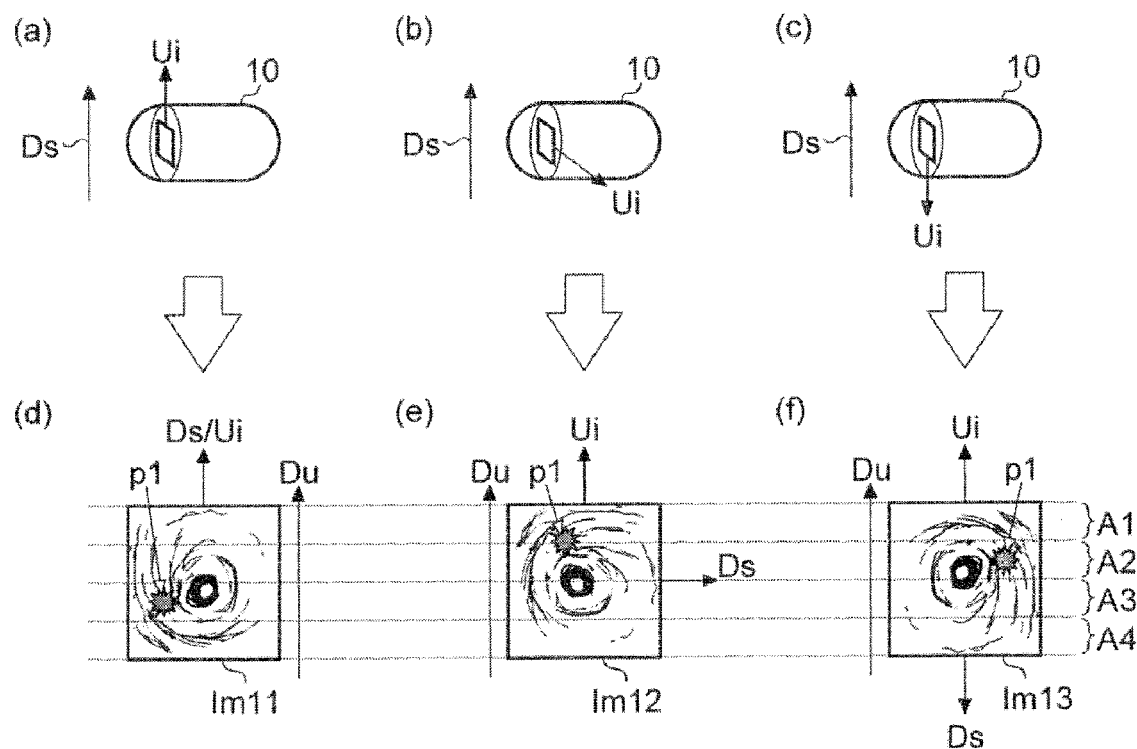
FIG. 9 is a diagram showing successive image data obtained by imaging the same region in a subject by the capsule medical device in the first embodiment.

As described above, the subject 900 of the capsule medical device 10 may have any posture. Therefore, the capsule medical device 10 passively moves in the lumen of the subject 900 while rotating in various directions by its peristaltic movement. In an example shown in (a) to (c) in FIG. 9, when it is assumed that the reference direction Ds in image data Im11 captured at a first imaging timing and the specified direction Ui are the same, the specified direction Ui in image data Im12 captured at a second imaging timing as the immediately successive timing has a tilt of 90° from the reference direction Ds and, further, the specified direction Ui has a tilt of 180° from the reference direction Ds at a third imaging timing in image data Im13 captured at the immediately successive timing. That is, from (a) to (c) in FIG. 9, the capsule medical device 10 turns by 90° each around the symmetrical axis in the longitudinal direction. Therefore, as shown in (d) to (f) in FIG. 9, the specified direction Ui in the image data Im11 to Im13 captured by the capsule medical device 10 turns by 90° each with respect to the reference direction Ds. As a result, as shown in (d) to (f) in FIG. 9, the reference direction Ds of the image data Im11 to Im13 displayed in the screen turns by 90° each with respect to the upward direction Du of the screen. When the reference direction Ds of image data arbitrarily turns with respect to the upward direction Du of the screen, there is a case such that a part p1 as a feature included in a division region A3 in division regions A1 to A4 in the image data Im11 captured at the first imaging timing lies in two regions of the division regions A1 and A2 in the image data Im12 captured at the second imaging timing, and is included in the division region A2 in the image data Im13 captured at the third imaging timing. FIG. 9 is a diagram showing the image data Im11 to Im13 which is successive in time obtained when the capsule medical device 10 images the same part p1 in the subject 900.

As shown in FIG. 9, when the specified direction Ui of image data obtained by imaging the same part p1 varies with respect to the reference direction Ds, cases occur such that the position of the part p1 indicated in the average color bar 60 generated by using the image data Im11 to Im13 varies without being arranged in the horizontal direction as shown in FIG. 10 (refer to regions P1 to P3 in FIG. 10) or the density of color decreases since the part lies in different division regions (refer to the regions P2*a* and P2*b* in FIG. 10). FIG. 10 is a diagram showing an example of the average color bar 60 generated according to the first embodiment. In FIG. 10, the regions P1, P2*a* and P2*b*, and P3 denote images obtained by averaging the feature colors in the division regions (A3, A1 and A2, and A2) each including the same part p1, respectively.

The operation of the medical system 1 according to the first embodiment capable of preventing occurrence of cases as described above will now be described in detail with reference to the drawings. In the first embodiment, as described above, image data is two-dimensionally rotation-corrected on the display face so that the reference direction Ds of each of images coincides with the upward direction Du of the screen.

Figure 11:
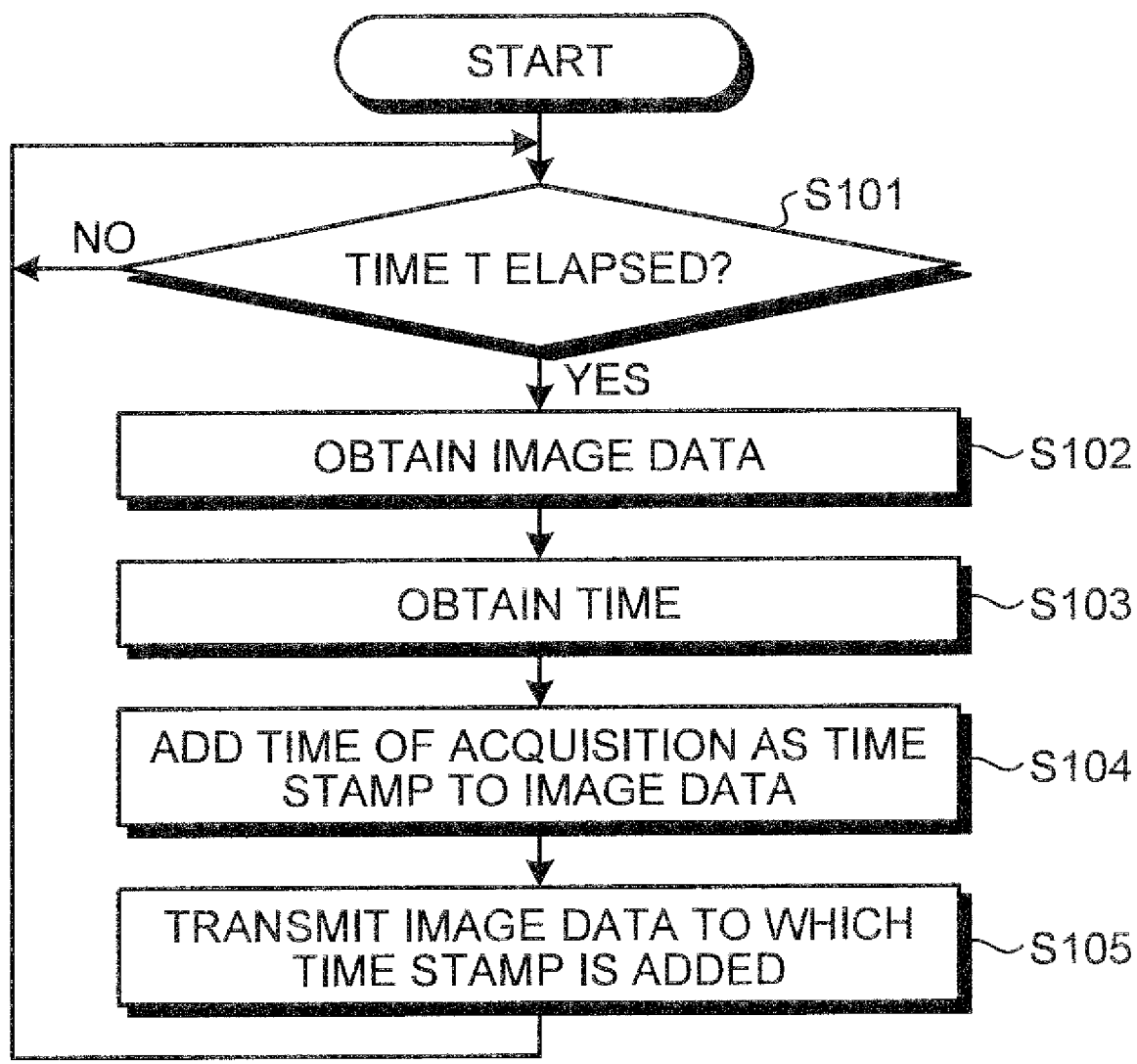
FIG. 11 is a flowchart showing an example of outline operation of the capsule medical device according to the first embodiment.
Figure 12:
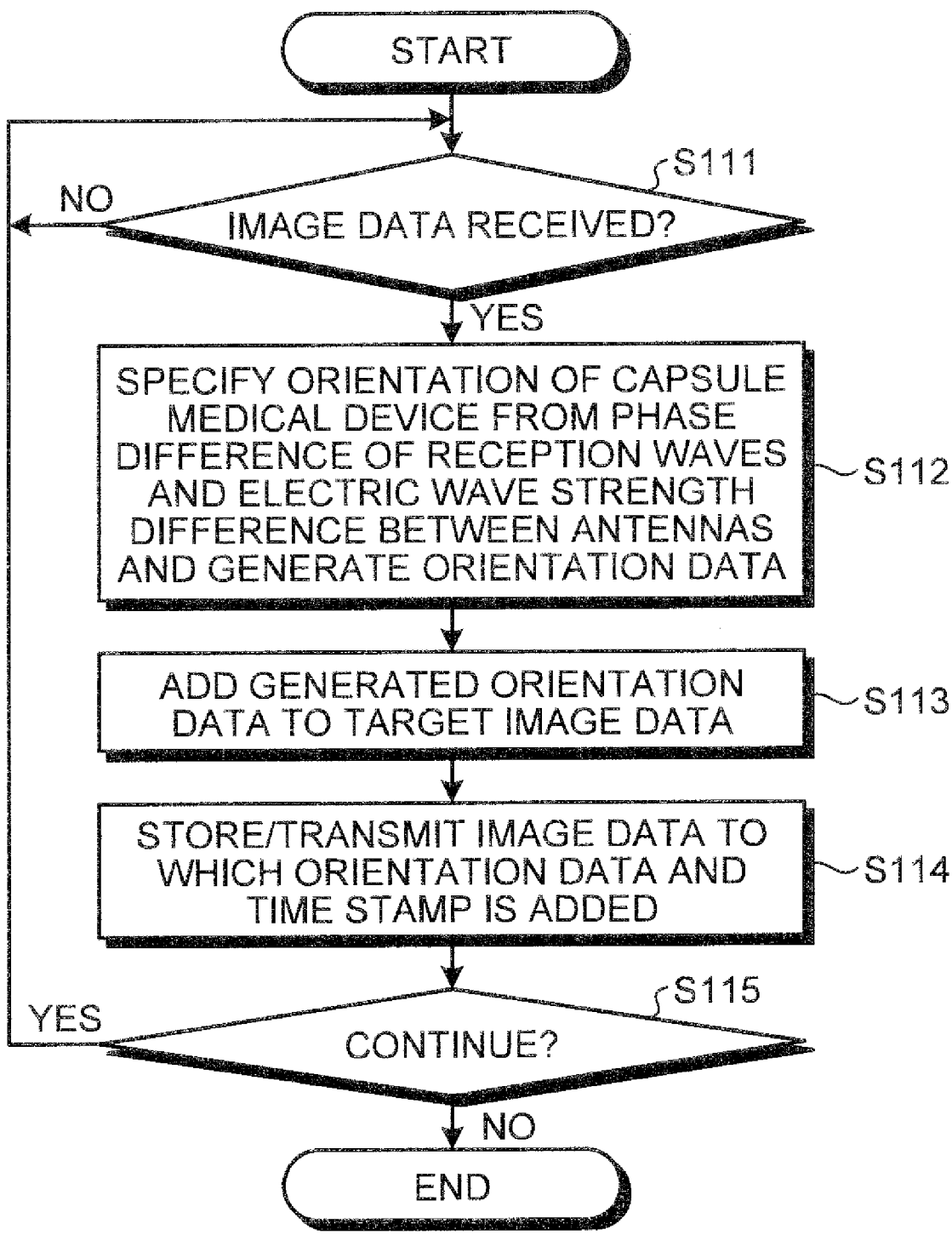
FIG. 12 is a flowchart showing an example of outline operation of the receiving device according to the first embodiment.
Figure 13:
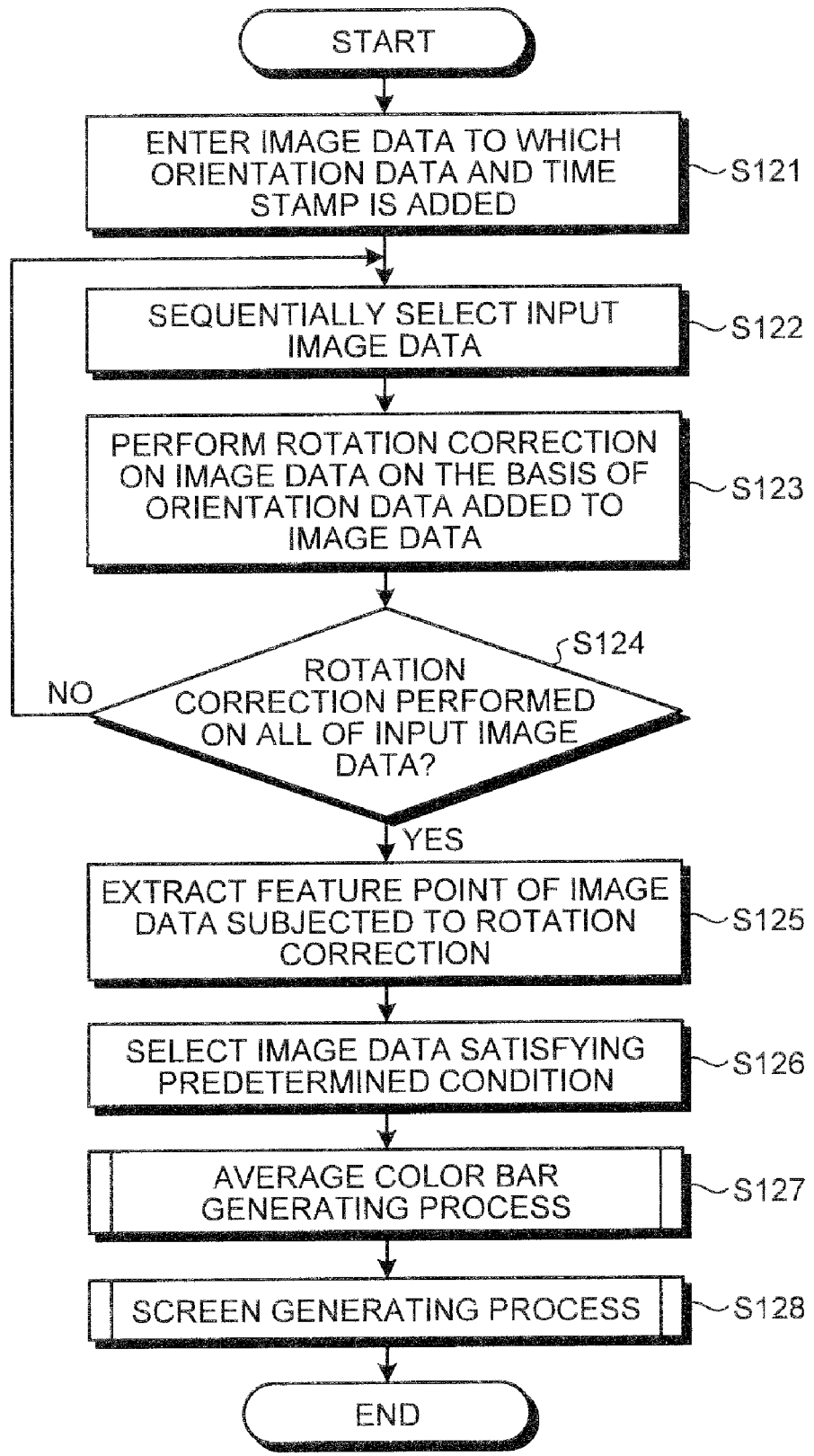
FIG. 13 is a flowchart showing an example of outline operation of the display device according to the first embodiment.

FIG. 11 is a flowchart showing an example of schematic operation of the capsule medical device 10 according to the first embodiment. FIG. 12 is a flowchart showing an example of schematic operation of the receiving device 130 according to the first embodiment. FIG. 13 is a flowchart showing an example of schematic operation of the display device 150 according to the first embodiment.

As shown in FIG. 11, after startup, the capsule medical device 10 executes imaging operation periodically (for example, at time T (=0.5 second) intervals), thereby obtaining image data (steps S101 and S102). Subsequently, the capsule medical device 10 obtains time at which the image data is obtained (step S103) and adds the time as a time stamp to the image data (step S104). The capsule medical device 10 transmits, as a wireless signal, the image data to which the time stamp is added (step S105), and returns to the step S101. By such operation, image data is periodically transmitted by radio from the capsule medical device 10 to the receiving device 130. The operation of the capsule medical device 10 shown in FIG. 11 is continued until no power remains in the battery 16 in the capsule medical device 10.

On the other hand, as shown in FIG. 12, the receiving device 130, for example, always monitors whether image data is received from the capsule medical device 10 (No in step S111). In the case where image data is received (Yes in step S111), the receiving device 130 estimates spatial spread of an electromagnetic wave (electric field distribution) from the phase of the electromagnetic wave (sign for orientation detection) in each of the antennas 120 detected by the transmitting/receiving circuit 131 at the time of reception of the image data in step S111 and the strength in each of the antennas 120 detected by the RSSI circuit 131a, specifies the orientation with respect to the reference direction Ds of the capsule medical device 10 (that is, the orientation with respect to the reference direction Ds, of the specified direction Ui) in the CPU 133, and generates it as orientation data (step S112).

Next, the receiving device 130 adds the orientation data generated in the CPU 133 to the image data received in step S111 (step S113) and, as a result, either stores the image data to which the orientation data and the time stamp are added from the interface 137 into the portable recording medium 140 or transmits the image data from the interface 137 to the display device 150 via the communication cable 159 (step S114). After that, the receiving device 130 determines whether the operation is continued, for example, whether an operation end instruction is received from the operation unit 135 (step S115). In the case of continuing the operation (Yes in step S115), the receiving device 130 returns to step S111 and waits for reception of next image data. On the other hand, in the case where the operation is not continued (No in step S115), the operation is finished.

As shown in FIG. 13, when the display device 150 receives one or more pieces of image data from the receiving device 130 via the portable recording medium 140 or the communication cable 159 (step S121), the display device 150 inputs the image data to the image processing unit 154. The image processing unit 154 sequentially selects the input image data one by one (step S122) and inputs the image data or the orientation data added to the image data to the rotation correcting unit 154a. The rotation correcting unit 154a two-dimensionally rotation-corrects the image data on the display face by using the orientation data added to the input image data, thereby making the reference direction Ds of the image data coincide with the upward direction Du of the screen (step S123). The operations in step S122 and S123 are repeated (No in step S124) until the rotation correction is performed on all of the image data which is input in step S121 (Yes in step S124). The image data subjected to the rotation correction is sequentially supplied from the rotation correcting unit 154a to the feature point extracting unit 154b and the image selecting unit 154c.

The feature point extracting unit 154b to which the image data subjected to the rotation correction is supplied extracts a feature point included in the image data (step S125). The extracted feature point is supplied to the image selecting unit 154c.

The image selecting unit 154c selects image data satisfying a predetermined condition from a plurality of pieces of image data on the basis of the image data subjected to the rotation correction supplied from the rotation correcting unit 154a as a result of step S124 and the feature point extraction result supplied from the feature point extracting unit 154b as a result of step S125 (step S126). For example, the image selecting unit 154c selects image data having a feature point largely different from a feature point of image data of last time. The selected image data is input to each of the average color bar generating unit 154d and the screen generating unit 154e. A threshold is, for example, a value for selecting image data in which a scene change occurs and image data including a peculiar shape. The threshold can be derived in advance by experience, experiment, simulation, or the like.

The average color bar generating unit 154d generates an image of the average color bar 60 by which a schematic image of each image can be seen at a glance along time series from all of the selected image data subjected to the rotation correction (average color bar generating process: step S127). An example of the rotation correction in step S123 and an example of the average color bar 60 generated in step S127 will be described specifically later by using FIGS. 14 and 15. The generated image of the average color bar 60 is input to the screen generating unit 154e.

The screen generating unit 154e to which the image of the average color bar 60 and the selected image data is input executes a screen generating process of generating a GUI screen as shown in FIG. 8 by using the image of the average color bar 60 and the selected image data (step S128) and, after that, finishes the process. The generated GUI screen is input to the display unit 155 via the control unit 151 and displayed to the observer. As a result, the GUI function using the GUI screen and the input unit 156 is provided to the observer.

Figure 14:
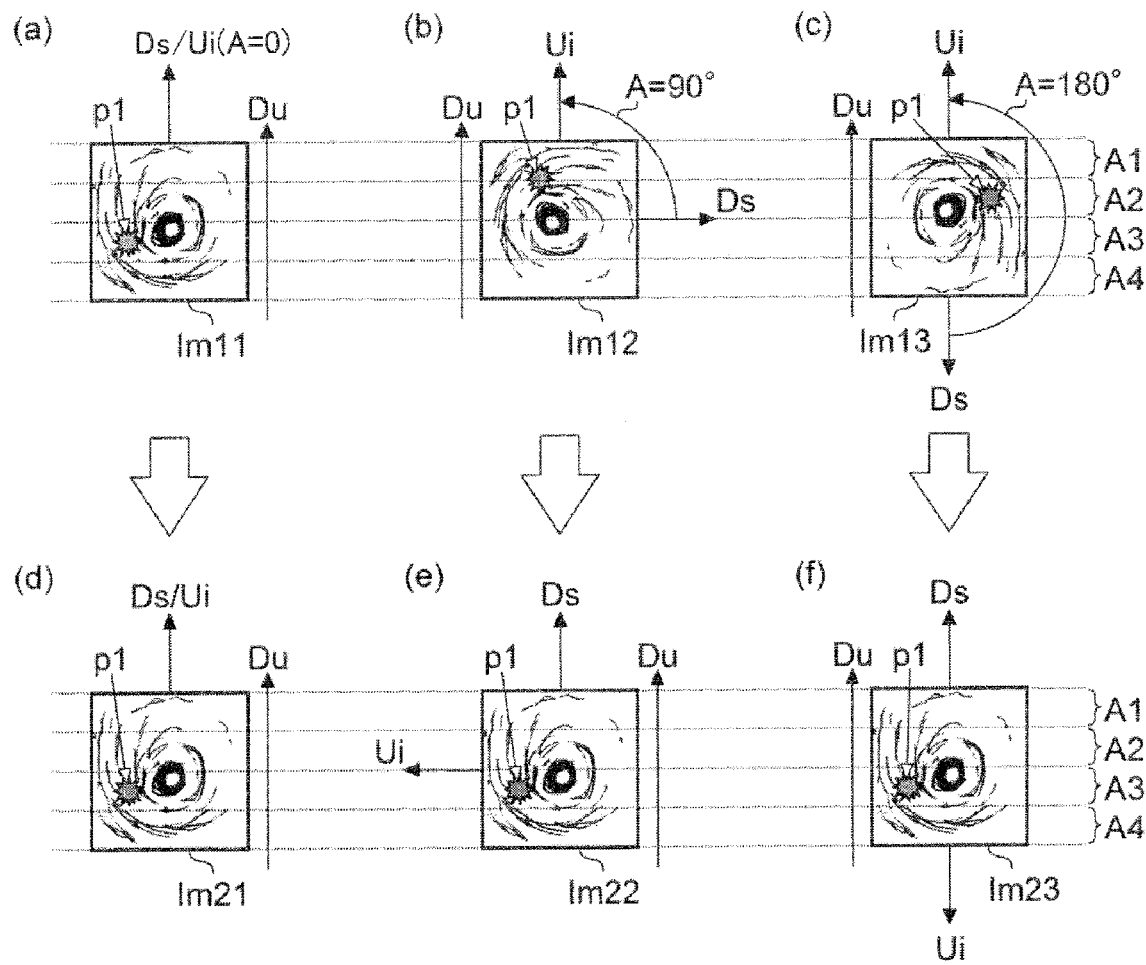
FIG. 14 is a diagram for explaining correction of rotation of image data in step S123 in FIG. 13.

Using FIGS. 14 and 15, an example of the rotation correction in step S123 and an example of the average color bar 60 generated in step S127 will be described. FIG. 14 is a diagram for explaining the rotation correction of image data in step S123 in FIG. 13. FIG. 15 is a diagram showing an example of the average color bar 60 generated by using the image data subjected to the rotation correction in step S127 in FIG. 13. Image data Im11 to Im13 shown in (a) to (c) in FIG. 14 corresponds to the image data Im11 to Im13 shown in FIG. 9.

As shown in (a) in FIG. 14, in the image data Im11 obtained at the first imaging timing, the specified direction Ui and the reference direction Ds coincide with each other. Consequently, the rotation amount (correction amount) A at the time of the rotation correction on the image data Im11 is 0°. As shown in (b) in FIG. 14, in the image data Im12 obtained at the second imaging timing, the angle of the specified direction Ui with respect to the reference direction Ds is 90°. Therefore, the rotation amount (correction amount) A at the time of the rotation correction on the image data Im12 is 90°. Further, as shown in (c) in FIG. 14, in the image data Im13 obtained at the third imaging timing, the angle of the specified direction Ui with respect to the reference direction Ds is 180°. Therefore, the rotation amount (correction amount) A at the time of the rotation correction on the image data Im13 is 180°. In the rotation correcting unit 154a and step S123, by performing the rotation correction on the image data by using the rotation amount (correction amount) A obtained as described above, as shown in (d) to (f) in FIG. 14, the reference direction Ds of each of image data Im21 to Im23 is made coincide with the upward direction Du of the screen.

As a result of the rotation correction as described above, as illustrated in (d) to (f) in FIG. 14, the same part p1 in image data Im21 to Im23 is included in the same division region A3. Consequently, as shown in FIG. 15, the positions of regions P21 to P23 including the same part p1 in the average color bar 60 generated by using the image data Iran to Im23 subjected to the rotation correction can be aligned in the horizontal direction in the division region A3. (d) in FIG. 14 shows the image data Im21 obtained by rotation-correcting the image data Im11 of (a) in FIG. 14, (e) in FIG. 14 shows the image data Im22 obtained by rotation-correcting the image data Im12 of (b) in FIG. 14, and (f) in FIG. 14 shows the image data Im23 obtained by rotation-correcting the image data Im13 of (c) in FIG. 14.

In the first embodiment as described above, the orientations of a plurality of pieces of image data can be aligned by performing the rotation correction on image data on the basis of the orientation with respect to the reference direction Ds of the capsule medical device 10 at the time of imaging, so that the medical system 1 and the image processing method enabling reduced time and effort on diagnosis and improved accuracy of a diagnosis result can be realized.

Although the rotation correction on image data (refer to step S123 in FIG. 13) is executed in the display device 150 in the first embodiment, the invention is not limited to the case but can be variously modified by, for example, executing the rotation correction in the receiving device 130 or the like.
Modification 1-1

In the medical system 1 according to the first embodiment, the case using the electromagnetic wave generating source (antenna 15a) as the signal source has been described as an example. However, the invention is not limited to the case. A magnetic field generation source can be used as the signal source. In the following, this case will be described in detail as modification 1-1 of the first embodiment with reference to the drawings. In the following description, the same reference numerals are designated to components similar to those of the foregoing embodiment for simplification of explanation, and their description will not be repeated.

Figure 16:
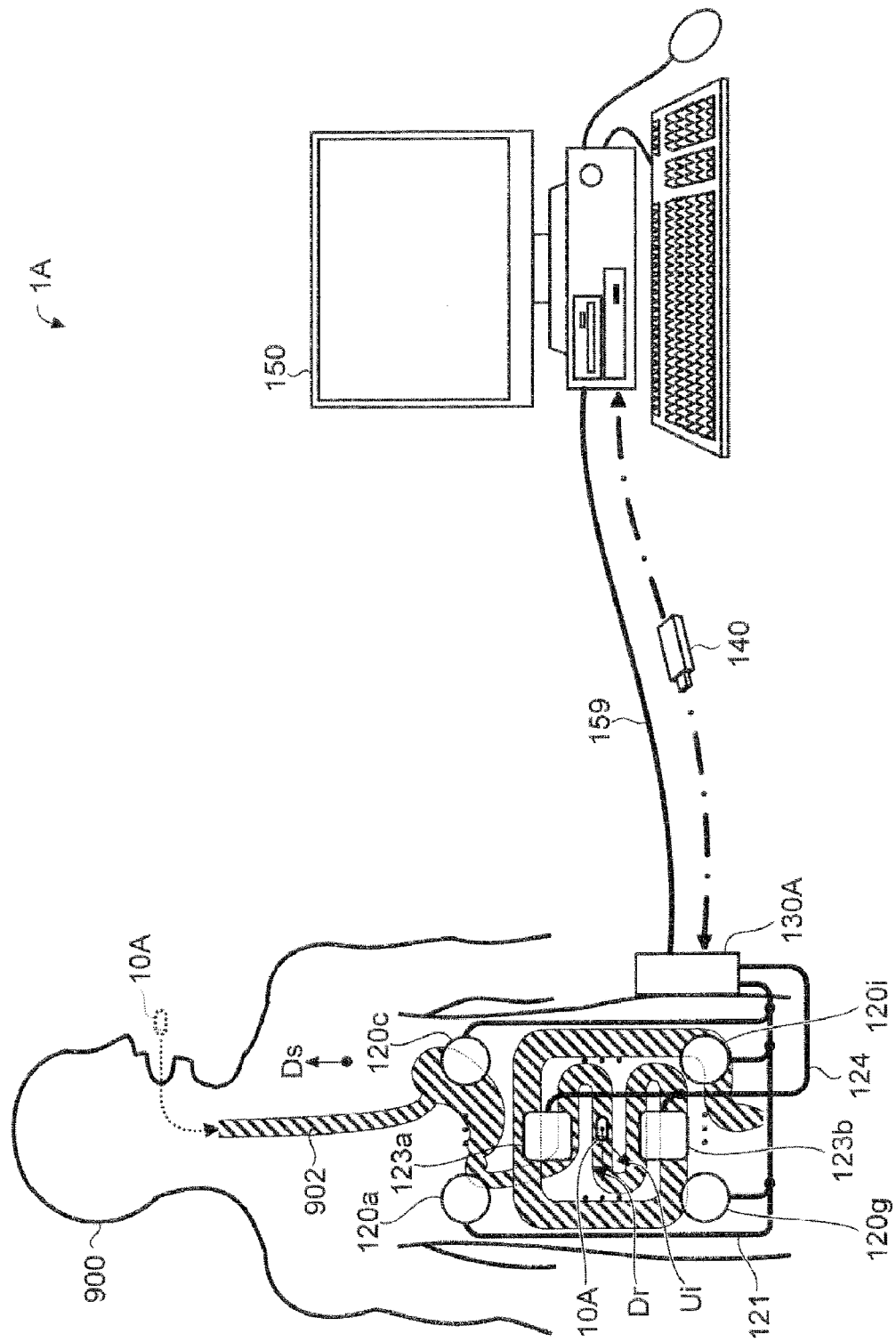
FIG. 16 is a schematic diagram showing a schematic configuration of a medical system according to modification 1-1 of the first embodiment.
Figure 17:
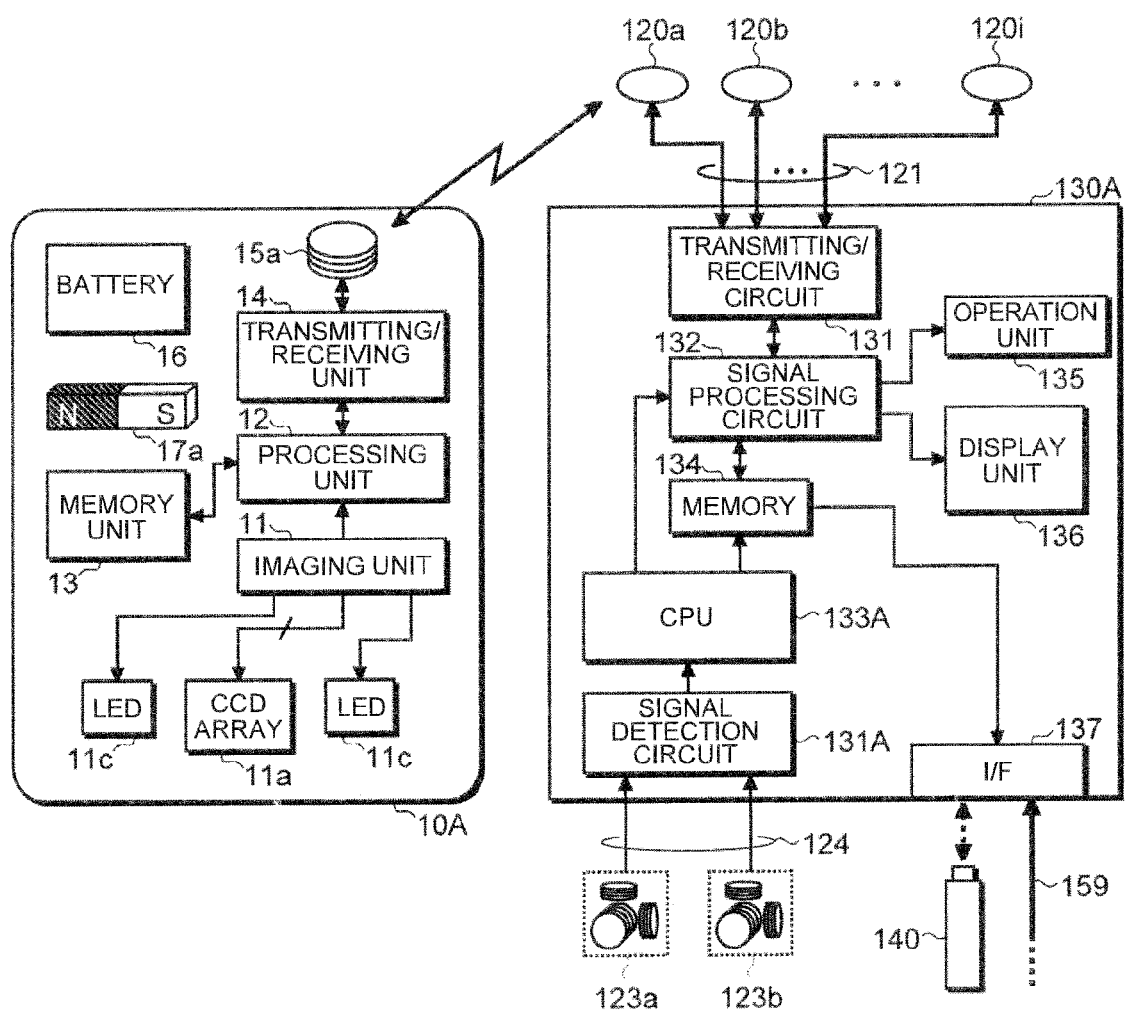
FIG. 17 is a block diagram showing a schematic configuration example of a capsule medical device and a receiving device according to the modification 1-1 of the first embodiment.

FIG. 16 is a schematic diagram showing a schematic configuration of a medical system 1A according to the modification 1-1. FIG. 17 is a block diagram showing a schematic configuration example of a capsule medical device 10A and a receiving device 130A according to the modification 1-1.

As shown in FIG. 16, in the medical system 1A, in comparison with the medical system 1 shown in FIG. 1, the capsule medical device 10 is replaced with the capsule medical device 10A, and the receiving device 130 is replaced with the receiving device 130A. Further, in the medical system 1A, the receiving device 130 has magnetic sensors 123a and 123b connected to the receiving device 130A via a cable 124.

The capsule medical device 10A has, as shown in FIG. 17, a permanent magnet 17a in addition to a configuration similar to that of the capsule medical device 10 shown in FIG. 5.

The permanent magnet 17a is magnetic field forming means for forming a magnetic field which reaches the outside of the subject 900 and functions as a signal source generating a sign for orientation detection (the magnetic field in the example) for specifying the orientation of the capsule medical device 10A (that is, tilt of the specified direction Ui) with respect to the reference direction Ds. The permanent magnet 17a is fixed to the casing 18. The invention is not limited to the permanent magnet 17a but can be applied to anything as long as it can form a magnetic field reaching the outside of the subject 900, such as a coil.

Preferably, the permanent magnet 17a is fixed in the casing 18 so that the direction of the magnetic pole of the permanent magnet 17a coincides with the orientation of the specified direction Ui. With the configuration, the orientation with respect to the reference direction Ds of the permanent magnet 17a can be directly used as the orientation with respect to the reference direction Ds of the specified direction Ui, so that the process in the receiving device 130A which will be described later can be lessened.

On the other hand, as shown in FIG. 17, the receiving device 130A has, in addition to a configuration similar to the configuration of the receiving device 130 shown in FIG. 5, the plurality of magnetic sensors 123a and 123b fixed to the surface (for example, the jacket 122 or the like) of the subject 900 and a signal detecting circuit 131A executing a predetermined signal process on a detection signal read from the magnetic sensors 123a and 123b.

Each of the magnetic sensors 123a and 123b is, for example, a triaxial magnetic sensor in which three coils whose center axes correspond to the x axis, y axis, and z axis are combined, and functions as an observation point as magnetic field detecting means for observing a sign for orientation detection (a magnetic field in the embodiment) generated from the permanent magnet 17a as a signal source. The invention, however, is not limited to the sensor but a triaxial magnetic sensor made by, for example, a magnetoresistive element, a magnetic impedance element (MI element), a hall element, or the like can be also employed.

The number of the magnetic sensors 123a and 123b, an arrangement pattern, and an object to which the magnetic sensors 123a and 123b can be variously modified as long as the number and the arrangement pattern by which a CPU 133A can estimate/specify the spatial spread (magnetic field distribution) of the magnetic field formed by the permanent magnet 17a of the capsule medical device 10A introduced in the subject 900 and the fixation object which can be substantially fixed to the subject 900 are used. In the description, the number of the magnetic sensors 123a and 123b is at least two.

A potential change detected by the magnetic sensors 123a and 123b is read as a detection signal by the signal detection circuit 131A of the receiving device 130A via the cable 124. The signal detection circuit 131A performs a process such as fast Fourier transformation (FFT) on the read signal and supplies the processed signal to the CPU 133A.

Like the CPU 133 in the foregoing first embodiment, the CPU 133A functions as orientation specifying means specifying the orientation of the capsule medical device 10A (that is, tilt of the specified direction Ui) with respect to the reference direction Ds from the strength and orientation of the sign (magnetic field) for orientation detection observed at the observation points (the magnetic sensors 123a and 123b). That is, the CPU 133A estimates the spatial spread of the magnetic field (magnetic field distribution) on the basis of the magnetic field strength of a detection signal, the orientation of a line of magnetic force, and the like in each of the magnetic sensors 123a and 123b supplied from the signal detection circuit 131A and specifies the orientation with respect to the reference direction Ds of the capsule medical device 10A (that is, the orientation with respect to the reference direction Ds of the specified direction Ui). In a manner similar to the foregoing embodiment, information of the orientation (orientation data) with respect to the reference direction Ds of the specified direction Ui specified by the CPU 133A is temporarily stored in association with image data received simultaneously or around the same time from the capsule medical device 10A into the memory 134. The strength and orientation of the magnetic field formed by the permanent magnet 17a can be detected by, for example, a change in the magnetic field distribution when the capsule medical device 10A (that is, the permanent magnet 17a) moves.

As described above, in the modification 1-1, using the permanent magnet 17a as the signal source and using the plurality of magnetic sensors 123a and 123b at observation points, the orientation data indicative of the orientation with respect to the reference direction Ds of the specified direction Ui is generated. The other configuration is similar to that of any of the foregoing embodiments (including their modifications).

Figure 18:
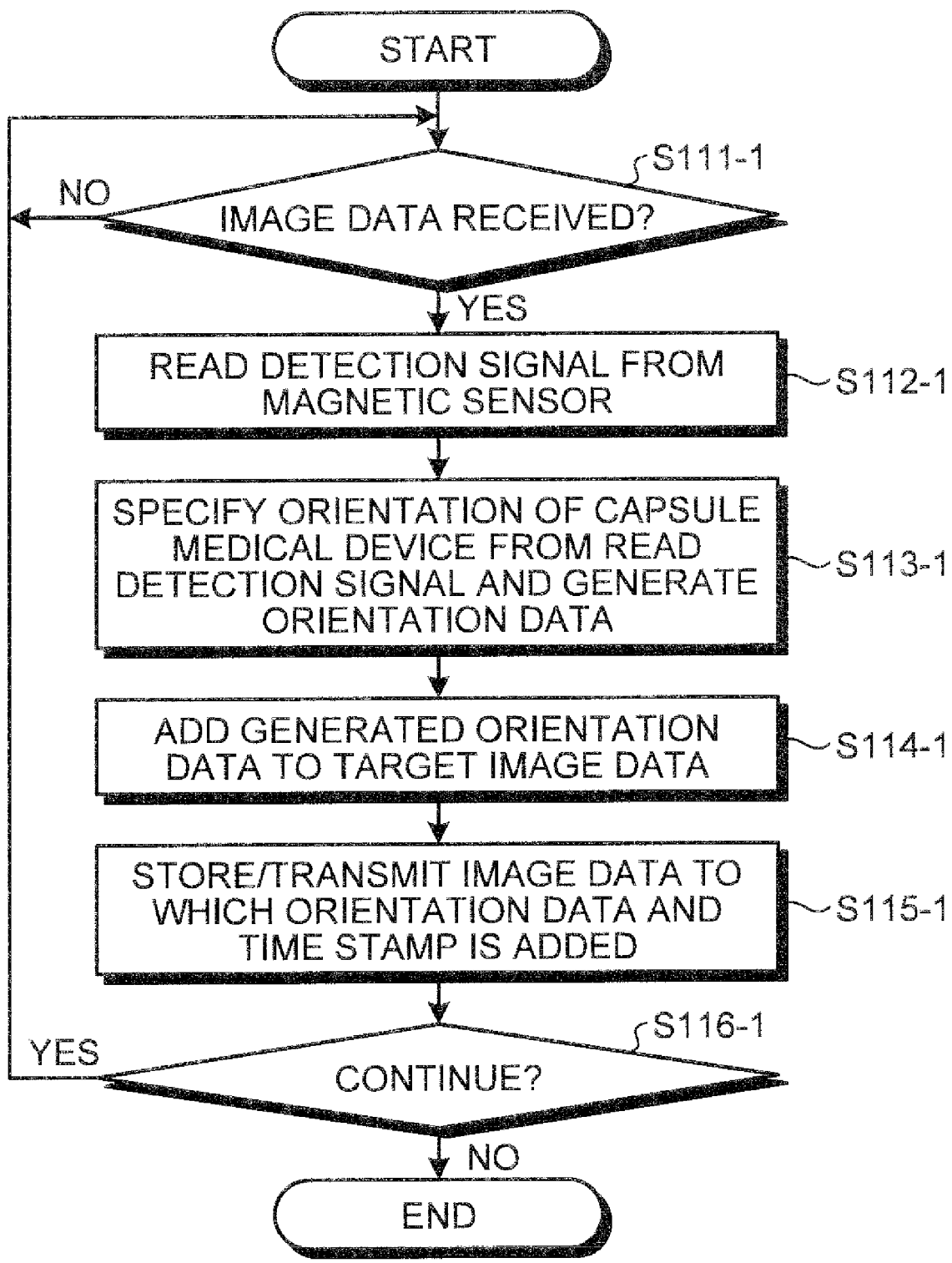
FIG. 18 is a flowchart showing an example of outline operation of the receiving device according to the modification 1-1 of the first embodiment.

Next, the operation of the medical system 1A according to the modification 1-1 will be described in detail with reference to the drawings. Since the operation of the capsule medical device 10A and the display device 150 in the modification 1-1 is similar to that of the first embodiment, in the description, the operation of the receiving device 130A will be described below. FIG. 18 is a flowchart showing an example of outline operation of the receiving device 130A according to the modification 1-1.

As shown in FIG. 18, the receiving device 130A, for example, always monitors whether image data is received from the capsule medical device 10A (No in step S111-1). In the case where image data is received (Yes in step S111-1), the receiving device 130A reads detection signals from the magnetic sensors 123a and 123b by using the signal detection circuit 131A, executes a predetermined signal process (step S112-1), subsequently, estimates spatial spread of a magnetic field (magnetic field distribution) from the magnetic field strength of the detection signal subjected to the signal process, the orientation of the line of magnetic force, and the like, specifies the orientation with respect to the reference direction Ds of the capsule medical device 10A (that is, orientation with respect to the reference direction Ds of the specified direction Ui), and generates it as orientation data (step S113-1).

Next, like the operation described with reference to FIG. 12 in the first embodiment, the receiving device 130A adds the orientation data generated in the CPU 133A to the image data received in step S111-1 (step S114-1) and, as a result, either stores the image data to which the orientation data and the time stamp are added from the interface 137 into the portable recording medium 140 or transmits the image data from the interface 137 to the display device 150 via the communication cable 159 (step S115-1). After that, the receiving device 130A determines whether the operation is continued, for example, whether an operation end instruction is received from the operation unit 135 (step S116-1). In the case of continuing the operation (Yes in step S116-1), the receiving device 130A returns to step S111-1 and waits for reception of next image data. On the other hand, in the case where the operation is not continued (No in step S116-1), the operation is finished.

With the configuration and operation as described above, in the modification 1-1, in a manner similar to the first embodiment, the orientations of a plurality of pieces of image data can be aligned by performing the rotation correction on image data on the basis of the orientation with respect to the reference direction Ds of the capsule medical device 10A at the time of imaging, so that the medical system 10A and the image processing method enabling reduced time and effort on diagnosis and improved accuracy of a diagnosis result can be realized.

Figure 19:
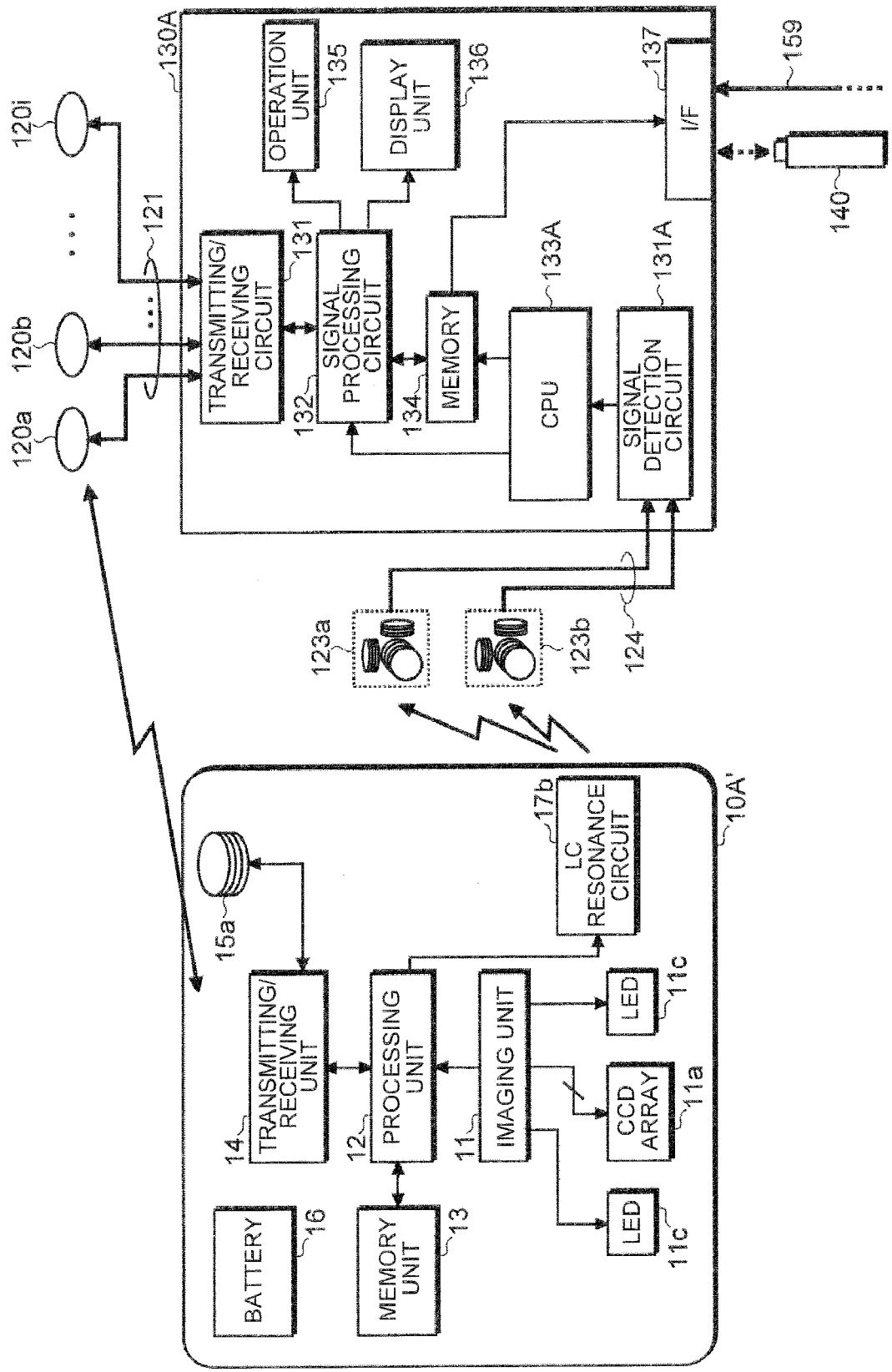
FIG. 19 is a block diagram showing a schematic configuration example of a capsule medical device and a receiving device according to another example of the modification 1-1 of the first embodiment.

Although the case of using the permanent magnet 17a as a signal source has been described as an example in the modification 1-1, the invention is not limited to the case but can use as a signal source, for example, as shown in a capsule medical device 10A' of FIG. 19, an LC resonance circuit 17b (magnetic field forming means) generating an induced magnetic field at a predetermined resonance frequency spontaneously or when induced. FIG. 19 is a block diagram showing a schematic configuration example of the capsule medical device 10A' and the receiving device 130A according to another example of the modification 1-1.

For example, in the case of generating the induced magnetic field spontaneously (this will be called an active method), a current signal of an almost resonance frequency is supplied from, for example, the processing unit 12 (signal generating means) to the LC resonance circuit 17b. On the other hand, for example, in the case of generating an induced magnetic field by being induced by an external magnetic field (this will be called a passive method), a magnetic field (drive magnetic field) of a frequency almost equal to the resonance frequency of the LC resonance circuit 17b is generated in a detection space in which the capsule medical device 10A is introduced. The CPU 133A specifies the orientation with respect to the reference direction Ds of the capsule medical device 10A' on the basis of the orientation and strength of the magnetic field indicated by a detection signal read from each of the magnetic sensors 123a and 123b (that is, the orientation and strength of the magnetic field in the position of each of the magnetic sensors 123a and 123b) and generates orientation data from the specified orientation.

Modification 1-2

As the signal source in the first embodiment, an ultrasound generation source can be used. In the following, this case will be described in detail as modification 1-2 of the first embodiment with reference to the drawings. In the following description, the same reference numerals are designated to components similar to those of the foregoing embodiment or its modification for simplification of explanation, and their description will not be repeated.

Figure 20:
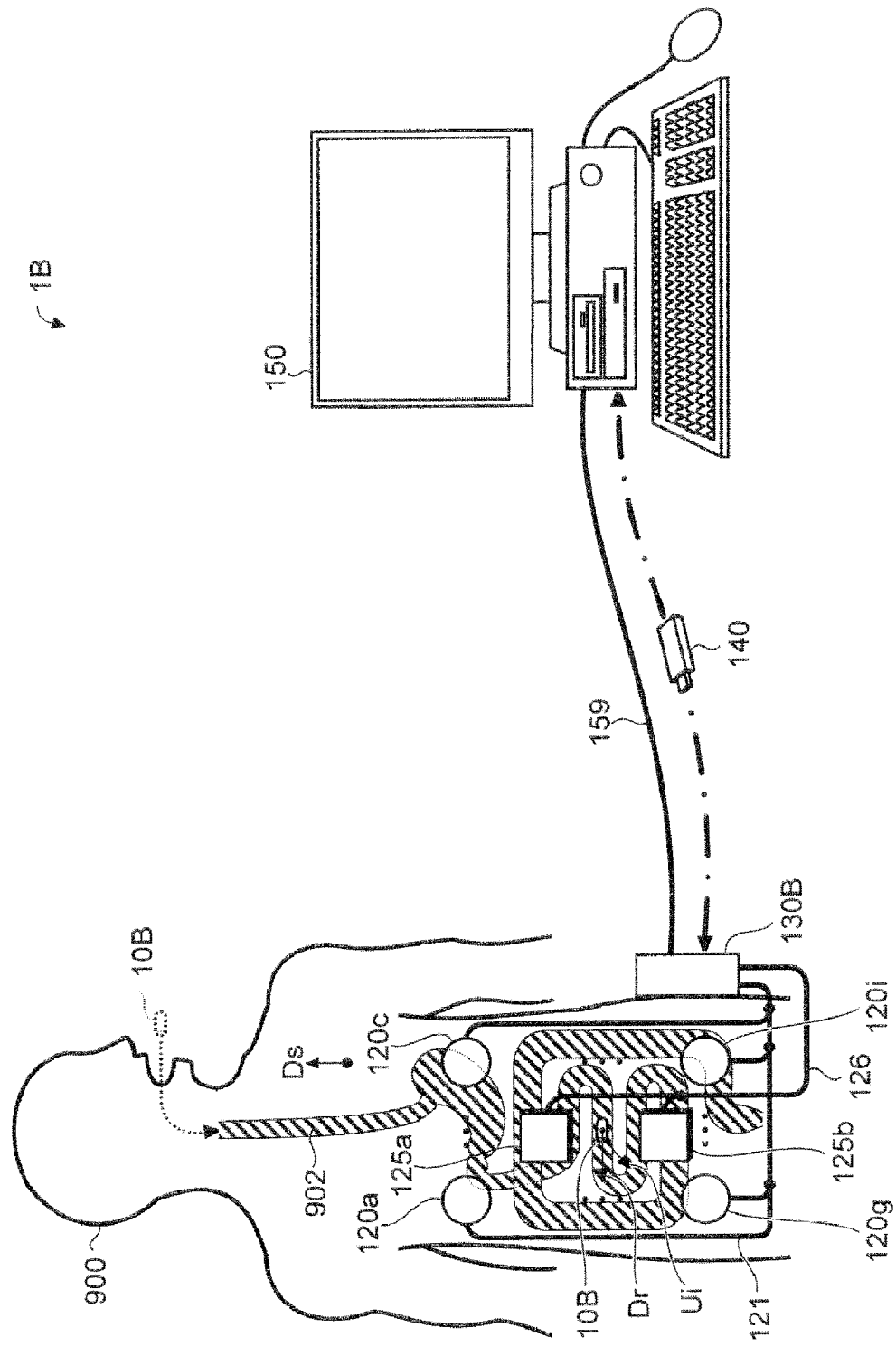
FIG. 20 is a schematic diagram showing a schematic configuration of a medical system according to modification 1-2 of the first embodiment.
Figure 21:
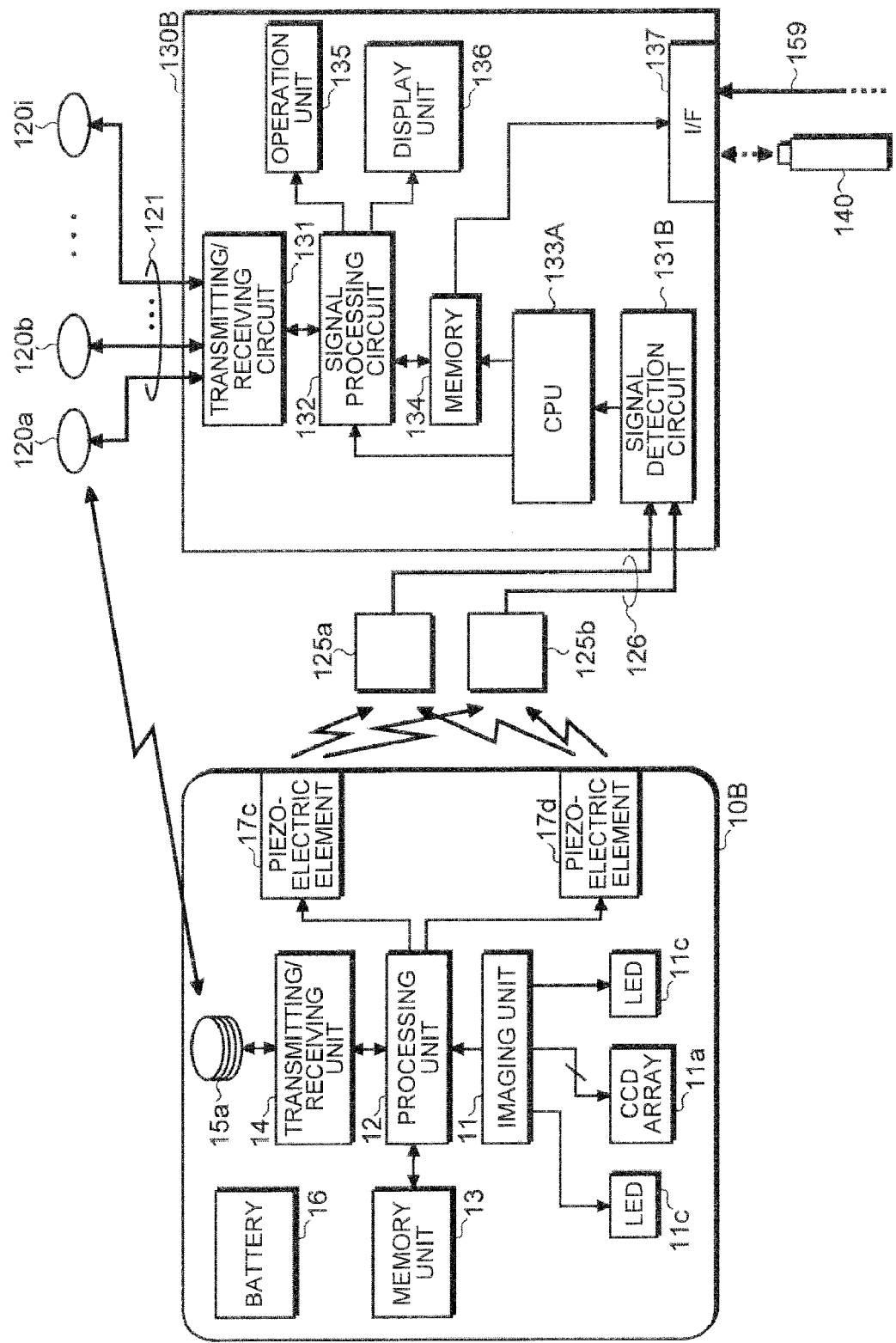
FIG. 21 is a block diagram showing a schematic configuration example of a capsule medical device and a receiving device according to the modification 1-2 of the first embodiment.

FIG. 20 is a schematic diagram showing a schematic configuration of a medical system 1B according to the modification 1-2. FIG. 21 is a block diagram showing a schematic configuration example of a capsule medical device 10B and a receiving device 130B according to the modification 1-2.

As shown in FIG. 20, in the medical system 1B, in comparison with the medical system 1 shown in FIG. 1, the capsule medical device 10 is replaced with the capsule medical device 10B, and the receiving device 130 is replaced with the receiving device 130B. Further, in the medical system 1B, the receiving device 130B is provided with acoustic sensors 125a and 125b connected to the receiving device 130B via a cable 126.

The capsule medical device 10B has, as shown in FIG. 21, at least two piezoelectric elements 17c and 17d in addition to a configuration similar to that of the capsule medical device 10 shown in FIG. 5.

The piezoelectric elements 17c and 17d are ultrasound generating means for generating an ultrasound wave which propagates the inside of the subject 900 and reaches the outside surface, and functions as a signal source generating a sign for orientation detection (the ultrasound wave in the example) for specifying the orientation of the capsule medical device 10B (that is, tilt of the specified direction Ui) with respect to the reference direction Ds.

Each of the piezoelectric elements 17c and 17d is fixed to the casing 18 so that a part of it is exposed to the outside of the casing 18 while maintaining water-tightness of the casing 18. The invention is not limited to the piezoelectric elements 17c and 17d but can be applied to anything as long as it can serve as an ultrasound source.

Preferably, the piezoelectric elements 17c and 17d are arranged in a state where they are fixed in the casing 18 so as to coincide with the orientation of the specified direction Ui. With the configuration, the orientation with respect to the reference direction Ds of the arrangement direction of the piezoelectric elements 17c and 17d can be directly used as the orientation with respect to the reference direction Ds of the specified direction Ui, so that the process in the receiving device 130B which will be described later can be lessened.

On the other hand, as shown in FIG. 21, the receiving device 130B has, in addition to a configuration similar to the configuration of the receiving device 130 shown in FIG. 5, the plurality of acoustic sensors 125a and 125b fixed to the surface (for example, the jacket 122 or the like) of the subject 900 and a signal detecting circuit 131B executing a predetermined signal process on a detection signal read from the acoustic sensors 125a and 125b.

Each of the acoustic sensors 125a and 125b is constructed by using, for example, a microphone and functions as an observation point as ultrasound detecting means for observing a sign for orientation detection (an ultrasound wave in the embodiment) generated from the plurality of piezoelectric elements 17c and 17d as a signal source. The invention, however, is not limited to the sensors but, for example, a piezoelectric element or the like may be used.

The number of the acoustic sensors 125a and 125b, an arrangement pattern, and an object to which the acoustic sensors 125a and 125b are fixed can be variously modified as long as the number and the arrangement pattern by which a CPU 133B can estimate/specify the orientation of the capsule medical device 10B from the strength and phase at the plurality of observation points of ultrasound waves (the acoustic sensors 125a and 125b) generated by the piezoelectric elements 17c and 17d of the capsule medical device 10B introduced in the subject 900 and the fixation object which can be substantially fixed to the subject 900 are used. In the description, the number of the acoustic sensors 125a and 125b is at least two.

A potential change which occurs in the acoustic sensors 125a and 125b is read as a detection signal by the signal detection circuit 131B of the receiving device 130B via the cable 126. The signal detection circuit 131B performs a process such as fast Fourier transformation (FFT) on the read signal and supplies the processed signal to the CPU 133B.

Like the CPU 133 in the foregoing first embodiment, the CPU 133B functions as orientation specifying means specifying the orientation of the capsule medical device 10B (that is, tilt of the specified direction Ui) with respect to the reference direction Ds from the strength and phase of the sign (ultrasound wave) for orientation detection observed at the observation points (the acoustic sensors 125a and 125b). That is, the CPU 133B estimates the spatial spread of the ultrasound wave (ultrasound distribution) on the basis of the phase, strength, and the like of a detection signal in each of the acoustic sensors 125a and 125b supplied from the signal detection circuit 131B and specifies the orientation with respect to the reference direction Ds of the capsule medical device 10B (that is, the orientation with respect to the reference direction Ds of the specified direction Ui). In a manner similar to the foregoing embodiment, information of the orientation (orientation data) with respect to the reference direction Ds of the specified direction Ui specified by the CPU 133B is temporarily stored in association with image data received simultaneously or around the same time from the capsule medical device 10B into the memory 134.

As described above, in the modification 1-2, using the plurality of piezoelectric elements 17c and 17d as the signal source and using the plurality of acoustic sensors 125a and 125b at observation points, the orientation data indicative of the orientation with respect to the reference direction Ds of the specified direction Ui is generated. The other configuration is similar to that of any of the foregoing embodiments (including their modifications).

Figure 22:
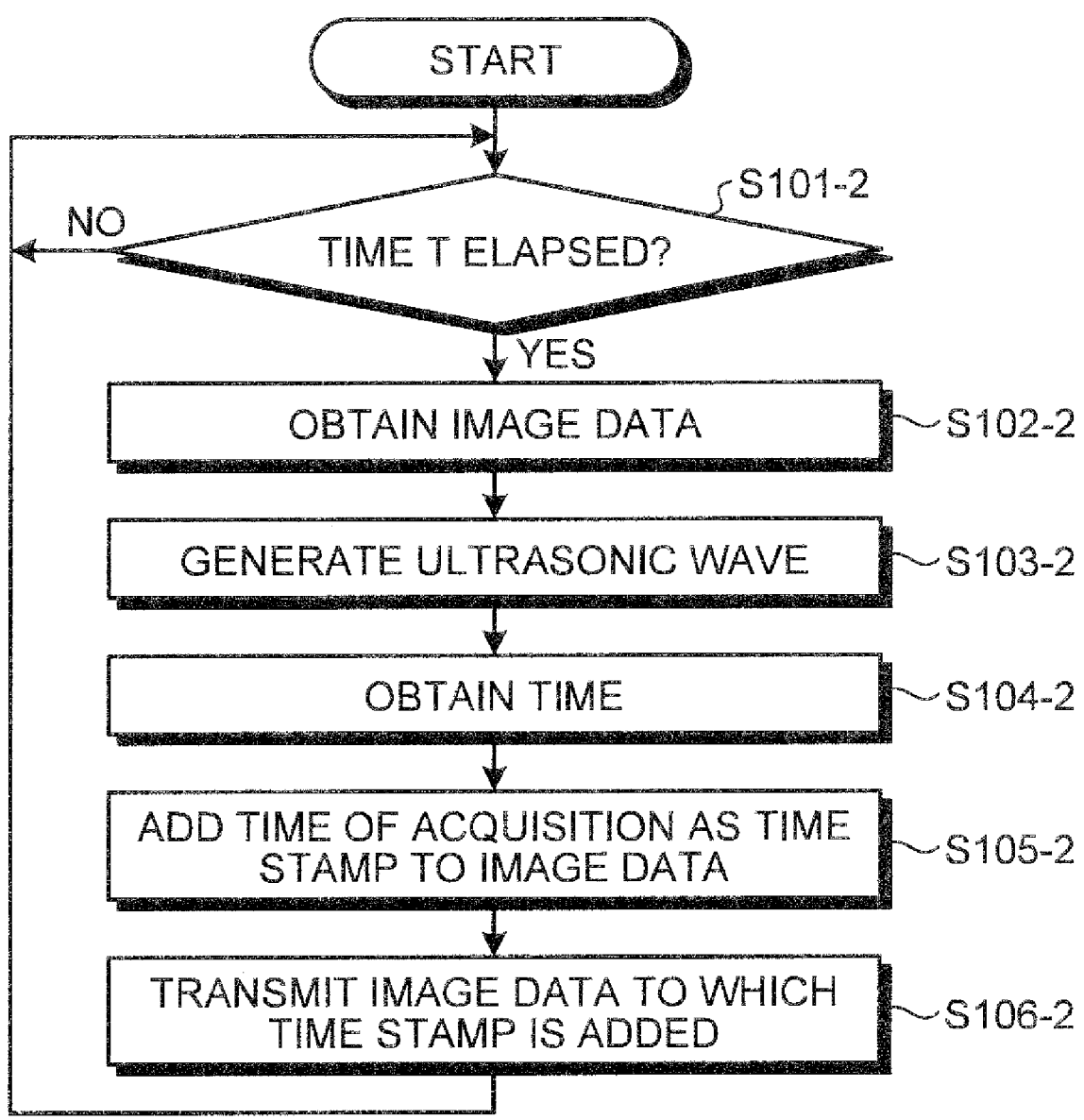
FIG. 22 is a flowchart showing an example of outline operation of the capsule medical device according to the modification 1-2 of the first embodiment.
Figure 23:
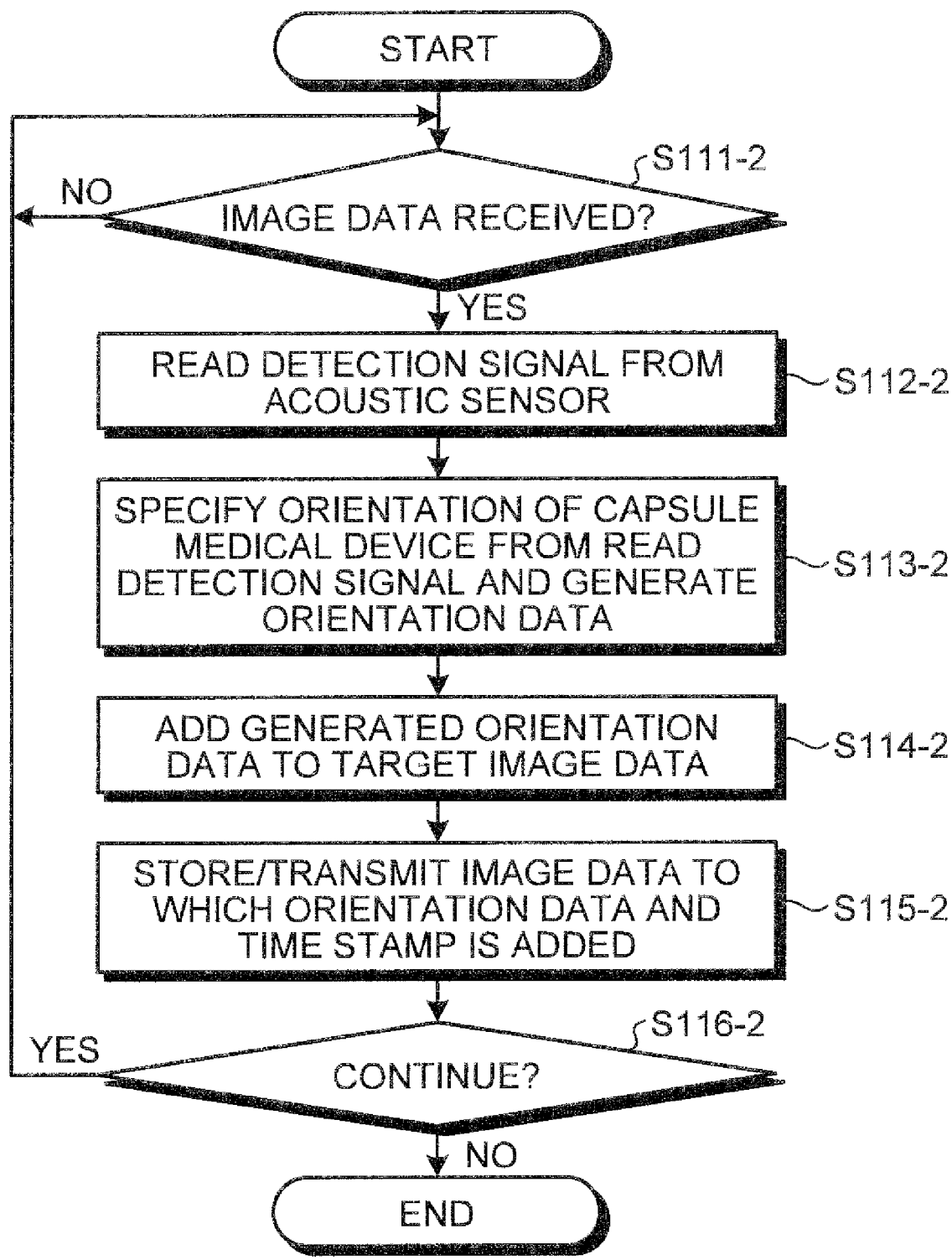
FIG. 23 is a flowchart showing an example of outline operation of the receiving device according to the modification 1-2 of the first embodiment.

Next, the operation of the medical system 1B according to the modification 1-2 will be described in detail with reference to the drawings. Since the operation of the display device 150 in the modification 1-2 is similar to that of the first embodiment, in the description, the operation of the capsule medical device 10B and the receiving device 130B will be described below. FIG. 22 is a flowchart showing an example of outline operation of the capsule medical device 10B according to the modification 1-2. FIG. 23 is a flowchart showing an example of outline operation of the receiving device 130B according to the modification 1-2.

As shown in FIG. 22, after startup, the capsule medical device 10B executes imaging operation periodically (for example, at intervals of time T (=0.5 second)), thereby obtaining image data (steps S101-2 to S102-2). The capsule medical device 10B generates a voltage signal of a predetermined frequency in the processing unit 12 and supplies it to the piezoelectric elements 17c and 17d, thereby generating ultrasonic waves from the piezoelectric elements 17c and 17d (step S103-2). Subsequently, the capsule medical device 10B obtains time at which the image data is obtained (step S104-2) and adds the time as a time stamp to the image data (step S105-2). The capsule medical device 10B transmits the image data to which the time stamp is added as a wireless signal (step S106-2) and returns to the step S101-2. By such operation, the image data is periodically transmitted by radio from the capsule medical device 10B to the receiving device 130B, and an ultrasonic wave for making the receiving device 130B specify the orientation of the capsule medical device 10B is generated. The operation of the capsule medical device 10B shown in FIG. 22 is continues until no power remains in the battery 16 in the capsule medical device 10B.

On the other hand, as shown in FIG. 23, the receiving device 130B, for example, always monitors whether image data is received from the capsule medical device 100 (No in step S111-2). In the case where image data is received (Yes in step S111-2), the receiving device 130B reads detection signals from the acoustic sensors 125a and 125b by using the signal detection circuit 131B, executes a predetermined signal process (step S112-2), subsequently, estimates spatial positions of the piezoelectric elements 17c and 17d as an ultrasound source from the phase, strength, and the like of the detection signals subjected to the signal process, specifies the orientation with respect to the reference direction Ds of the capsule medical device 10B (that is, orientation with respect to the reference direction Ds of the specified direction Ui) in the CPU 1330, and generates it as orientation data (step S113-2).

Next, like the operation described with reference to FIG. 12 in the first embodiment, the receiving device 130B adds the orientation data generated in the CPU 133B to the image data received in step S111-2 (step S114-2) and, as a result, either stores the image data to which the orientation data and the time stamp are added from the interface 137 into the portable recording medium 140 or transmits the image data from the interface 137 to the display device 150 via the communication cable 159 (step S115-2). After that, the receiving device 130B determines whether the operation is continued, for example, whether an operation end instruction is received from the operation unit 135 (step S116-2). In the case of continuing the operation (Yes in step S116-2), the receiving device 130B returns to step S111-2 and waits for reception of next image data. On the other hand, in the case where the operation is not continued (No in step S116-2), the operation is finished.

With the configuration and operation as described above, in the modification 1-2, in a manner similar to the first embodiment (and its modification), the orientations of a plurality of pieces of image data can be aligned by performing the rotation correction on image data on the basis of the orientation with respect to the reference direction Ds of the capsule medical device 10B at the time of imaging, so that the medical system 1B and the image processing method enabling reduced time and effort on diagnosis and improved accuracy of a diagnosis result can be realized.

Second Embodiment

Although the case of disposing the signal source (antenna 15a) in the capsule medical device 10 and fixing the observation points (antennas 120) on the outer surface of the subject 900 has been described as an example in the first embodiment, the invention is not limited to the case. The signal source can be fixed to the outer face of the subject 900 and the observation points can be disposed in the capsule medical device. In the following, the case will be described in detail as a second embodiment with reference to the drawings. In the following description, the same reference numerals are designated to components similar to those of the forgoing embodiment and its modifications for simplicity of explanation, and their detailed description will not be repeated.

Figure 24:
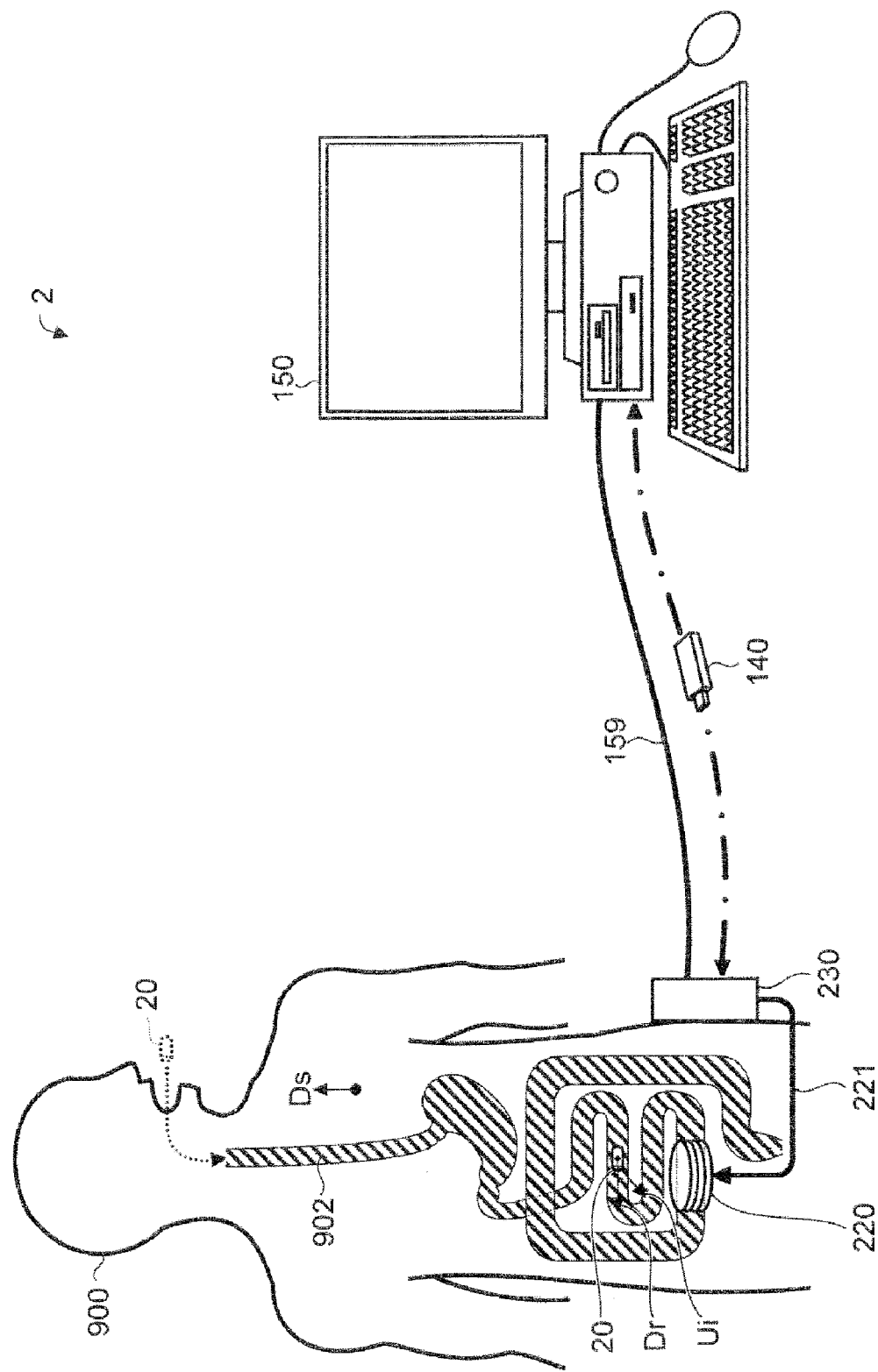
FIG. 24 is a schematic diagram showing a schematic configuration of a medical system according to a second embodiment.
Figure 25:
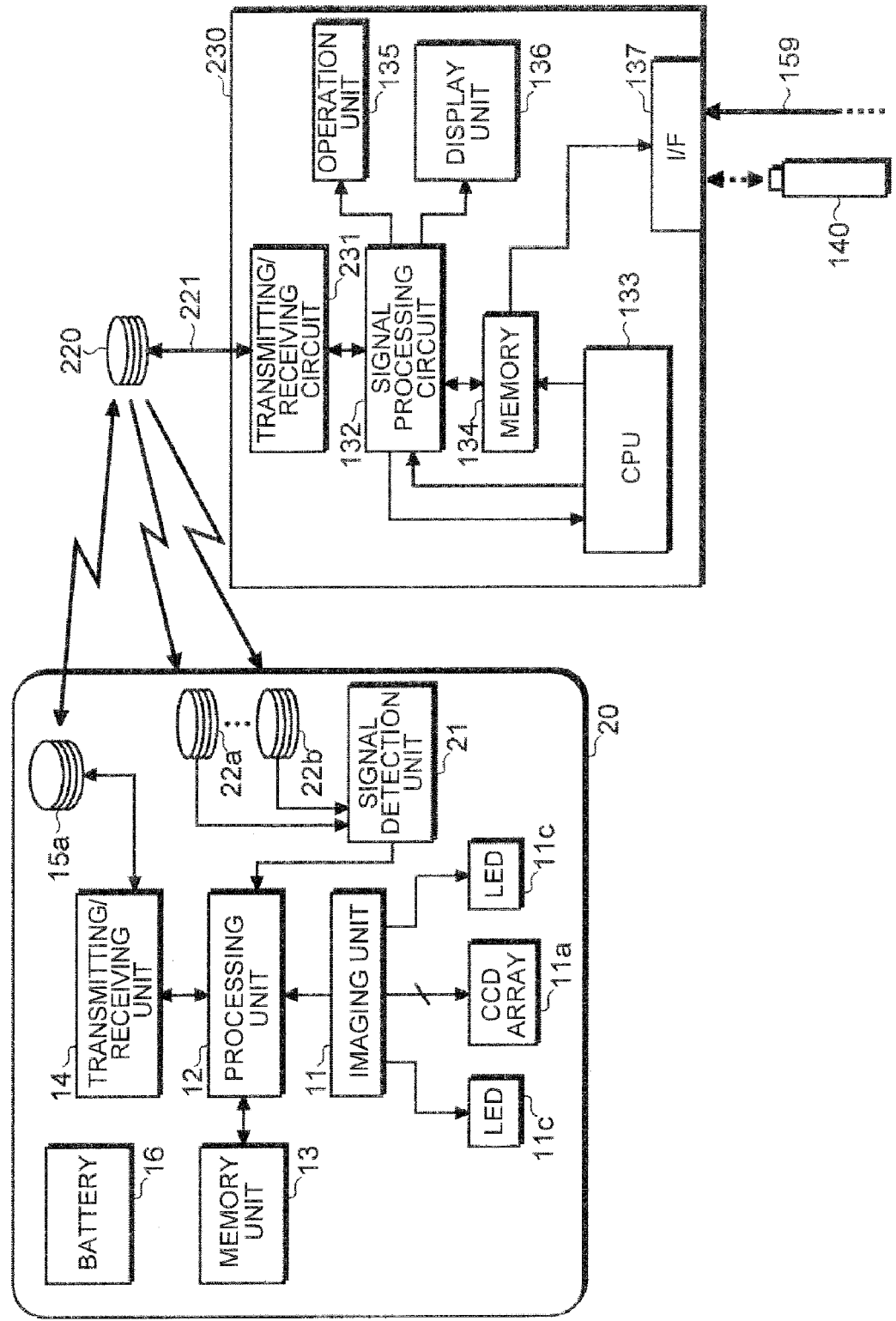
FIG. 25 is a block diagram showing a schematic configuration example of a capsule medical device and a receiving device according to the second embodiment.

FIG. 24 is a schematic diagram showing a schematic configuration of a medical system 2 according to the second embodiment. FIG. 25 is a block diagram showing an example of a schematic configuration of a capsule medical device 20 and a receiving device 230 according to the second embodiment.

As illustrated in FIG. 24, in the medical system 2, in comparison with the medical system 1 shown in FIG. 1, the capsule medical device 10 is replaced with the capsule medical device 20, and the receiving device 130 is replaced with the receiving device 230. Further, in the medical system 2, the antenna 120 (refer to FIG. 1) fixed to the surface of a subject 200 and the cable 121 are replaced with an antenna 220 and a cable 221, respectively.

As shown in FIG. 25, the capsule medical device 20 has, in addition to a configuration similar to that of the capsule medical device 10 shown in FIG. 5, antennas 22a and 22b and a signal detection unit 21 for detecting the phase and strength of the electromagnetic wave in the antennas 22a and 22b.

The antennas 22a and 22b are, for example, dipole antennas or loop antennas and function as observation points for observing a sign (electromagnetic wave) for orientation detection emitted from the antenna 220 as a signal source which will be described later. Preferably, the antennas 22a and 22b are disposed so as to be apart from each other as much as possible in the casing 18.

Preferably, the antennas 22a and 22b are arranged in a state where they are fixed in the casing 18 so as to coincide with the orientation of the specified direction Ui. With the arrangement, the orientation with respect to the reference direction Ds of the arrangement direction of the antennas 22a and 22b can be directly used as the orientation with respect to the reference direction Ds of the specified direction Ui, so that the process in the receiving device 230 which will be described later can be lessened. Further, the signal detection unit 21 includes, for example, an RSSI circuit (not shown) for detecting strength of the electromagnetic wave received in each of the antennas 22a and 22b.

The signal detection unit 21 executes, on a detection signal supplied from each of the antennas 22a and 22b, frequency separation and a predetermined process including a process of detecting the phase of an electromagnetic wave (a sign for orientation detection) between the antennas 22a and 22b and strength in each of the antennas 22a and 22b. The signal detection unit 21 adds, as signal detection data, the detected phase and strength in each of the antennas 22a and 22b to image data obtained at the same time or around the same time.

The signal detection data includes data corresponding to the phase of the electromagnetic wave (sign for orientation detection) between the antennas 120 detected by the transmitting/receiving circuit 131 in the receiving device 130 in the first embodiment and the strength of the electromagnetic wave (sign for orientation detection) observed at each antenna 120 detected by the RSSI circuit 131a of the transmitting/receiving circuit 131. To the image data, a time stamp is also added in a manner similar to the first embodiment. The image data to which the signal detection data and the time stamp are added is transmitted by radio from the antenna 15a to the receiving device 230 from the processing unit 12 via the transmitting/receiving unit 14.

On the other hand, in the receiving device 230, as shown in FIG. 25, in a configuration similar to the receiving device 130 shown in FIG. 5, the antenna 120 is replaced with the antenna 220, and the transmitting/receiving circuit 131 is replaced with a transmitting/receiving circuit 231.

Like the antenna 15a of the first embodiment, the antenna 220 is, for example, an antenna having directivity and functions as a signal source generating a sign for orientation detection (electric field in the example) for specifying the orientation of the capsule medical device 20 with respect to the reference direction Ds (that is, tilt of the specified direction Ui). In the second embodiment, a loop antenna is used as the antenna 220. However, the invention is not limited to the loop antenna. Any antenna is applicable as long as it can detect the orientation of the capsule medical device 20 with respect to the reference direction Ds on the basis of the phase and strength of the electromagnetic wave (sign for orientation detection) at the antennas 22a and 22b.

The antenna 220 having the directivity is fixed on the surface (for example, the jacket 122 or the like) of the subject 900. The antenna 220 is fixed to the outside surface of the subject 900 so that the center line of the loop of the antenna 220 (corresponding to the symmetrical axis of an electric field distribution shape of the electromagnetic wave generated by the antenna 15a) and the reference direction Ds become parallel to each other. Consequently, even in the case where the capsule medical device 20 rotates using the center line in the longitudinal direction as an axis, the orientation of the specified direction Ui of the capsule medical device 20 with respect to the reference direction Ds can be specified on the basis of the phase and strength of the electromagnetic wave received by the antennas 22a and 22b of the capsule medical device 20.

Like the transmitting/receiving circuit 131, the transmitting/receiving circuit 231 transmits/receives signals to/from the capsule medical device 20 via the antenna 220. As described above, the transmitting/receiving circuit 231 according to the second embodiment outputs an electromagnetic wave as a sign for orientation detection to the antenna 220 periodically (for example, twice or more per second).

The reception signal supplied from the antenna 220 to the transmitting/receiving circuit 231 is supplied to the signal processing circuit 132. In the second embodiment, as described above, the signal detection data is added to the image data received from the capsule medical device 20. The signal processing circuit 132 executes a predetermined process on the input signal (particularly, image data), specifies the signal detection data added to the image data, and supplies it to the CPU 133.

The CPU 133 functions as orientation specifying means estimating spatial spread (electric field distribution) of the electromagnetic wave (sign for orientation detection) from the phase of the electromagnetic wave (sign for orientation detection) at the antennas 22a and 22b included in the signal detection data and strength of the electromagnetic wave (sign for orientation detection) at the antennas 22a and 22b detected by the RSSI circuit of the signal detection unit 21 and specifying the orientation with respect to the reference direction Ds of the capsule medical device 20 (that is, orientation with respect to the reference direction Ds of the specified direction Ui). Since the method of estimating the electric field distribution is similar to that of the first embodiment, its detailed description will not be repeated.

As described above, in the second embodiment, the antenna 220 as a signal source is fixed to the outside surface of the subject 900, the antennas 22a and 22b as observation points are disposed in the capsule medical device 20, and orientation data indicative of the orientation with respect to the reference direction Ds of the specified direction Ui is generated on the basis of the electromagnetic wave from the antenna 220 observed at the antennas 22a and 22b. The other configuration is similar to any of those in the foregoing embodiments (including their modifications).

Figure 26:
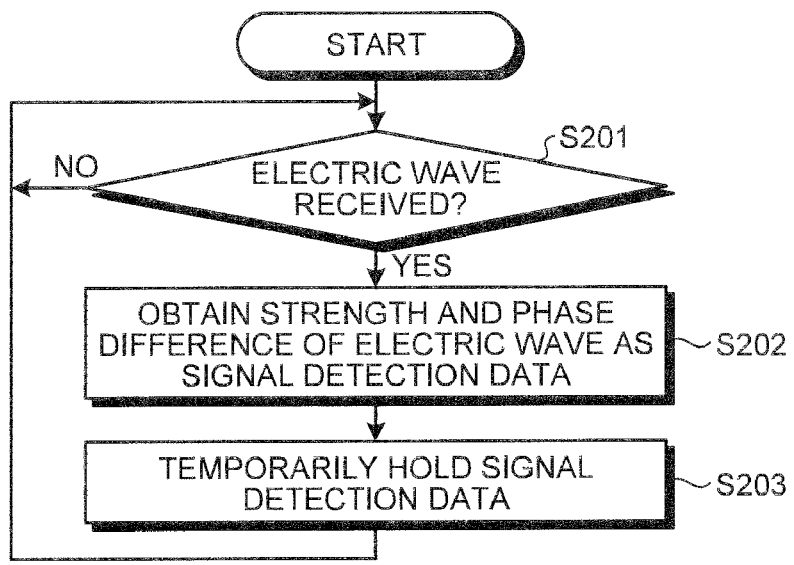
FIG. 26 is a flowchart showing an example (No. 1) of outline operation of the capsule medical device according to the second embodiment.
Figure 27:
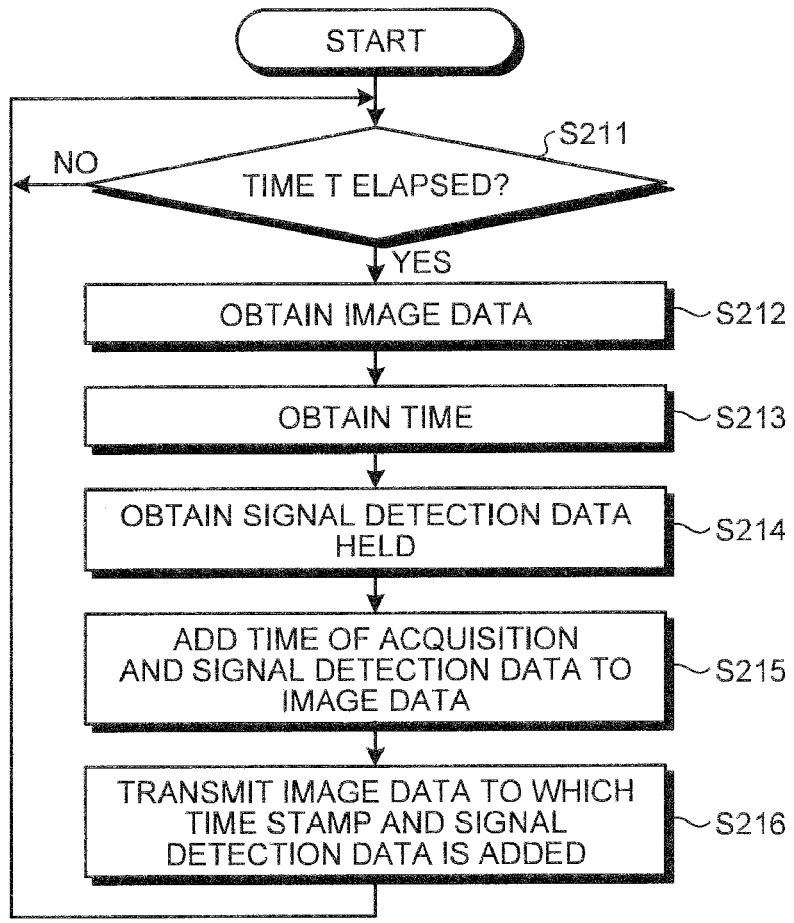
FIG. 27 is a flowchart showing an example (No. 2) outline operation of the capsule medical device according to the second embodiment.
Figure 28:
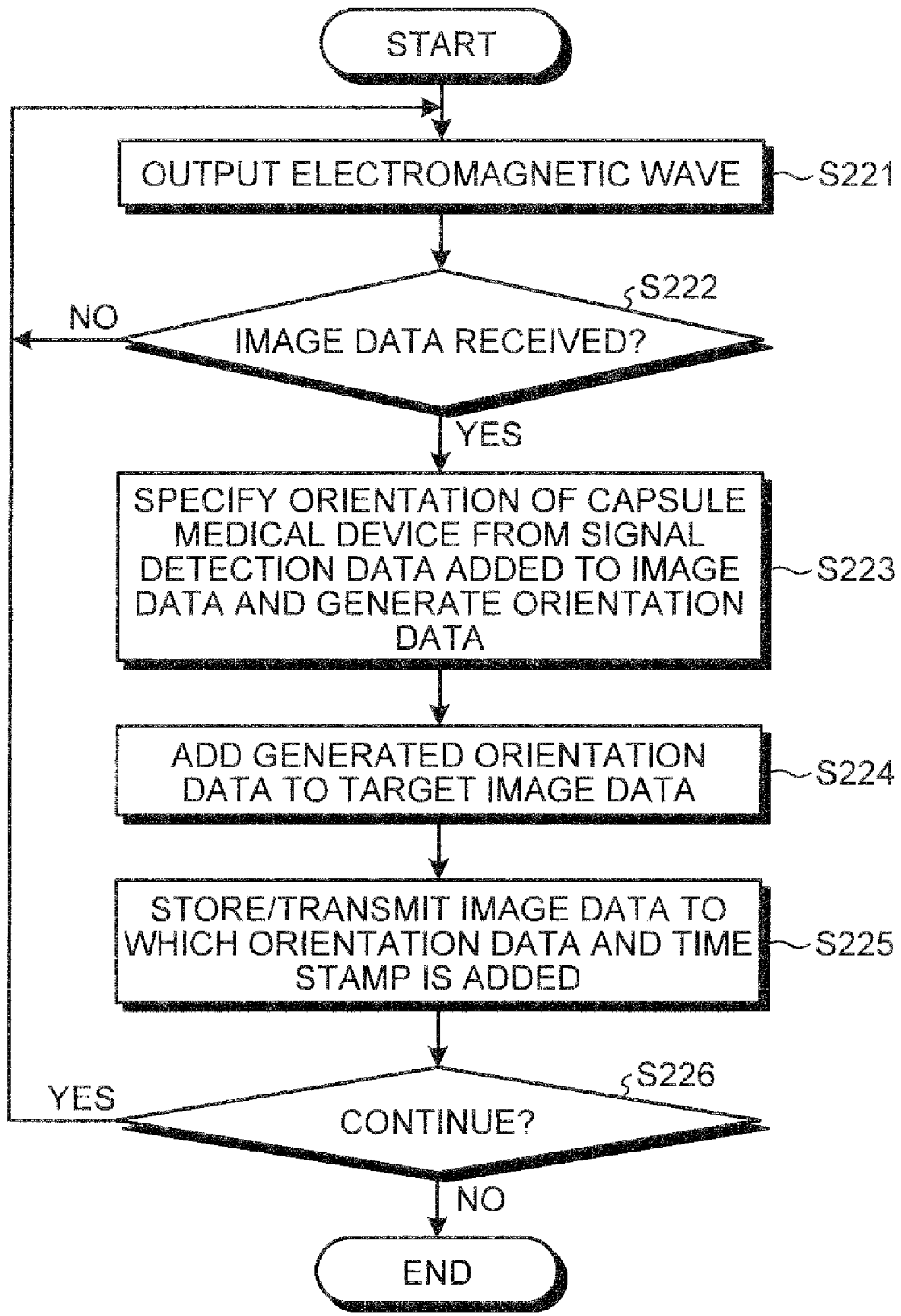
FIG. 28 is a flowchart showing an example of outline operation of the receiving device according to the second embodiment.

Next, the operation of the medical system 2 according to the second embodiment will be described in detail with reference to the drawings. Since the operation of the display device 150 in the second embodiment is similar to that of the first embodiment, in the description, the operation of the capsule medical device 20 and the receiving device 230 will be described below. FIG. 26 is a flowchart showing an example (No. 1) of outline operation of the capsule medical device 20 according to the second embodiment. FIG. 27 is a flowchart showing an example (No. 2) of outline operation of the capsule medical device 20 according to the second embodiment. FIG. 28 is a flowchart showing an example of outline operation of the receiving device 230 according to the second embodiment.

As shown in FIG. 26, after startup, the capsule medical device 20 monitors the antennas 22a and 22b periodically (for example, at intervals of time T (0.5 second)), thereby receiving the electromagnetic wave (sign for orientation detection) transmitted from the receiving device 230 periodically (for example, at intervals of time 0.5 second or less) (Yes in step S201). Subsequently, the capsule medical device 20 obtains, as signal detection data, the strength and phase at each of the antennas 22a and 22b of the received electromagnetic wave (the sign for orientation detection) from the signal detection unit 21 (step S202) and temporarily stores the signal detection data in, for example, the memory unit 13, a not-shown cache memory or the like (step S203). After that, the capsule medical device 20 returns to step S201 and waits for reception of the next electromagnetic wave (sign for orientation detection) (No in step S201). The operation of the capsule medical device 20 shown in FIG. 26 is continued until no power remains in the battery 16 in the capsule medical device 20.

In parallel to the operations shown in FIG. 26, the capsule medical device 20 executes operations shown in FIG. 27. As shown in FIG. 27, after startup, by executing the imaging operation periodically (for example, at intervals of time T (=0.5 second)), the capsule medical device 20 obtains image data (steps S211 and S212). Subsequently, the capsule medical device 20 acquires time at which the image data is obtained (step S213). The capsule medical device 20 also obtains the signal detection data temporarily stored in the memory unit 13, a cache memory, or the like (step S214). The capsule medical device 20 adds the acquisition time as a time stamp to the image data and adds the obtained signal detection data to the image data (step S215). The capsule medical device 20 transmits the image data to which the time stamp and the signal detection data is added as a wireless signal (step S216) and returns to step S211. By such operation, the image data to which the time stamp and the signal detection data is added is periodically transmitted by radio from the capsule medical device 20 to the receiving device 230. The operations of the capsule medical device 20 shown in FIG. 27 are continued until no power remains in the battery 16 in the capsule medical device 20.

On the other hand, as shown in FIG. 28, for example, the receiving device 230 always or periodically outputs the electromagnetic wave (sign for orientation detection) from the antenna 220 (step S221) and monitors whether image data is received from the capsule medical device 20 (No in step S222). In the case where image data is received (Yes in step S222), the receiving device 230 supplies the signal detection data included in the image data received to the CPU 133, estimates spatial spread (electric field distribution) of an electromagnetic wave (sign for orientation detection) from the antenna 220, specifies the orientation with respect to the reference direction Ds of the capsule medical device 20 (that is, orientation with respect to the reference direction Ds of the specified direction Ui) in the CPU 133, and generates it as orientation data (step S223).

Next, like the operation described with reference to FIG. 12 in the first embodiment, the receiving device 230 adds the orientation data generated in the CPU 133 to the image data received in step S222 (step S224) and, as a result, either stores the image data to which the orientation data and the time stamp are added from the interface 137 into the portable recording medium 140 or transmits the image data from the interface 137 to the display device 150 via the communication cable 159 (step S225). After that, the receiving device 230 determines whether the operation is continued, for example, whether an operation end instruction is received from the operation unit 135 (step S226). In the case of continuing the operation (Yes in step S226), the receiving device 230 returns to step S221 and repeats output of the electromagnetic wave (sign for orientation detection) and waiting for reception of next image data. On the other hand, in the case where the operation is not continued (No in step S226), the operation is finished.

With the configuration and operation as described above, in the second embodiment, in a manner similar to the first embodiment (including its modifications), the orientations of a plurality of pieces of image data can be aligned by performing the rotation correction on image data on the basis of the orientation with respect to the reference direction Ds of the capsule medical device 20 at the time of imaging, so that the medical system 2 and the image processing method enabling reduced time and effort on diagnosis and improved accuracy of a diagnosis result can be realized.

Modification 2-1

Although the case of using the electromagnetic wave generation source (antenna 220) as a signal source in the medical system 2 of the second embodiment has been described as an example, the invention is not limited to the case but can use a magnetic field generation source as a signal source. In the following, the case will be described in detail with reference to the drawings as modification 2-1 of the second embodiment. In the following description, the same reference numerals are designated to components similar to those of any of the foregoing embodiments and their modifications for simplicity of description and their description will not be repeated.

Figure 29:
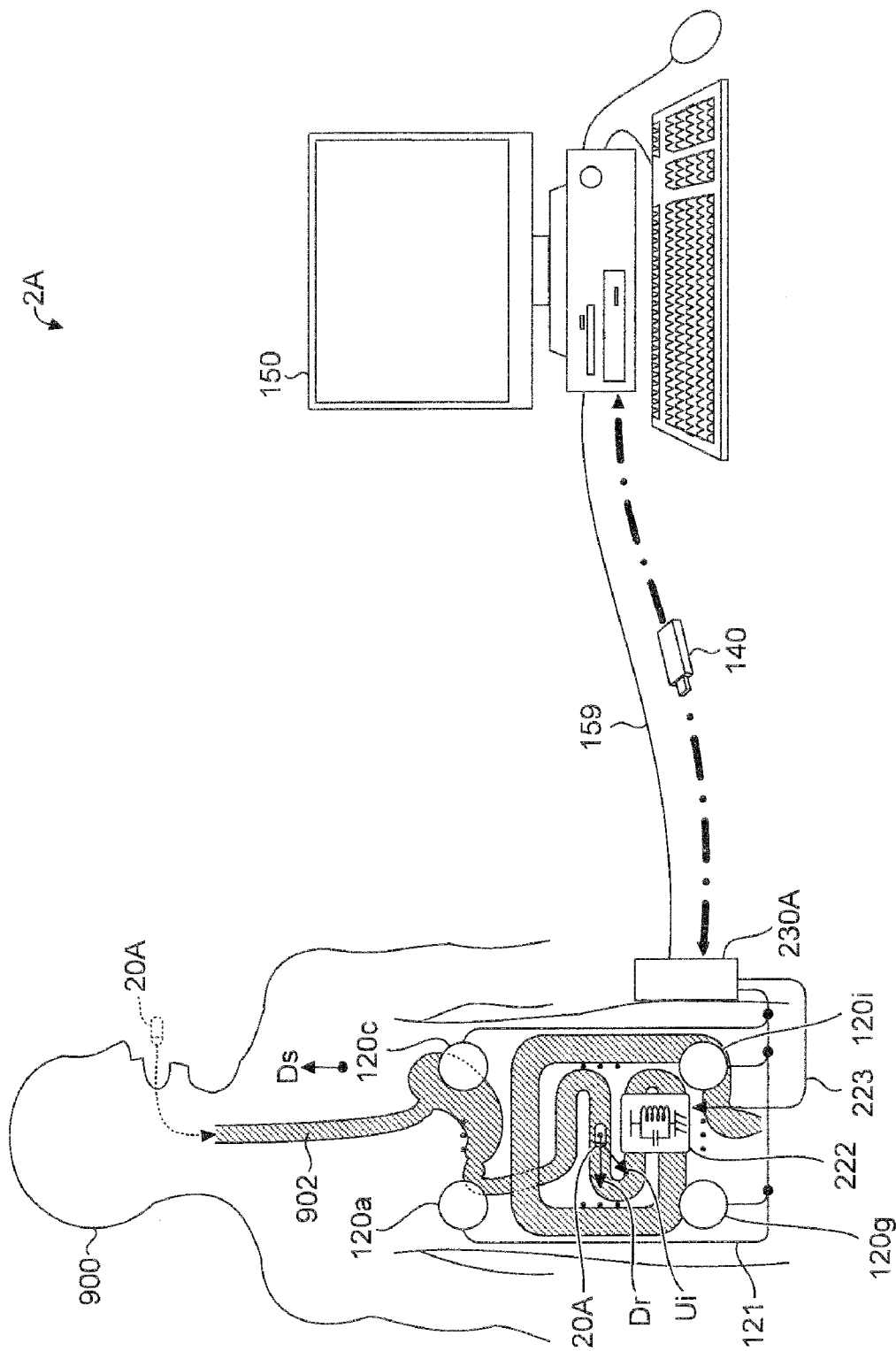
FIG. 29 is a schematic diagram showing a schematic configuration of a medical system according to modification 2-1 of the second embodiment.
Figure 30:
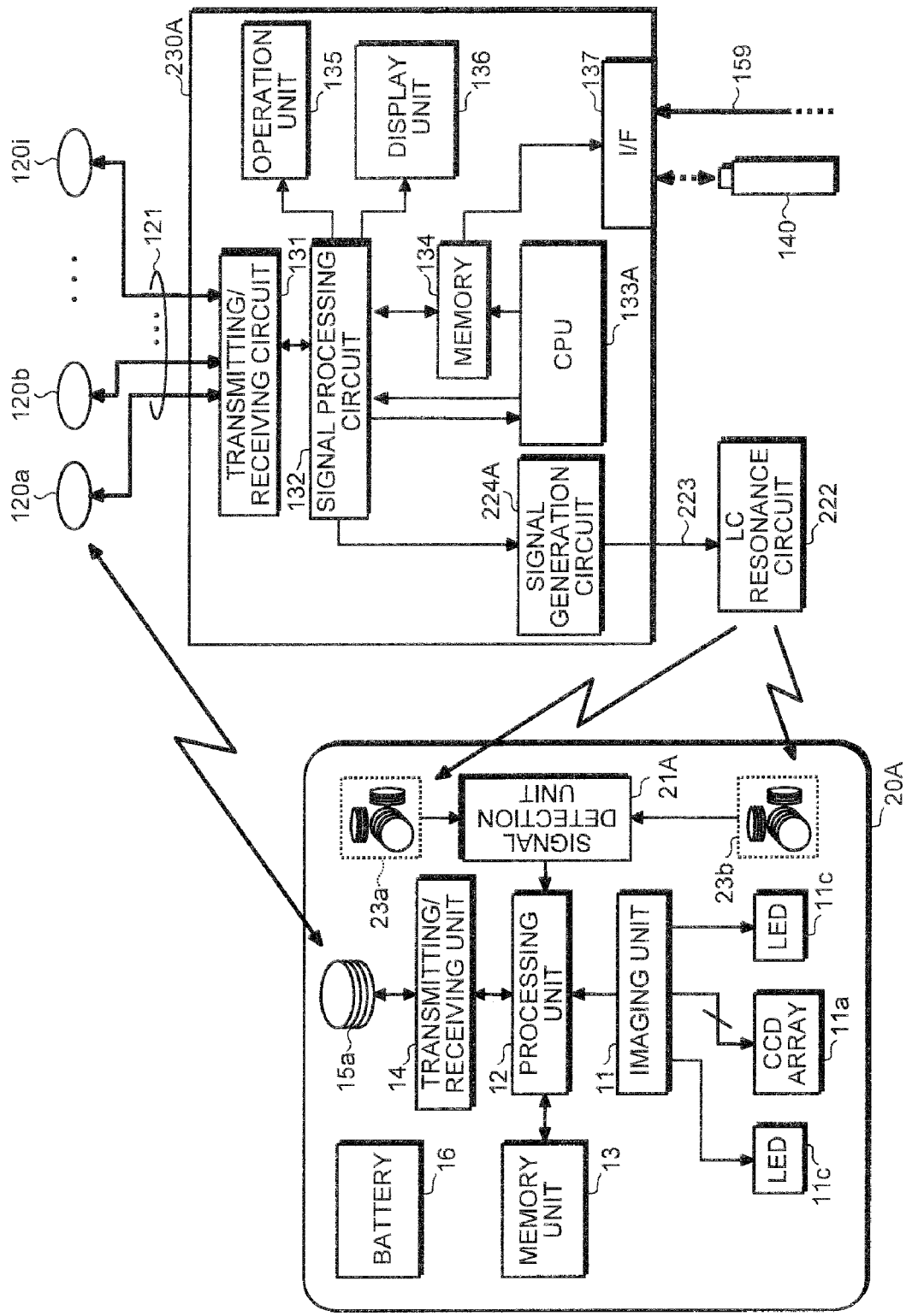
FIG. 30 is a block diagram showing a schematic configuration example of a capsule medical device and a receiving device according to the modification 2-1 of the second embodiment.

FIG. 29 is a schematic diagram showing a schematic configuration of a medical system 2A according to the modification 2-1. FIG. 30 is a block diagram showing a schematic configuration example of a capsule medical device 20A and a receiving device 230A according to the modification 2-1.

As shown in FIG. 29, in the medical system 2A, in comparison with the medical system 2 shown in FIG. 24, the capsule medical device 20 is replaced with the capsule medical device 20A, and the receiving device 230 is replaced with the receiving device 230A. Further, in the medical system 2A, the receiving device 230A is provided with an LC resonance circuit 222 connected to the receiving device 230A via a cable 223.

As shown in FIG. 30, in the capsule medical device 20A, in a configuration similar to the capsule medical device 20 shown in FIG. 25, the antennas 22a and 22b are replaced with magnetic sensors 23a and 23b, and the signal detection unit 21 is replaced with a signal detection unit 21A.

Like the magnetic sensors 123a and 123b in the modification 1-1, each of the magnetic sensors 23a and 23b is, for example, a triaxial magnetic sensor in which three coils whose center axes correspond to the x axis, y axis, and z axis are combined, and functions as an observation point as magnetic field detecting means for observing a sign for orientation detection (a magnetic field in the modification) generated from the LC resonance circuit 222 as a signal source. The invention, however, is not limited to the sensor but a triaxial magnetic sensor made by, for example, a magnetoresistive element, a magnetic impedance element (MI element), a hall element, or the like can be also employed.

The number and the arrangement pattern of the magnetic sensors 23a and 23b can be variously modified as long as the number and the arrangement pattern by which the CPU 133A can estimate/specify the spatial spread (magnetic field distribution) of the magnetic field formed by the LC resonance circuit 222 fixed to the outside surface of the subject 900 are used. In the description, the number of the magnetic sensors 23a and 23b is at least two.

Preferably, the magnetic sensors 23a and 23b are fixed in the casing 18 so that their arrangement direction coincides with the orientation of the specified direction Ui. With the configuration, the arrangement direction with respect to the reference direction Ds of the magnetic sensors 23a and 23b can be directly used as the orientation with respect to the reference direction Ds of the capsule medical device 20A (that is, the specified direction Ui), so that the process in the receiving device 230A which will be described later can be lessened.

The signal detection unit 21A executes a predetermined process including a bandpass process and a process of detecting the orientation and strength of the magnetic field (sign for orientation detection) at the magnetic sensors 23a and 23b on the detection signal input from each of the magnetic sensors 23a and 23b. The signal detection unit 21A adds, as signal detection data, the detected orientation, strength, and the like to image data obtained at the same time or around the same time.

The signal detection data includes data corresponding to the orientation and strength of the magnetic field (sign for orientation detection) at the magnetic sensors 123a and 123b detected by the signal detection circuit 131A in the receiving device 130A in the modification 1-1. To the image data, a time stamp is also added in a manner similar to the modification 1-1. The image data to which the signal detection data and the time stamp are added is transmitted by radio from the antenna 15a to the receiving device 230A from the processing unit 12 via the transmitting/receiving unit 14.

On the other hand, in the receiving device 230A, as shown in FIG. 30, in a configuration similar to the receiving device 230 shown in FIG. 25, a signal generation circuit 224A for supplying a signal of resonance frequency to the LC resonance circuit 222 via the cable 223 is provided. In the receiving device 230A, in a configuration similar to the receiving device 230 shown in FIG. 25, the antenna 220 and the transmitting/receiving circuit 231 are replaced with the antenna 120 and the transmitting/receiving circuit 131 in the first embodiment, respectively, and the CPU 133 is replaced with the CPU 133A in the modification 1-1.

The LC resonance circuit 222 to which a signal of resonance frequency is supplied from the signal generation circuit 224A as signal generating means via the cable 223 is magnetic field forming means for forming an induced magnetic field of resonance frequency by being induced by the input resonance frequency signal, and function as a signal source for generating a signal for orientation detection (magnetic field in the modification) for specifying the orientation of the capsule medical device 20A with respect to the reference direction Ds (that is, tilt of the specified direction Ui).

The LC resonance circuit 222 is fixed on the outside surface (for example, the jacket 122 or the like) of the subject 900. The LC resonance circuit 222 is fixed to the outside surface of the subject 900 so that the polarity direction of an inductor as a component of the LC resonance circuit 222 (corresponding to the symmetrical axis of a magnetic field distribution shape of the magnetic field generated by the LC resonance circuit 222) and the reference direction Ds become parallel to each other. Consequently, even in the case where the capsule medical device 20A rotates using the center line in the longitudinal direction as an axis, the orientation of the specified direction Ui of the capsule medical device 20A with respect to the reference direction Ds can be specified on the basis of the phase, strength, and the like of the magnetic field detected by the magnetic sensors 23a and 23b of the capsule medical device 20A.

In the modification 2-1, the reception signal supplied from the antenna 120 to the transmitting/receiving circuit 131 is supplied to the signal processing circuit 132. In the modification 2-1, as described above, the signal detection data is added to the image data received from the capsule medical device 20A. The signal processing circuit 132 executes a predetermined process on the input signal (particularly, image data), specifies the signal detection data added to the image data, and supplies it to the CPU 133A.

The CPU 133A functions as orientation specifying means estimating spatial spread (magnetic field distribution) of the magnetic field from the LC resonance circuit 222 (sign for orientation detection) from the orientation and strength of the magnetic field (sign for orientation detection) at the magnetic sensors 23a and 23b included in the signal detection data and specifying the orientation with respect to the reference direction Ds of the capsule medical device 20A (that is, orientation with respect to the reference direction Ds of the specified direction Ui). Since the method of estimating the magnetic field distribution is similar to that of the modification 1-1, its detailed description will not be repeated.

As described above, in the modification 2-1, the LC resonance circuit 222 as a signal source is fixed to the outside surface of the subject 900, the magnetic sensors 23a and 23b as observation points are disposed in the capsule medical device 20A, and orientation data indicative of the orientation with respect to the reference direction Ds of the specified direction Ui is generated on the basis of the magnetic field from the LC resonance circuit 222 observed at the magnetic sensors 23a and 23b. The other configuration is similar to any of those in the foregoing embodiments (including their modifications).

Figure 31:
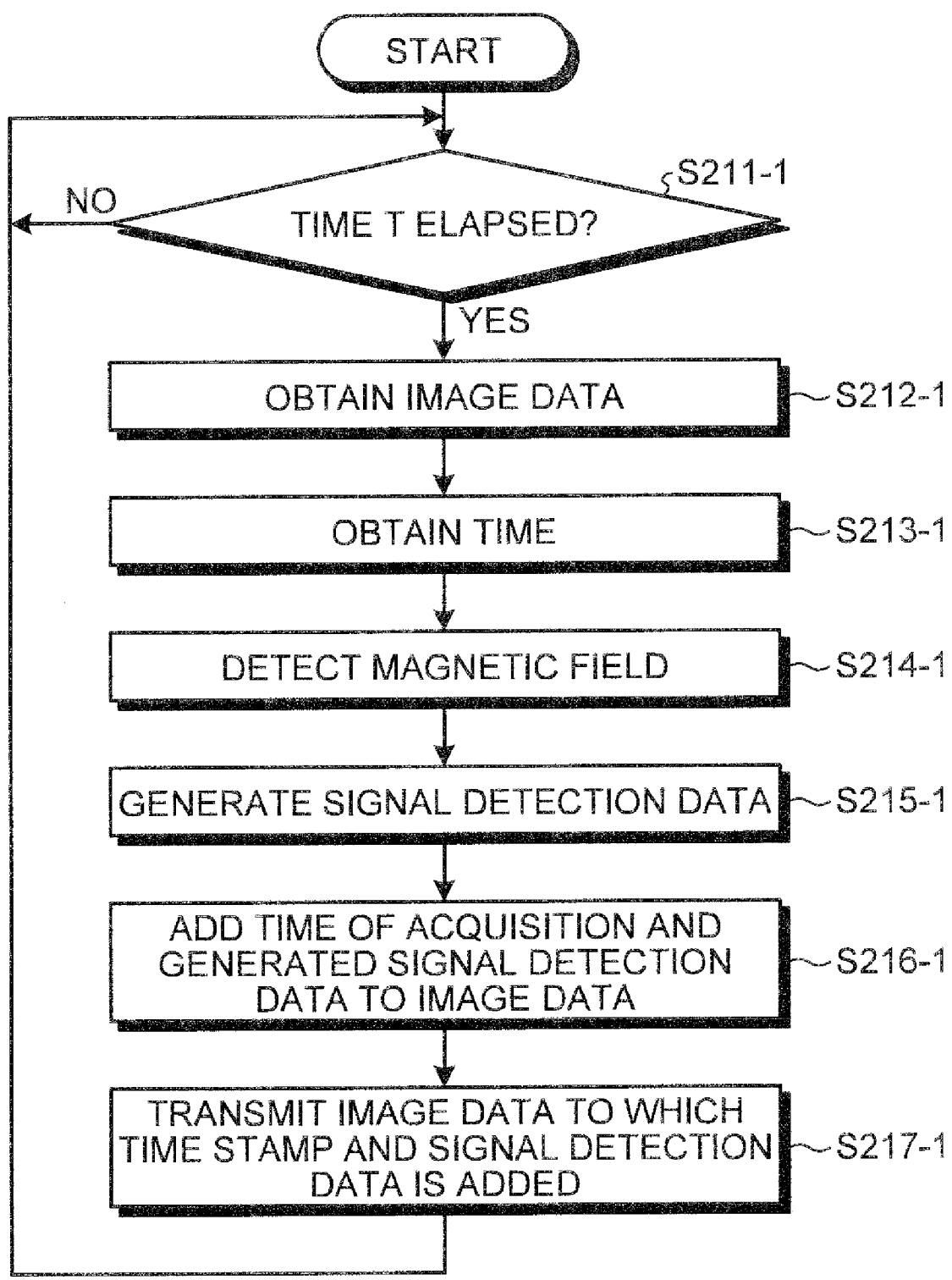
FIG. 31 is a flowchart showing an example of outline operation of the capsule medical device according to the modification 2-1 of the second embodiment.
Figure 32:
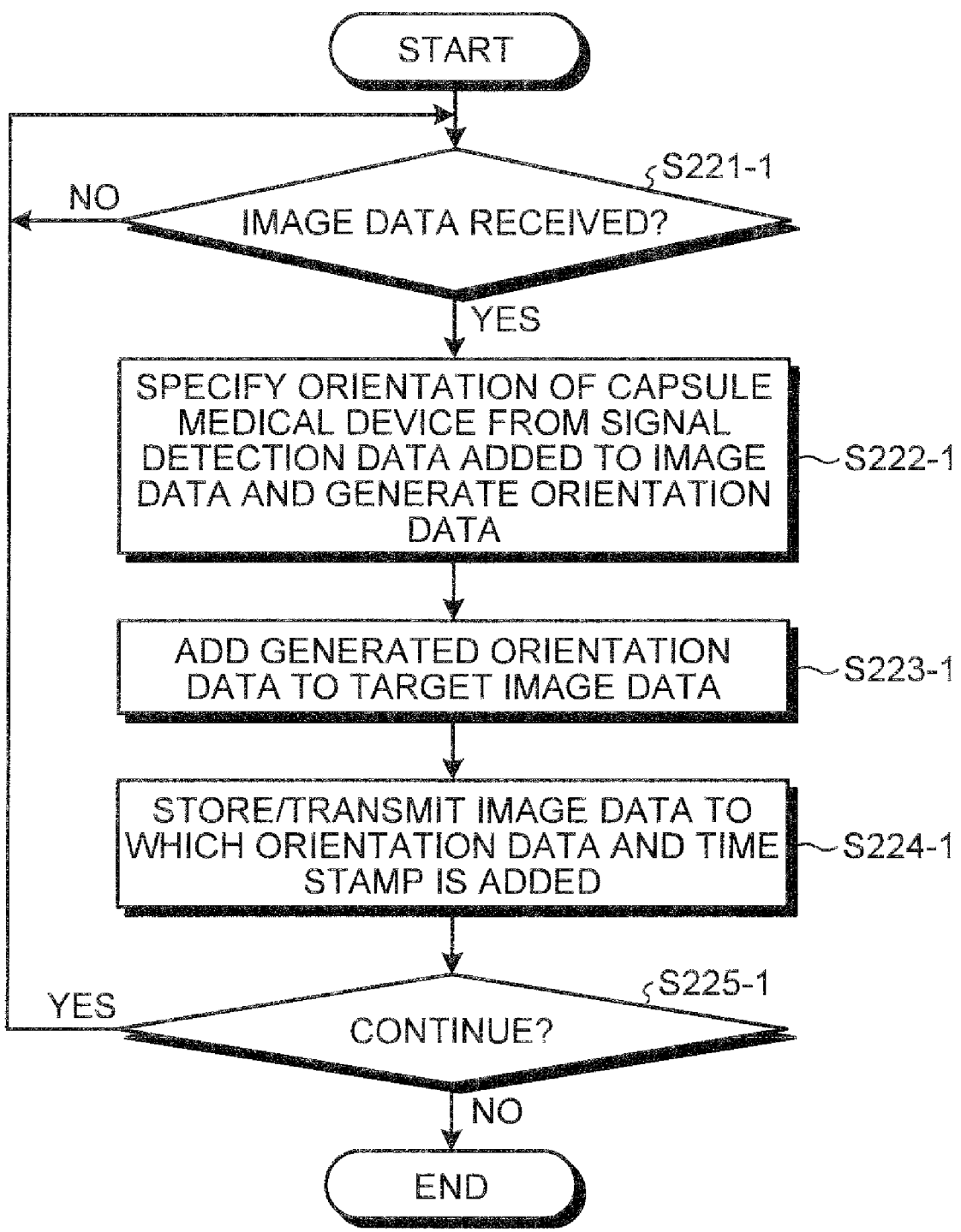
FIG. 32 is a flowchart showing an example of outline operation of the receiving device according to the modification 2-1 of the second embodiment.

Next, the operation of the medical system 2A according to the modification 2-1 will be described in detail with reference to the drawings. Since the operation of the display device 150 in the modification 2-1 is similar to that of the second embodiment, in the description, the operation of the capsule medical device 20A and the receiving device 230A will be described below. FIG. 31 is a flowchart showing an example of outline operation of the capsule medical device 20A according to the modification 2-1. FIG. 32 is a flowchart showing an example of outline operation of the receiving device 230A according to the modification 2-1.

As shown in FIG. 31, after startup, the capsule medical device 20A obtains image data by executing imaging operation periodically (for example, at intervals of time T (0.5 second)) (steps S211-1 to S212-1). Subsequently, the capsule medical device 20A acquires time at which the image data is obtained (step S213-1). The capsule medical device 20A reads detection signals from the magnetic sensors 23a and 23b by using the signal detection unit 21A, executes a predetermined signal process (step S214-1), and generates, as signal detection data, the strength and orientation at each of the magnetic sensors 23a and 23b of the magnetic field obtained (sign for orientation detection) (step S215-1). Subsequently, the capsule medical device 20A adds the acquisition time as a time stamp to the image data and adds the generated signal detection data to the image data (step S216-1). The capsule medical device 20A transmits the image data to which the time stamp and the signal detection data is added as a wireless signal (step S217-1) and returns to step S211-1. By such operation, the image data to which the time stamp and the signal detection data is added is periodically transmitted by radio from the capsule medical device 20A to the receiving device 230A. The operations of the capsule medical device 20A shown in FIG. 31 are continued until no power remains in the battery 16 in the capsule medical device 20A.

On the other hand, the receiving device 230A always supplies the signal of the resonance frequency generated by the signal generation circuit 224A to the LC resonance circuit 222, thereby generating the magnetic field as the sign for orientation detection from the LC resonance circuit 222. In parallel with the operation, as shown in FIG. 32, for example, the receiving device 230A always or periodically monitors whether image data is received from the capsule medical device 20A (No in step S221-1). In the case where image data is received (Yes in step S221-1), the receiving device 230A supplies the signal detection data included in the image data received to the CPU 133A, estimates spatial spread (magnetic field distribution) of the magnetic field from the LC resonance circuit 222, specifies the orientation with respect to the reference direction Ds of the capsule medical device 20A (that is, orientation with respect to the reference direction Ds of the specified direction Ui) in the CPU 133A, and generates it as orientation data (step S222-1).

Next, like the operation described with reference to FIG. 12 in the first embodiment, the receiving device 230A adds the orientation data generated in the CPU 133A to the image data received in step S221-1 (step S223-1) and, as a result, either stores the image data to which the orientation data and the time stamp are added from the interface 137 into the portable recording medium 140 or transmits the image data from the interface 137 to the display device 150 via the communication cable 159 (step S224-1). After that, the receiving device 230A determines whether the operation is continued, for example, whether an operation end instruction is received from the operation unit 135 (step S225-1). In the case of continuing the operation (Yes in step S225-1), the receiving device 230A returns to step S221-1 and repeats output of electromagnetic wave (sign for orientation detection) and waiting for reception of next image data. On the other hand, in the case where the operation is not continued (No in step S225-1), the operation is finished.

With the configuration and operation as described above, in the modification 2-1, in a manner similar to the first or second embodiment (including its modification), the orientations of a plurality of pieces of image data can be aligned by performing the rotation correction on image data on the basis of the orientation with respect to the reference direction Ds of the capsule medical device 20A at the time of imaging, so that the medical system 2A and the image processing method enabling reduced time and effort on diagnosis and improved accuracy of a diagnosis result can be realized.

Modification 2-2

As the signal source in the second embodiment, an ultrasound generation source can be used. In the following, this case will be described in detail as modification 2-2 of the second embodiment with reference to the drawings. In the following description, the same reference numerals are designated to components similar to those of the foregoing embodiment or its modification for simplification of explanation, and their description will not be repeated.

Figure 33:
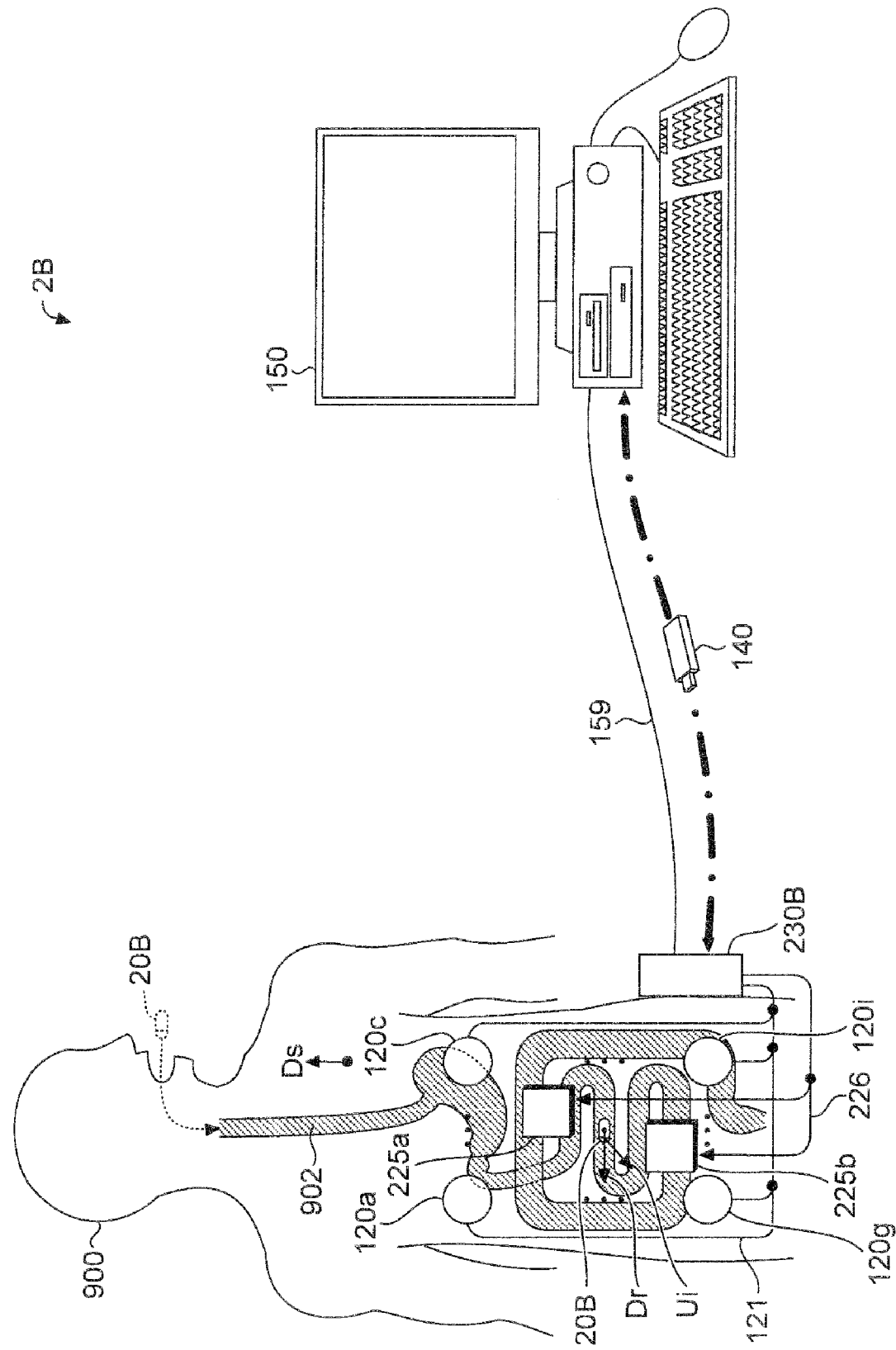
FIG. 33 is a schematic diagram showing a schematic configuration of a medical system according to modification 2-2 of the second embodiment.
Figure 34:
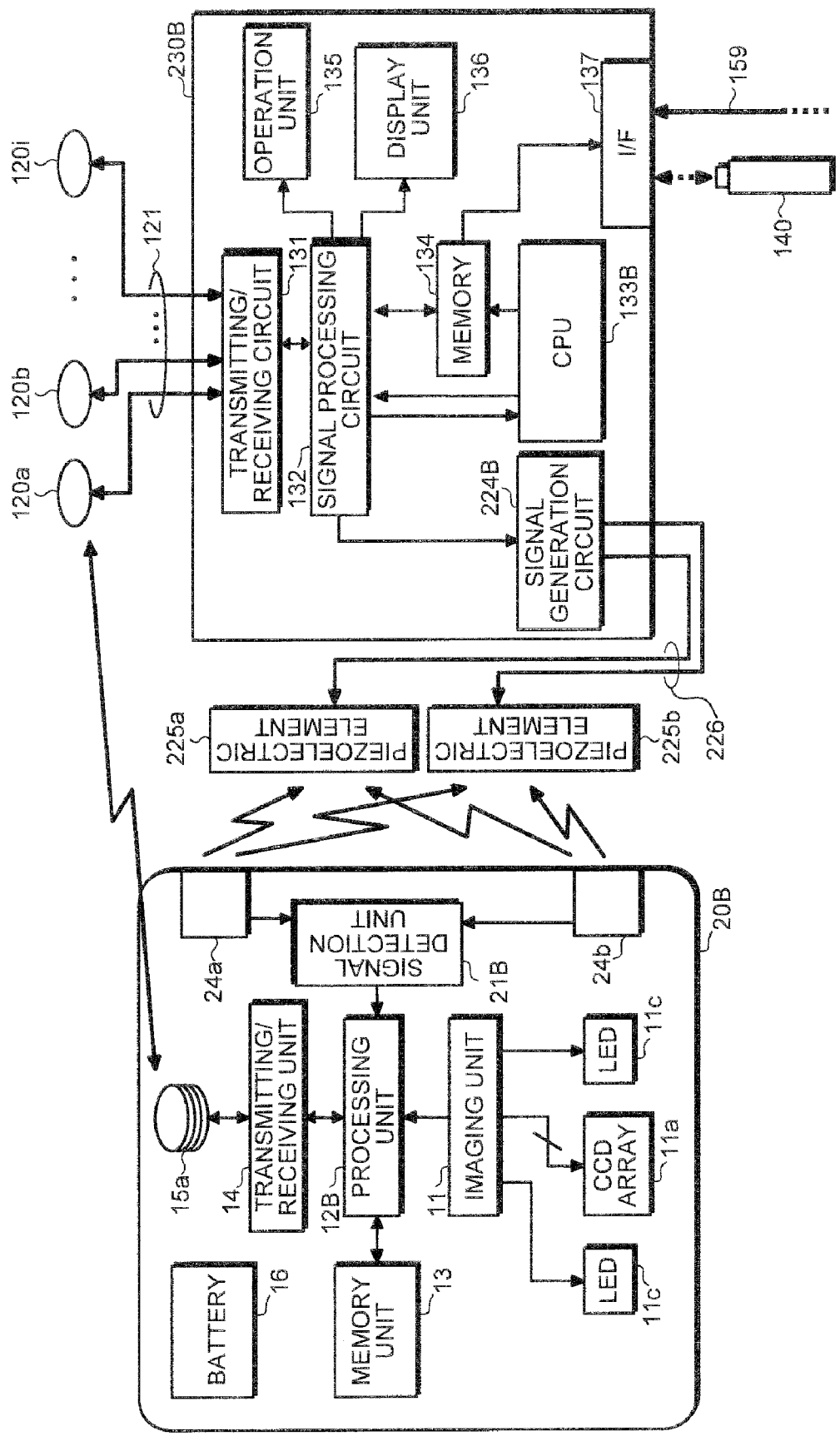
FIG. 34 is a block diagram showing a schematic configuration example of a capsule medical device and a receiving device according to the modification 2-2 of the second embodiment.

FIG. 33 is a schematic diagram showing a schematic configuration of a medical system 2B according to the modification 2-2. FIG. 34 is a block diagram showing a schematic configuration example of a capsule medical device 20B and a receiving device 230B according to the modification 2-2.

As shown in FIG. 33, in the medical system 2B, in comparison with the medical system 2 shown in FIG. 24, the capsule medical device 20 is replaced with the capsule medical device 20B, and the receiving device 230 is replaced with the receiving device 230B. Further, in the medical system 2B, the receiving device 230B is provided with a plurality of piezoelectric elements 225a and 225b connected to the receiving device 230B via a cable 226.

As shown in FIG. 34, in the capsule medical device 20B, in a configuration similar to that of the capsule medical device 20 shown in FIG. 25, the antennas 22a and 22b are replaced with a plurality of acoustic sensors 24a and 24b, and the signal detection unit 21 is replaced with a signal detection unit 21B.

Like the acoustic sensors 125a and 125b of the foregoing modification 1-2, each of the acoustic sensors 24a and 24b is constructed by, for example, a microphone and functions as an observation point as ultrasound detecting means for observing a sign for orientation detection (an ultrasound wave in the modification) generated from the piezoelectric elements 225a and 225b as a signal source. The invention, however, is not limited to the sensors but, for example, a piezoelectric element or the like may be used.

The number and the arrangement pattern of the acoustic sensors 24a and 24b can be variously modified as long as the number and the arrangement pattern by which the CPU 133B can estimate/specify the orientation of the capsule medical device 20B from the strength and phase of ultrasound waves generated by the piezoelectric elements 225a and 225b fixed to the outer surface of the subject 900 are used. In the description, the number of the acoustic sensors 24a and 24b is at least two.

Preferably, the acoustic sensors 24a and 24b are fixed in the casing 18 so that the arrangement direction coincides with the orientation of the specified direction Ui. Since the arrangement direction with respect to the reference direction Ds of the acoustic sensors 24a and 24b can be used directly as the orientation with respect to the reference direction Ds of the capsule medical device 20B (that is, the specified direction Ui), the process in the receiving device 230B which will be described later can be lessened.

The signal detection unit 21B executes, on a detection signal supplied from each of the acoustic sensors 24a and 24b, bandpass process and a predetermined process including a process of detecting the phase and strength of an ultrasonic wave (a sign for orientation detection) in the acoustic sensors 24a and 24b. The signal detection unit 21B adds, as signal detection data, the detected phase, strength, and the like to image data obtained at the same time or around the same time.

The signal detection data includes data corresponding to the phase and strength of the ultrasonic wave (sign for orientation detection) in the acoustic sensors 125a and 125b detected by the signal detection circuit 131B in the receiving device 130B in the modification 1-2. To the image data, a time stamp is also added in a manner similar to the modification 1-2. The image data to which the signal detection data and the time stamp are added is transmitted by radio from the antenna 15a to the receiving device 230B from the processing unit 12B via the transmitting/receiving unit 14.

On the other hand, the receiving device 230B has, as shown in FIG. 34, in addition to a configuration similar to the receiving device 230 shown in FIG. 25, a signal generation circuit 224B for supplying a signal of resonance frequency to the piezoelectric elements 225a and 225b via the cable 226. In the receiving device 230B, in a configuration similar to the receiving device 230 shown in FIG. 25, the antenna 220 and the transmitting/receiving circuit 231 are replaced with the antenna 120 and the transmitting/receiving circuit 131 in the first embodiment, respectively, and the CPU 133 is replaced with the CPU 133B in the modification 1-2.

The piezoelectric elements 225a and 225b to which the signal of resonance frequency is supplied from the signal generation circuit 224B as the signal generating means are ultrasound generating means for generating an ultrasound wave which vibrates by the input resonance frequency signal and generates an ultrasonic wave and functions as a signal source generating a sign for orientation detection (the ultrasound wave in the example) for specifying the orientation of the capsule medical device 20B (that is, tilt of the specified direction Ui) with respect to the reference direction Ds.

Each of the piezoelectric elements 225a and 225b is fixed to the surface (for example, the jacket 122 or the like) of the subject 900. The piezoelectric elements 225a and 225b are fixed to the outside surface of the subject 900 so that the arrangement direction of the piezoelectric elements 225a and 225b and the reference direction Ds become parallel to each other. Even in the case where the capsule medical device 20B rotates around the center line in the longitudinal direction as an axis, the orientation of the specified direction Ui of the capsule medical device 20B with respect to the reference direction Ds can be specified on the basis of the phase, strength, and the like of the ultrasound wave detected by the acoustic sensors 24a and 24b of the capsule medical device 20B.

In the modification 2-2, the reception signal supplied from the antenna 120 to the transmitting/receiving circuit 131 is supplied to the signal processing circuit 132. In the modification 2-2, as described above, the signal detection data is added to the image data received from the capsule medical device 20B. The signal processing circuit 132 executes a predetermined process on the input signal (particularly, image data), specifies the signal detection data added to the image data, and supplies it to the CPU 133B.

The CPU 133B functions as orientation specifying means estimating spatial spread (ultrasound distribution) of the ultrasound wave (sign for orientation detection) from the piezoelectric elements 225a and 225b from the phase and strength of the ultrasonic wave (sign for orientation detection) in the acoustic sensors 24a and 24b included in the signal detection data and specifying the orientation with respect to the reference direction Ds of the capsule medical device 20B (that is, the orientation with respect to the reference direction Ds of the specified direction Ui). Since the method of estimating the ultrasonic wave distribution is similar to that of the modification 1-2, its detailed description will not be repeated.

As described above, in the modification 2-2, the piezoelectric elements 225a and 225b as a signal source are fixed to the outside surface of the subject 900, the acoustic sensors 24a and 24b as observation points are disposed in the capsule medical device 20B, and orientation data indicative of the orientation with respect to the reference direction Ds of the specified direction Ui is generated on the basis of the ultrasound wave from the piezoelectric elements 225a and 225b observed at the acoustic sensors 24a and 24b. The other configuration is similar to any of those in the foregoing embodiments (including their modifications).

Figure 35:
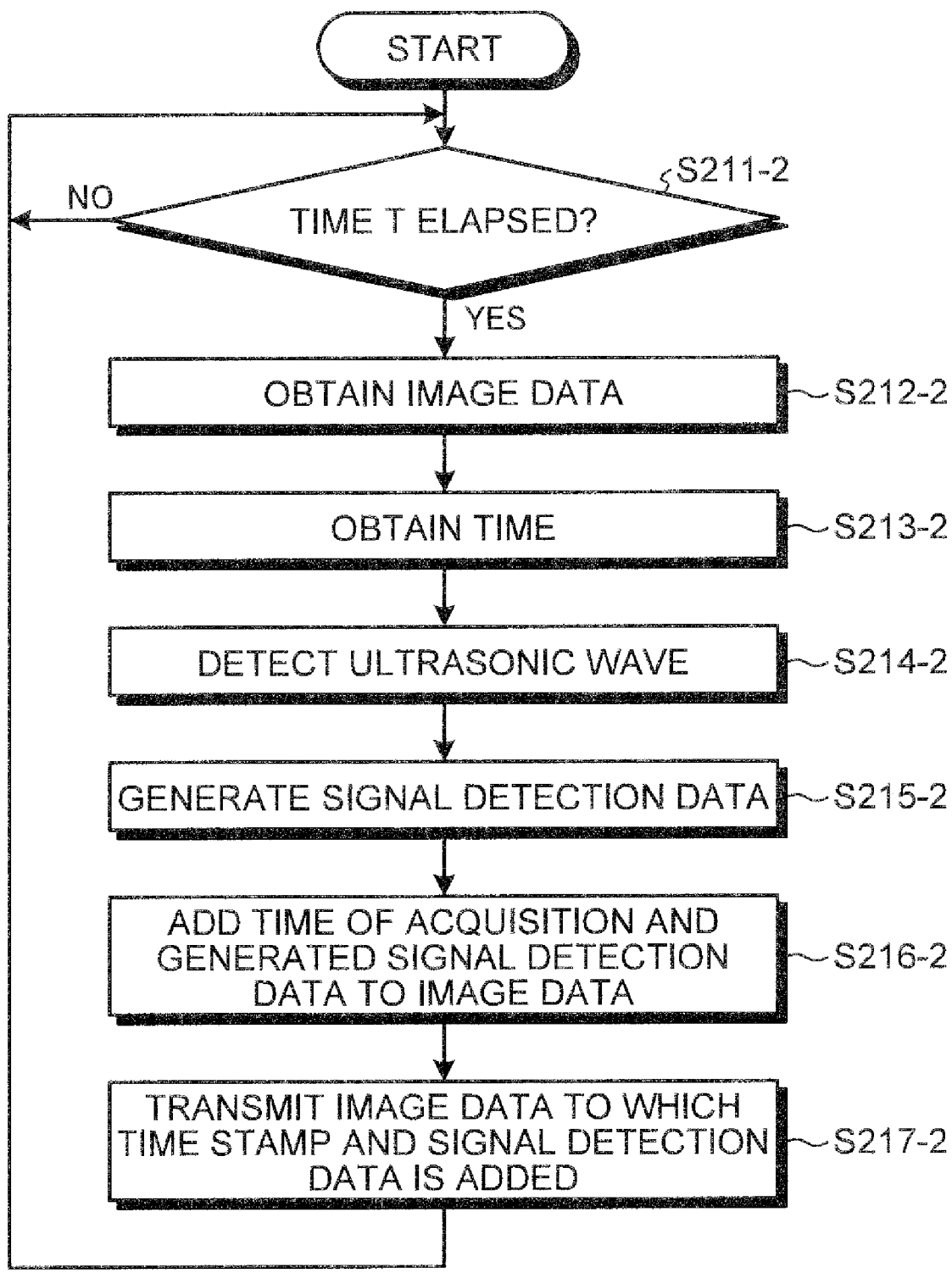
FIG. 35 is a flowchart showing an example of outline operation of the receiving device according to the modification 2-2 of the second embodiment.

Next, the operation of the medical system 2B according to the modification 2-2 will be described in detail with reference to the drawings. Since the operation of the receiving device 230B and the display device 150 in the modification 2-2 is similar to that of the second embodiment, in the description, the operation of the capsule medical device 20B will be described below. The receiving device 230B generates an ultrasound wave as a sign for orientation detection from the piezoelectric elements 225a and 225b by always supplying the signal of the resonance frequency generated by the signal generation circuit 224B to the piezoelectric elements 225a and 225b. FIG. 35 is a flowchart showing an example of outline operation of the receiving device 230B according to the modification 2-2.

As shown in FIG. 35, after startup, the capsule medical device 20B obtains image data by executing imaging operation periodically (for example, at intervals of time T (0.5 second)) (steps S211-2 to S212-2). Subsequently, the capsule medical device 20B acquires time at which the image data is obtained (step S213-2). The capsule medical device 20B reads detection signals from the acoustic sensors 24a and 24b by using the signal detection unit 21B, executes a predetermined signal process (step S214-2), and generates, as signal detection data, the strength and phase at each of the acoustic sensors 24a and 24b of the received ultrasonic wave (the sign for orientation detection) (step S215-2). Subsequently, the capsule medical device 20B adds the acquired time as a time stamp to the image data and adds the generated signal detection data to image data (step S216-2). Next, the capsule medical device 20B transmits, as a wireless signal, image data to which the time stamp and the signal detection data is added (step S217-2) and returns to step S211-2. By the operation, the image data to which the time stamp and the signal detection data is added is periodically transmitted by radio from the capsule medical device 20B to the receiving device 230B. The operation of the capsule medical device 20B shown in FIG. 35 is continued until no power remains in the battery 16 in the capsule medical device 20B.

With the configuration and operation as described above, in the modification 2-2, in a manner similar to the first or second embodiment (including its modifications), the orientations of a plurality of pieces of image data can be aligned by performing the rotation correction on image data on the basis of the orientation with respect to the reference direction Ds of the capsule medical device 20B at the time of imaging, so that the medical system 2B and the image processing method enabling reduced time and effort on diagnosis and improved accuracy of a diagnosis result can be realized.

Third Embodiment

Although the case of setting the reference direction Ds in the subject 900 and performing rotation correction on image data in accordance with an orientation relative to the subject 900 has been described as an example in the foregoing embodiments (including their modifications), the invention is not limited to the case. The reference direction may be set out of the subject 900. Specifically, the reference direction used at the time of performing rotation correction may be set to a system independent of the orientation and posture of the subject 900. An example of such a system is real space. In the following, the case of setting the reference direction Ds in the real space will be described in detail as a third embodiment with reference to the drawings. In the following description, the same reference numerals are designated to components similar to those of the forgoing embodiment and its modifications for simplicity of explanation, and their detailed description will not be repeated.

Figure 36:
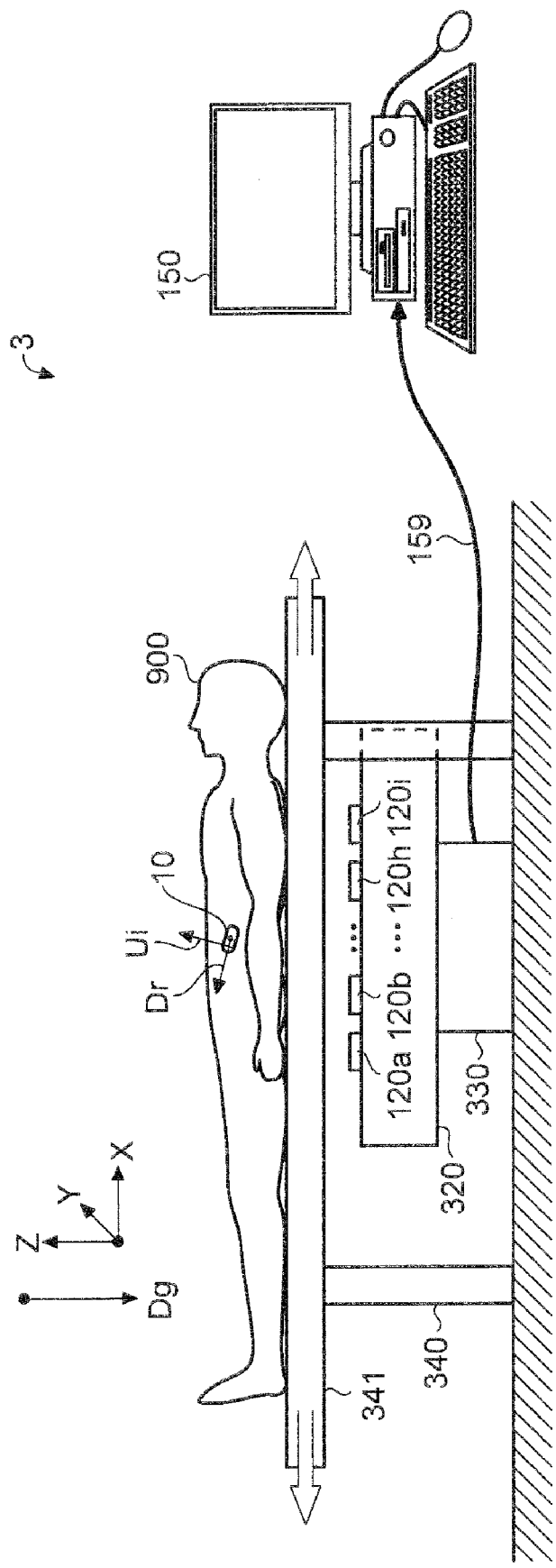
FIG. 36 is a schematic diagram showing a schematic configuration of a medical system according to a third embodiment.
Figure 37:
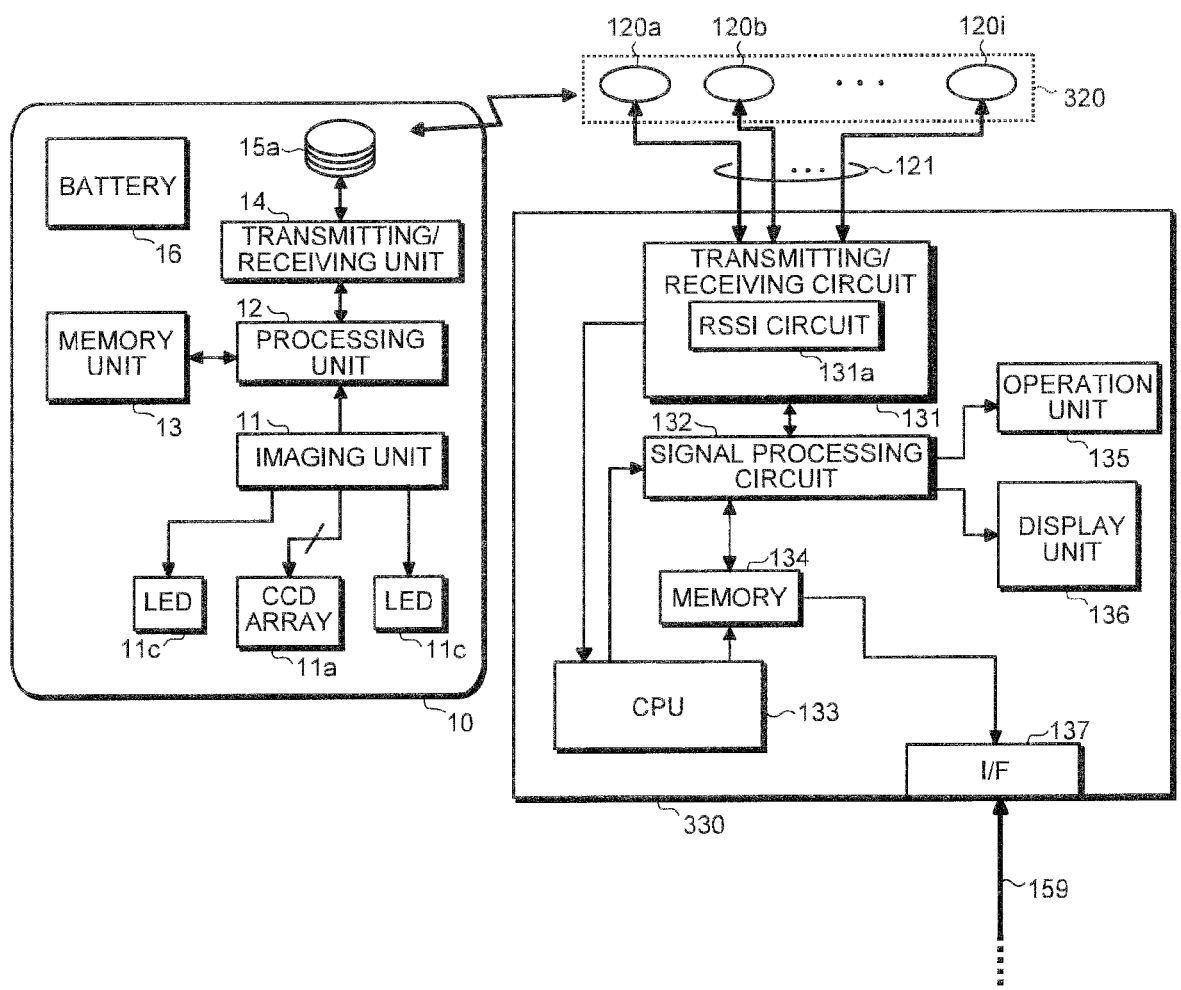
FIG. 37 is a block diagram showing a schematic configuration example of a capsule medical device and a receiving device according to the third embodiment.

FIG. 36 is a schematic diagram showing a schematic configuration of a medical system 3 according to the third embodiment. FIG. 37 is a block diagram showing an example of a schematic configuration of the capsule medical device 10 and a receiving device 330 according to the third embodiment. In the third embodiment, the capsule medical device 10 according to the first embodiment is used. The capsule medical device 10 has the antenna 15a having directivity.

As illustrated in FIG. 36, in the medical system 3, in comparison with the medical system 1 shown in FIG. 1, the receiving device 130 is replaced with the receiving device 330. The receiving device 330 is mounted on, for example, the floor so as not to move. The space including the floor is real space in which a reference direction Dg is set in the third embodiment.

Further, the medical system 3 has a sensor stand 320 mounted on the floor surface so as not to move, a bed 341 on which the subject 900 lies, and a movable stage 340 supporting the bed 341 so as to be movable in the horizontal direction. In the embodiment, the capsule medical device 10 according to the first embodiment is used. The bed 341 may be fixed to the floor surface so as not to move.

As shown in FIG. 37, the receiving device 330 has a configuration similar to that of the receiving device 130 shown in FIG. 5. The antennas 120 connected to the receiving device 330 via the cable 121 are, for example, arranged in a matrix on the sensor stand 320 fixed to the receiving device 330 so as not to move relative to the floor surface. The sensor stand 320 is mounted so that the face on which the antennas 120 are arranged faces the rear face of the bed 341. That is, the sensor stand 320 is mounted below the bed 341 in a state where the face on which the antennas 120 are arranged faces upward. The invention, however, is not limited to the arrangement but can be variously modified to, for example, the antennas 120 are disposed in the bed 341 so as to be arranged on the mount face or the rear face of the bed 341.

By making the bed 341 horizontally movable, particularly, horizontally movable with respect to the sensor stand 320, the position of the subject 900 relative to the antennas 120, that is, the position of the capsule medical device 10 can be properly adjusted. Thus, the orientation of the capsule medical device 10 can be specified with higher precision.

As described above, in the third embodiment, by fixing the antennas 120 as observation points in the real space, orientation data indicative of the orientation of the specified direction Ui with respect to the reference direction Dg set in the real space is generated. The other configuration is similar to that of any of the foregoing embodiments (including their modifications). Since the operation of the medical system 3 according to the embodiment is similar to that of the first embodiment, the detailed description will not be repeated.

Figure 38:
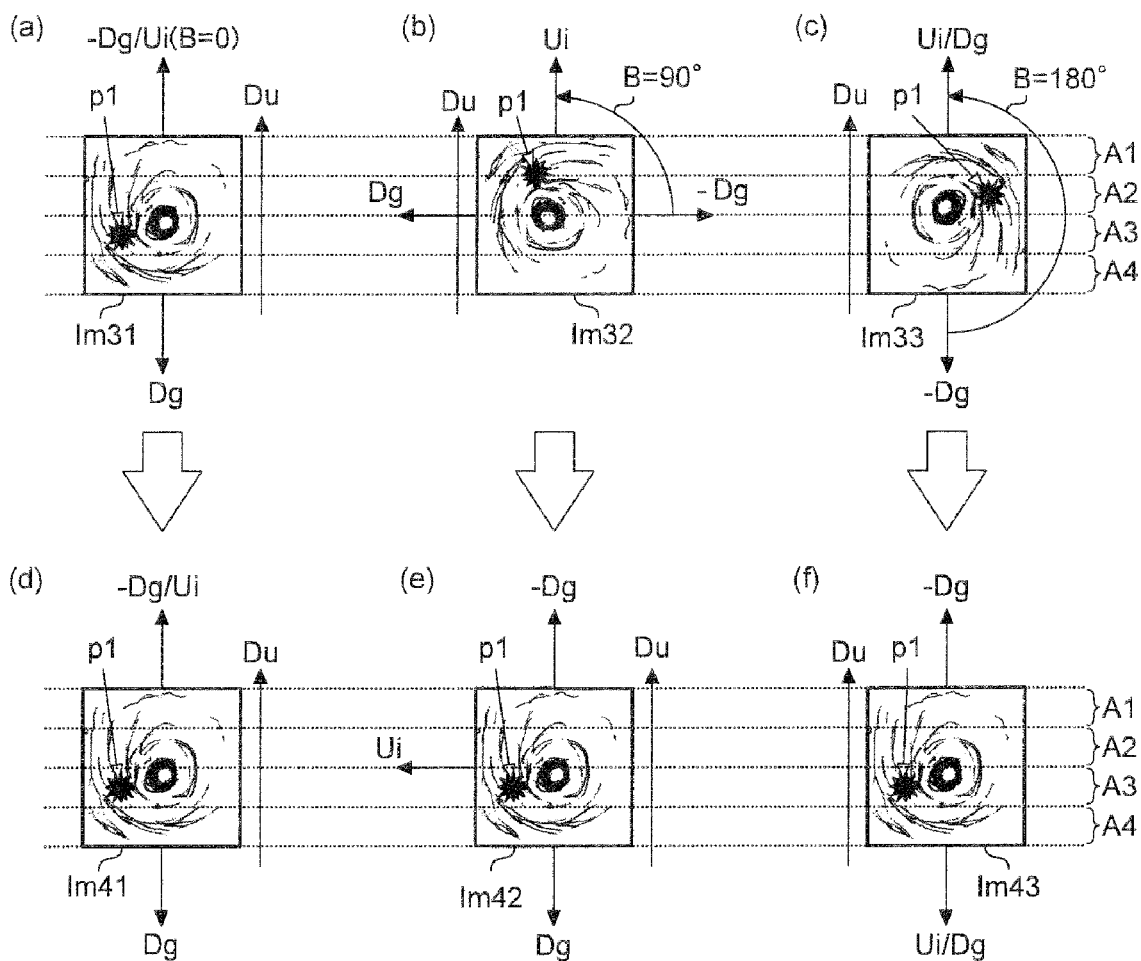
FIG. 38 is a diagram for explaining rotation correction according to the third embodiment.
Figure 39:
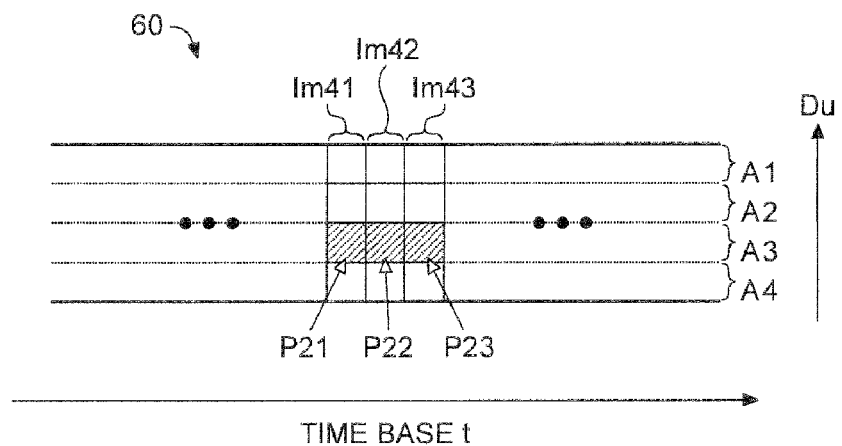
FIG. 39 is a diagram showing an example of an average color bar generated by using image data subjected to rotation correction according to the third embodiment.

An example of the rotation correction according to the third embodiment and an example of the average color bar generated by using the image data subjected to the rotation correction according to the third embodiment will be described in detail with reference to the drawings. FIG. 38 is a diagram for explaining the rotation correction according to the third embodiment. FIG. 39 is a diagram showing an example of the average color bar 60 generated by using the image data subjected to the rotation correction according to the third embodiment.

As shown in (a) in FIG. 38, in image data Im31 obtained at the first imaging timing, the specified direction Ui and the reference direction Dg coincide with each other. Consequently, a rotation amount (correction amount) B at the time of the rotation correction on the image data Im31 is 0°. As shown in (b) in FIG. 38, in image data Im32 obtained at the second imaging timing, the angle of the specified direction Ui with respect to the reference direction Dg is 90°. Therefore, the rotation amount (correction amount) B at the time of the rotation correction on the image data Im32 is 90°. Further, as shown in (c) in FIG. 38, in image data Im33 obtained at the third imaging timing, the angle of the specified direction Ui with respect to the reference direction Dg is 180°. Therefore, the rotation amount (correction amount) B at the time of the rotation correction on the image data Im33 is 180°. The rotation correcting unit 154a in the display device 150 of the embodiment performs the rotation correction on the image data Im31 to Im33 on the basis of the orientation data in a manner similar to the foregoing embodiments (including their modifications). Consequently, in image data Im41 to Im43 subjected to the rotation correction, as shown in (d) to (f) in FIG. 38, the upward direction Cu of the screen coincides with the reference direction Dg.

As a result of the rotation correction as described above, as illustrated in (d) to (f) in FIG. 38, the same part p1 in image data Im41 to Im43 is included in the same division region A3. Consequently, as shown in FIG. 39, the positions of regions P21 to 923 including the same part p1 in the average color bar 60 generated by using the image data Im41 to Im43 subjected to the rotation correction can be aligned in the horizontal direction in the division region A3. (d) in FIG. 38 shows the image data Im41 obtained by rotation-correcting the image data Im31 of (a) in FIG. 38, (e) in FIG. 38 shows the image data Im42 obtained by rotation-correcting the image data Im32 of (b) in FIG. 38, and (f) in FIG. 38 shows the image data Im43 obtained by rotation-correcting the image data Im33 of (c) in FIG. 38.

Also in the third embodiment, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

With the configuration and operation as described above, in the third embodiment, in a manner similar to the first embodiment, the orientations of a plurality of pieces of image data can be aligned by performing the rotation correction on image data on the basis of the orientation with respect to the reference direction Dg of the capsule medical device 10 at the time of imaging, so that the medical system 3 and the image processing method enabling reduced time and effort on diagnosis and improved accuracy of a diagnosis result can be realized.

Also in the third embodiment, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction. Dg is obtained and, using the tilt (rotation amount) and the orientation (correction amount B) of the specified direction Ui with respect to the reference direction Dg, image data is rotation-corrected.

Modification 3-1

Although the case of using the electromagnetic wave generating source (antenna 15*a*) as the signal source has been described as an example in the medical system 3 according to the third embodiment, the invention is not limited to the case but a magnetic field generating source can be used as the signal source. The case will be described in detail below as modification 3-1 of the third embodiment with reference to the drawings. In the following description, the case of specifying the orientation of the capsule medical device 10A' by a so-called passive method of making an LC resonance circuit 17*b* mounted on the capsule medical device 10A' excite by using an external magnetic field (drive magnetic field) to generate an induced magnetic field will be taken as an example. In the following description, the same reference numerals are designated to components similar to those of any of the foregoing embodiments and their modifications for simplicity of explanation, and their detailed description will not be repeated.

Figure 40:
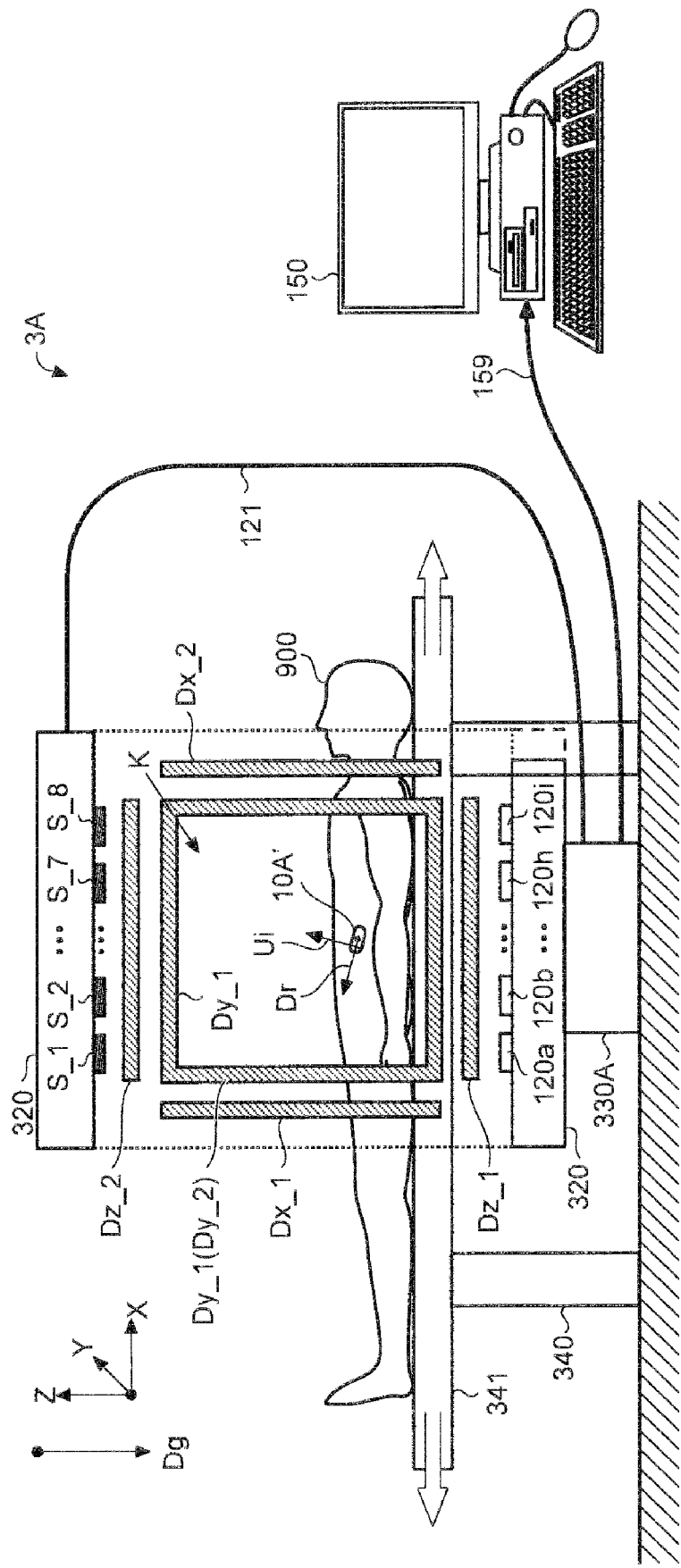
FIG. 40 is a schematic diagram showing a schematic configuration of a medical system according to modification 3-1 of the third embodiment.
Figure 41:
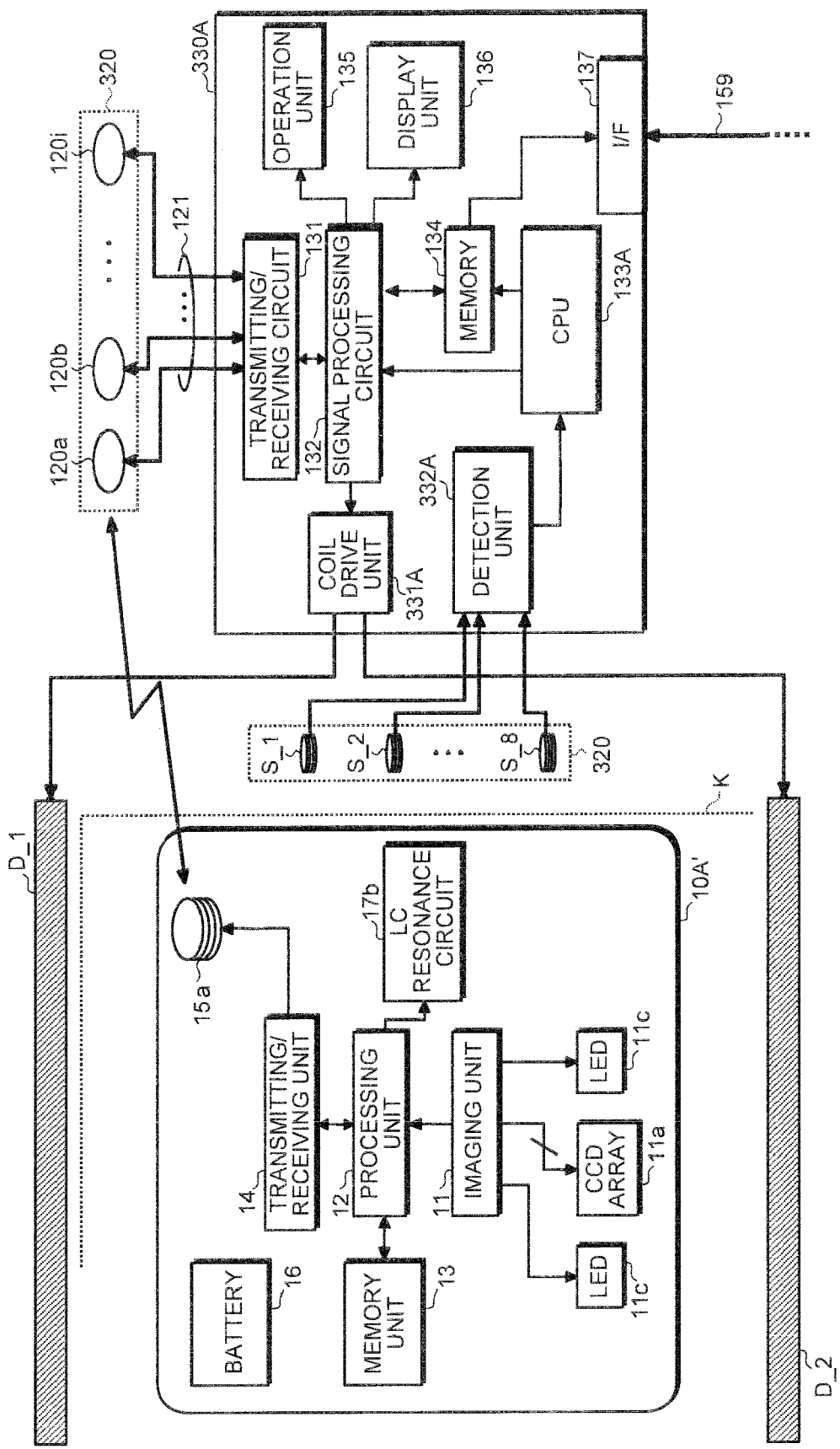
FIG. 41 is a block diagram showing a schematic configuration example of a capsule medical device and a receiving device according to the modification 3-1 of the third embodiment.

FIG. 40 is a schematic diagram showing a schematic configuration of a medical system 3A according to the modification 3-1. FIG. 41 is a block diagram showing a achematic configuration example of the capsule medical device 10A and a receiving device 330A. In the modification 3-1, the capsule medical device 10A' in the modification 1®1 is used. The capsule medical device 10A' has, as a signal source, the LC resonance circuit 17*b* generating an induced magnetic field when induced by the external magnetic field (drive magnetic field) of a predetermined resonance frequency.

As shown in FIG. 40, in the medical system 3A, as compared with the medical system 3 shown in FIG. 36, the capsule medical device 10 is replaced with the capsule medical device 10A, and the receiving device 330 is replaced with the receiving device 330A. The receiving device 330A is mounted, for example, on the floor or the like so as not to move like the receiving device 330. In the periphery of a part (hereinbelow, called detection space K) in the space in which the subject 900 on the bed 341 is mounted, total three sets of drive coils Dx_1 and Dx_2, Dy_1 and Dy_2, and Dz_1 and Dz_2, opposed in the x axis, y axis, and z axis are disposed. In the following, the reference numeral of an arbitrary drive coil will be called D, and reference numerals of drives coils of an arbitrary pair will be called D_1 and D_2.

Further, the medical system 3A has the sensor stand 320 mounted so as not to move relative to the floor face and a plurality of magnetic sensors S_1 to S_8 arranged in a matrix, for example, on the sensor stand 320 so as not to move relative to the floor face. In the following, the reference numeral of an arbitrary magnetic sensor will be S. The sensor stand 320 is mounted so that the face on which the magnetic sensors S are arranged is adjacent to the detection space K. For example, the sensor stand 320 is mounted over the detection space K in a state where the face on which the magnetic sensors S are arranged faces downward. The invention, however, is not limited to the arrangement but can be variously modified such as a case that the antennas 120 are disposed in the bed 341 so as to be arranged on the mount face or the rear face of the bed 341.

As shown in FIG. 41, in the receiving device 330A, in a configuration similar to that of the receiving device 330 shown in FIG. 37, the CPU 133 is replaced with the CPU 133A. Further, the receiving device 330A has a coil drive unit 331A for generating a drive signal almost equal to the resonance frequency of the LC resonance circuit 17*b* and supplying it to the drive coil D, and a signal detection unit 332A for reading a potential change which occurs in any of the magnetic sensors S as a detection signal.

The drive coil D generates a drive magnetic field of an almost resonance frequency in the detection space K by the drive signal input from the coil drive unit 331A. Each of the magnetic sensors S is influenced by an induced magnetic field generated when the LC resonance circuit 17*b* of the capsule medical device 10A' is excited by the drive magnetic field generated in the detection space K, and changes its potential. The potential change occurring in each of the magnetic sensors S depends on the position and orientation of each of the magnetic sensors S disposed and the position and orientation of the LC resonance circuit 17*b*.

The signal detection unit 332A reads, as a detection signal, a potential change occurring in each of the magnetic sensors S via the cable 121, executes a predetermined process such as frequency separation or EFT and, after that, supplies the processed detection signal as orientation data to the CPU 133A.

Like the CPU 133 in the foregoing first embodiment, the CPU 133A functions as orientation specifying means specifying the orientation of the capsule medical device 10A' (that is, tilt of the specified direction Ui) with respect to the reference direction Dg from the strength and orientation of the sign (magnetic field) for orientation detection observed at the observation points (the magnetic sensors S_1 to S_8). That is, the CPU 133A estimates the spatial spread of the magnetic field (magnetic field distribution) on the basis of the magnetic field strength of a detection signal, the orientation of a line of magnetic force, and the like in each of the magnetic sensors S supplied from the signal detection circuit 332A and specifies the orientation with respect to the reference direction Dg of the capsule medical device 10A" (that is, the orientation with respect to the reference direction Dg of the specified direction Ui). In a manner similar to the foregoing embodiments, information of the orientation (orientation data) with respect to the reference direction Dg of the specified direction Ui specified by the CPU 133A is temporarily stored in association with image data received simultaneously or around the same time from the capsule medical device 10A into the memory 134.

In such a manner, in the modification 3-1, by fixing the magnetic sensor S as the observation point in the real space, orientation data indicative of the orientation of the specified direction Ui with respect to the reference direction Dg which is set for the real space is generated. The other configuration is similar to that of any of the foregoing embodiments (including their modifications). Since the operation of the medical system 3A according to the embodiment is similar to that of the modification 1-1, the detailed description will not be repeated.

With the configuration and operation as described above, in the modification 3-1, in a manner similar to the first embodiment, the orientations of a plurality of pieces of image data can be aligned by performing the rotation correction on image data on the basis of the orientation with respect to the reference direction Dg of the capsule medical device 10A' at the time of imaging, so that the medical system 3A and the image processing method enabling reduced time and effort on diagnosis and improved accuracy of a diagnosis result can be realized.

Also in the modification 3-1, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Modification 3-2

As the signal source in the third embodiment, an ultrasound generation source can be also used. In the following description, the same reference numerals are designated to components similar to those of any of the foregoing embodiments and their modifications for simplicity of explanation, and their detailed description will not be repeated.

Figure 42:
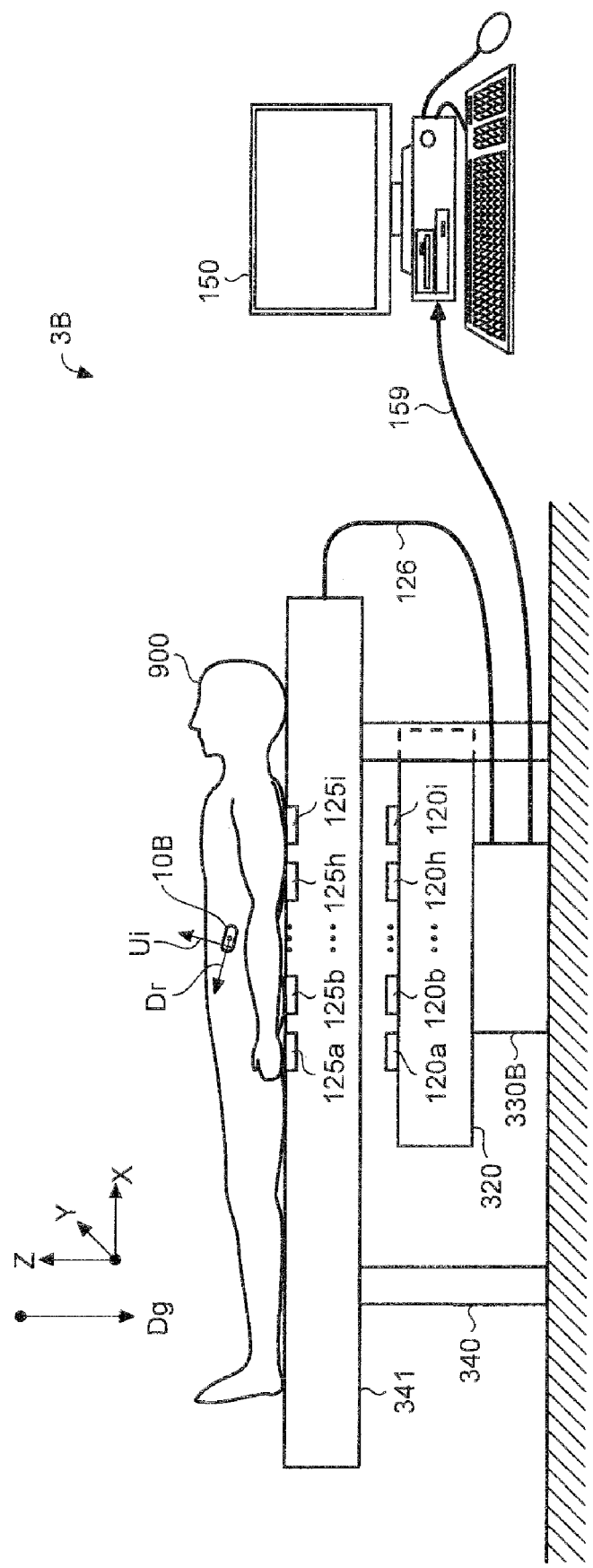
FIG. 42 is a schematic diagram showing a schematic configuration of a medical system according to modification 3-2 of the third embodiment.
Figure 43:
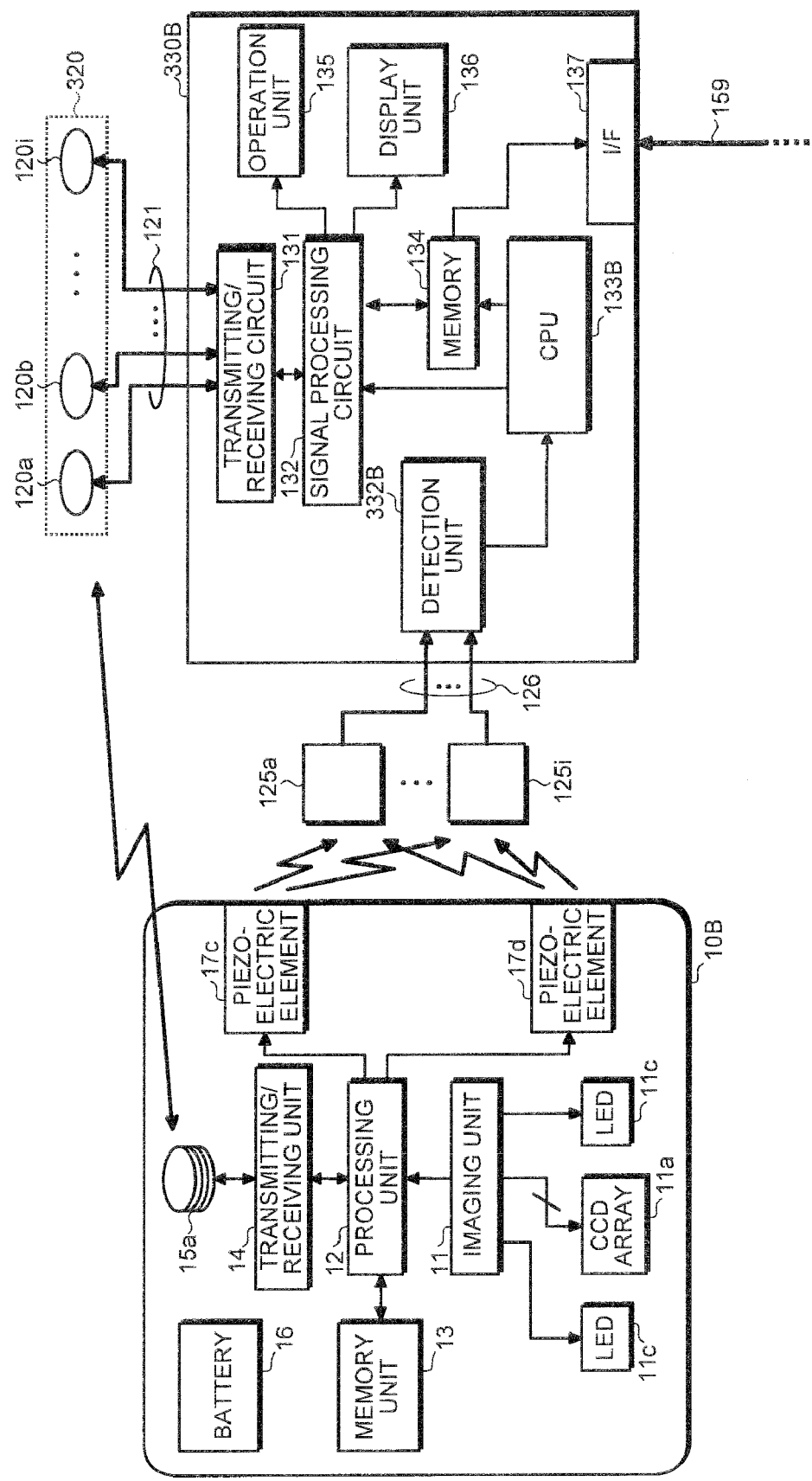
FIG. 43 is a block diagram showing a schematic configuration example of a capsule medical device and a receiving device according to the modification 3-2 of the third embodiment.

FIG. 42 is a schematic diagram showing a schematic configuration of a medical system 3B according to the modification 3-2. FIG. 43 is a block diagram showing a schematic configuration example of the capsule medical device 10B and a receiving device 330B according to the modification 3-2. In the modification 3-2, the capsule medical device 10B in the modification 1-2 is used. The capsule medical device 10B has, as a signal source, the piezoelectric elements 17c and 17d generating an ultrasonic wave propagating in the subject 900 and reaching the outer surface.

As shown in FIG. 42, in the medical system 3B, as compared with the medical system 3 shown in FIG. 36, the capsule medical device 10 is replaced with the capsule medical device 10B, and the receiving device 330 is replaced with the receiving device 330B. The receiving device 330B is mounted, for example, on the floor or the like so as not to move like the receiving device 330. Near the face which comes into contact with the subject 900 in the bed 341, acoustic sensors 125a to 125i connected to the receiving device 330B via the cable 126.

As shown in FIG. 43, in the receiving device 330B, in a configuration similar to that of the receiving device 330 shown in FIG. 37, the CPU 133 is replaced with the CPU 133B. Further, the receiving device 330B has a signal detection unit 332B for reading, as a detection signal, a potential change which occurs in any of the acoustic sensors 125a to 125i as a detection signal.

The signal detection unit 332B reads, as a detection signal, a potential change occurring in each of the acoustic sensors 125a to 125i via the cable 126, executes a predetermined process such as frequency separation or FET and, after that, supplies the processed detection signal as orientation data to the CPU 133B.

Like the CPU 133 in the foregoing first embodiment, the CPU 133B functions as orientation specifying means specifying the orientation of the capsule medical device 10B (that is, tilt of the specified direction Ui) with respect to the reference direction Dg from the strength and orientation of the sign (ultrasonic wave) for orientation detection observed at the observation points (the acoustic sensors 125a to 125i). That is, the CPU 133B estimates the spatial spread of the ultrasonic wave (ultrasound distribution) from the strength, phase, and the like of detection signals at the acoustic sensors 125a to 125i supplied from the signal detection circuit 332B and specifies the orientation with respect to the reference direction Dg of the capsule medical device 10B (that is, the orientation with respect to the reference direction Dg of the specified direction Ui) from arrangement of the piezoelectric elements 17c and 17d. In a manner similar to the foregoing embodiments, information of the orientation (orientation data) with respect to the reference direction Dg of the specified direction Ui specified by the CPU 133B is temporarily stored in association with image data received simultaneously or around the same time from the capsule medical device 10B into the memory 134.

In such a manner, in the modification 3-2, by fixing the acoustic sensors 125a to 125i as the observation points in the real space, orientation data indicative of the orientation of the specified direction Ui with respect to the reference direction Dg which is set for the real space is generated. The other configuration is similar to that of any of the foregoing embodiments (including their modifications). Since the operation of the medical system 3B according to the embodiment is similar to that of the modification 1-2, the detailed description will not be repeated.

With the configuration and operation as described above, in the modification 3-2, in a manner similar to the first embodiment, the orientations of a plurality of pieces of image data can be aligned by performing the rotation correction on image data on the basis of the orientation with respect to the reference direction Dg of the capsule medical device 10B at the time of imaging, so that the medical system 3B and the image processing method enabling reduced time and effort on diagnosis and improved accuracy of a diagnosis result can be realized.

Also in the modification 3-2, in a manner similar the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Fourth Embodiment

Although the case of disposing the signal source (antenna 15a) in the capsule medical device 10 and fixing the observation points (antennas 120) in the real space has been described as an example in the third embodiment, the invention is not limited to the case. It is also possible to fix the signal source in the real space and dispose the observation points in the capsule medical device. In the following, the case will be described in detail as a fourth embodiment with reference to the drawings. In the following description, the same reference numerals are designated to components similar to those of the forgoing embodiment and its modifications for simplicity of explanation, and their detailed description will not be repeated.

Figure 44:
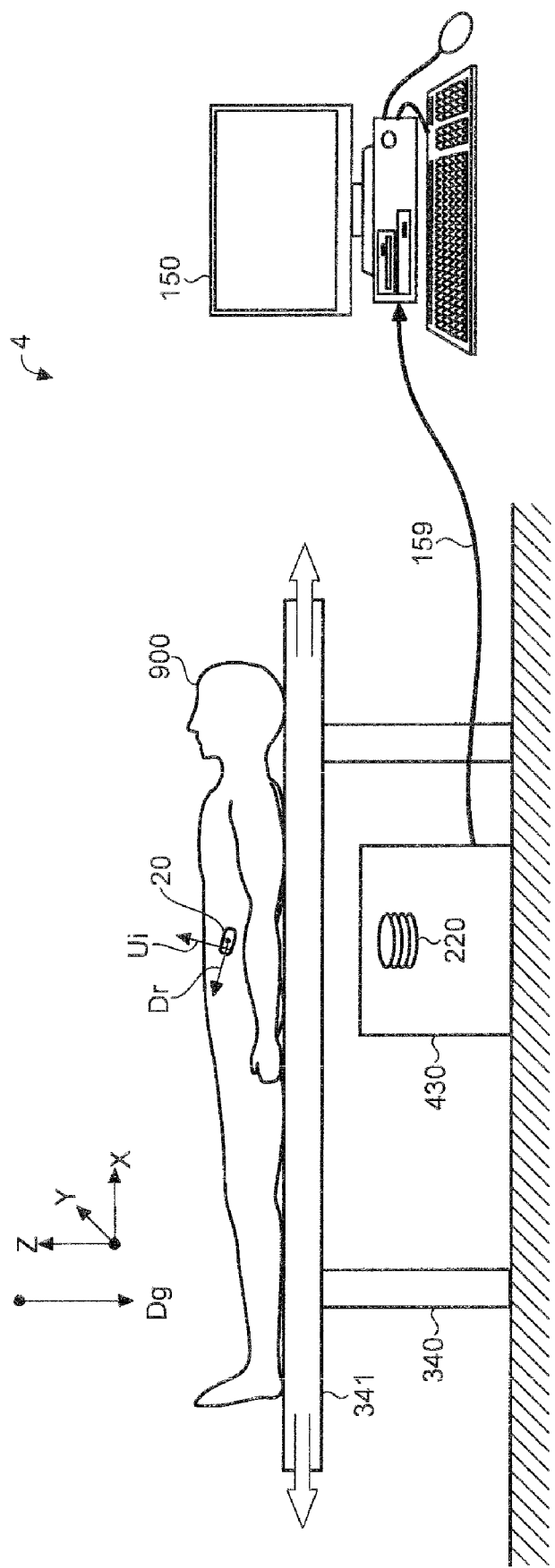
FIG. 44 is a schematic diagram showing a schematic configuration of a medical system according to a fourth embodiment.
Figure 45:
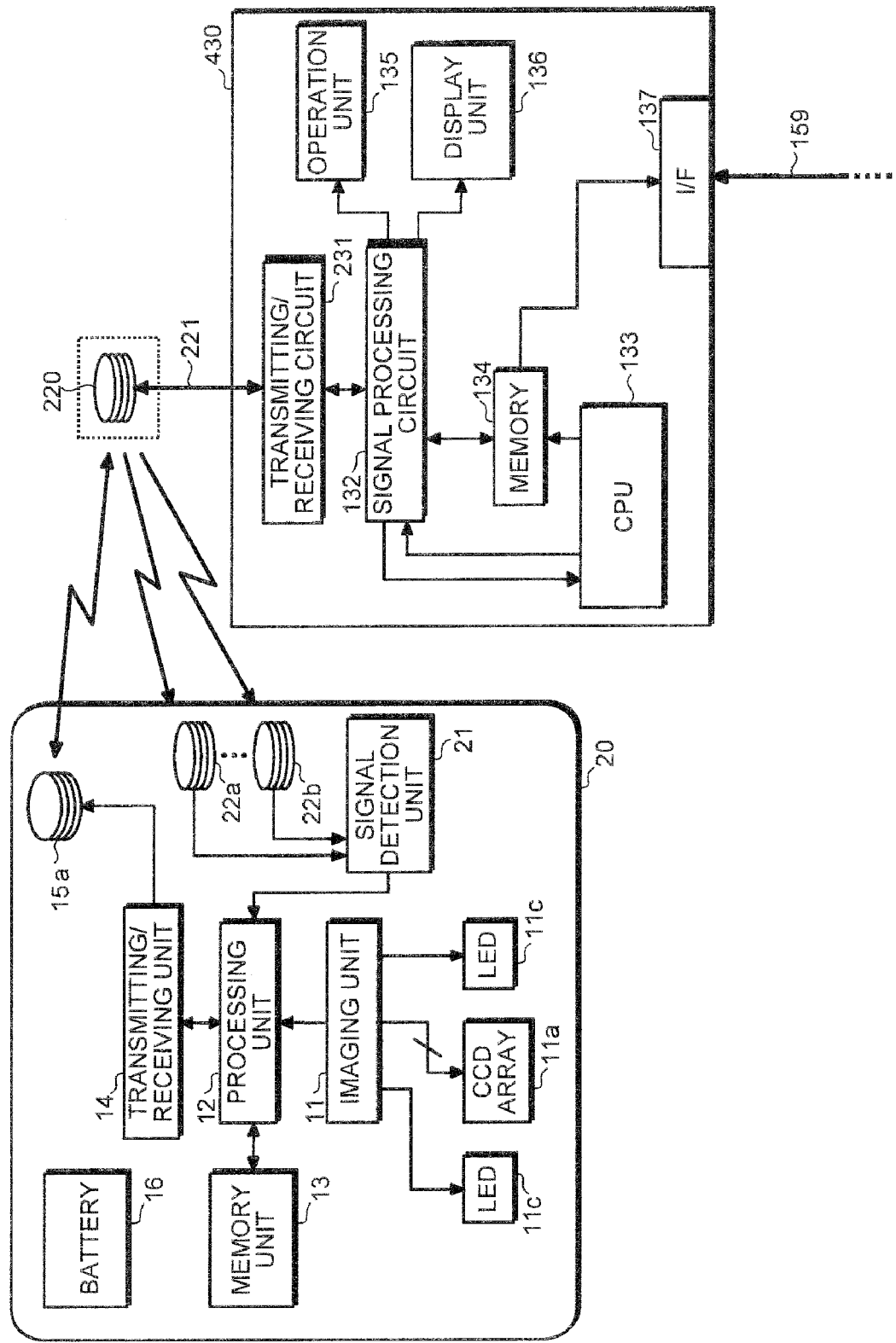
FIG. 45 is a block diagram showing a schematic configuration example of a capsule medical device and a receiving device according to the fourth embodiment.

FIG. 44 is a schematic diagram showing a schematic configuration of a medical system 4 according to the fourth embodiment. FIG. 45 is a block diagram showing an example of a schematic configuration of the capsule medical device 20 and a receiving device 430 according to the fourth embodiment. In the fourth embodiment, the capsule medical device 20 according to the second embodiment is used. The capsule medical device 20 has the plurality of antennas 22a and 22b.

As illustrated in FIG. 44, in the medical system 4, in comparison with the medical system 2 shown in FIG. 24, the receiving device 230 is replaced with the receiving device 430. The receiving device 430 is mounted on, for example, the floor so as not to move. The space including the floor is real space in which a reference direction Dg is set in the fourth embodiment. Further, the medical system 4 has a sensor stand mounted on the floor surface so as not to move, the bed 341 on which the subject 900 lies, and the movable stage 340 supporting the bed 341 so as to be movable in the horizontal direction. The bed 341 may be fixed to the floor surface so as not to move.

As shown in FIG. 45, the receiving device 430 has a configuration similar to that of the receiving device 230 shown in FIG. 25. The antennas 220 connected to the receiving device 430 via the cable 221 are, for example, disposed on the sensor stand fixed to the receiving device 430 so as not to move relative to the floor surface. The sensor stand 320 is mounted so that the face on which the antennas 220 are arranged faces the rear face of the bed 341. That is, the sensor stand 320 is mounted below the bed 341 in a state where the face on which the antennas 220 are arranged faces upward. The invention, however, is not limited to the arrangement but can be variously modified to, for example, a case where the antennas 220 are disposed in the bed 341 so as to be arranged on the mount face or the rear face of the bed 341.

By making the bed 341 horizontally movable, particularly, horizontally movable with respect to the sensor stand 320, the position of the subject 900 relative to the antennas 220, that is, the position of the capsule medical device 20 can be properly adjusted. Thus, the orientation of the capsule medical device 20 can be specified with higher precision.

As described above, in the fourth embodiment, by fixing the antenna 220 as the signal source in the real space, orientation data indicative of the orientation of the specified direction Ui with respect to the reference direction Dg set in the real space is generated. The other configuration is similar to that of any of the first embodiment (including its modifications), the second embodiment (including its modifications), and the third embodiment (including its modifications). Since the operation of the medical system 4 according to the embodiment is similar to that of the second embodiment, the detailed description will not be repeated.

With the configuration and operation as described above, in the fourth embodiment, in a manner similar to the first embodiment, the orientations of a plurality of pieces of image data can be aligned by performing the rotation correction on image data on the basis of the orientation with respect to the reference direction Dg of the capsule medical device 20 at the time of imaging, so that the medical system 4 and the image processing method enabling reduced time and effort on diagnosis and improved accuracy of a diagnosis result can be realized.

Also in the fourth embodiment, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Modification 4-1

Although the case of using the electromagnetic wave generating source (antenna 220) as the signal source has been described as an example in the medical system 4 according to the fourth embodiment, the invention is not limited to the case but a magnetic field generating source can be used as the signal source. The case will be described in detail below as modification 4-1 of the fourth embodiment with reference to the drawings. In the following description, the case of specifying the orientation of the capsule medical device 20A by a so-called active method of supplying a signal (drive signal) of the resonance frequency to the LC resonance circuit 222 fixed in the real space to make the LC resonance circuit 222 generate an induced magnetic field will be taken as an example. In the following description, the same reference numerals are designated to components similar to those of any of the foregoing embodiments and their modifications for simplicity of explanation, and their detailed description will not be repeated.

Figure 46:
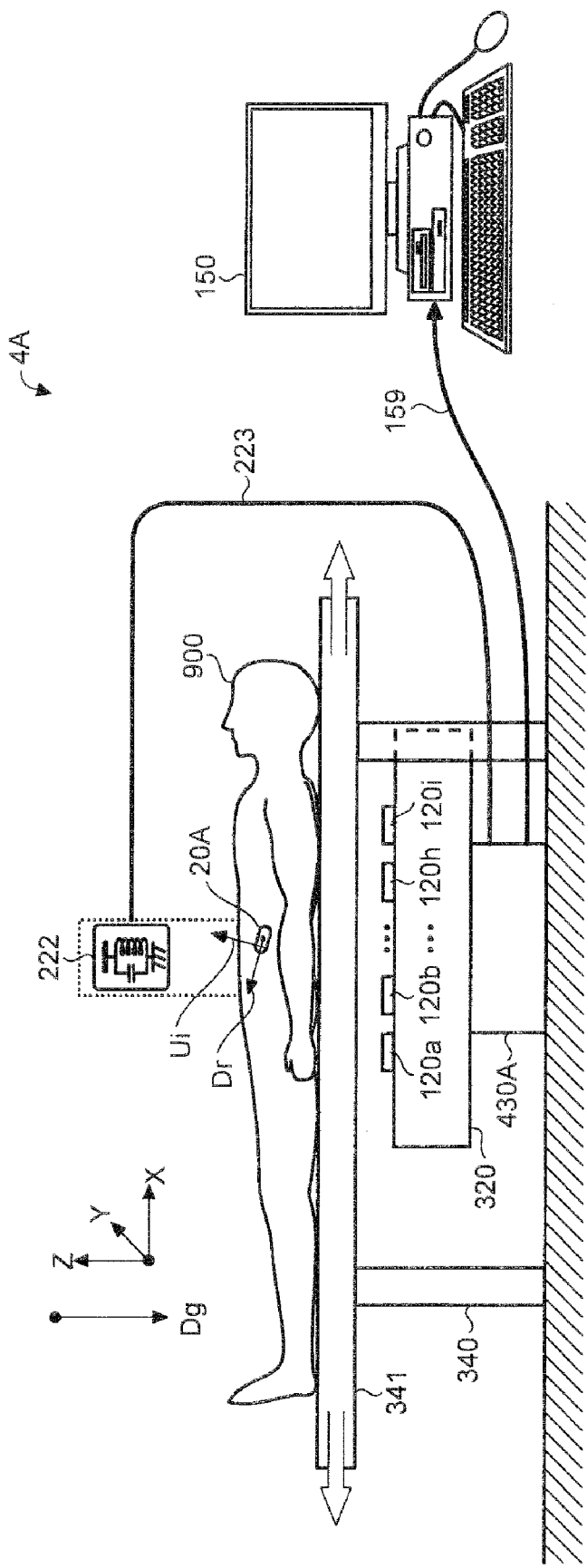
FIG. 46 is a schematic diagram showing a schematic configuration of a medical system according to modification 4-1 of the fourth embodiment.
Figure 47:
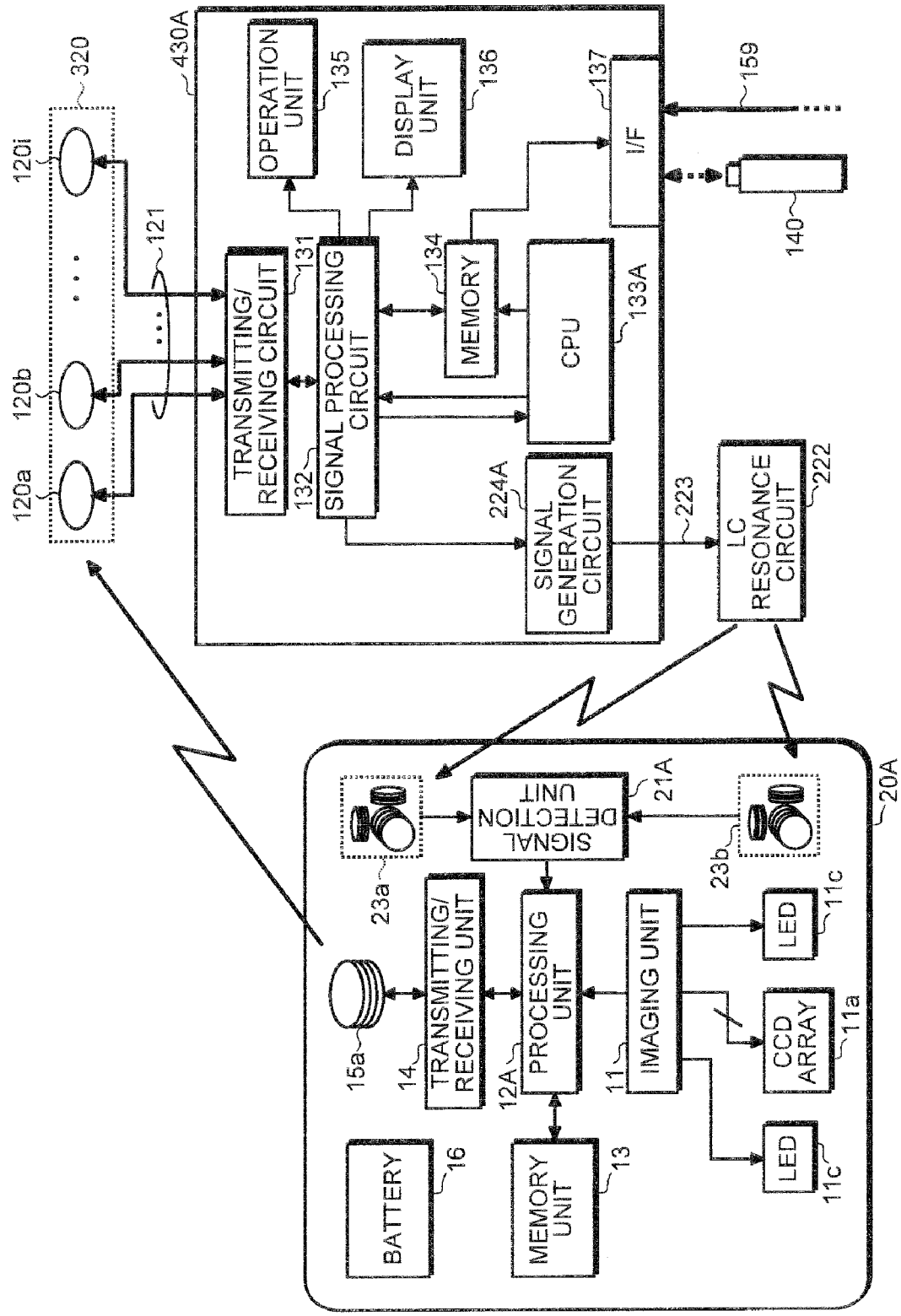
FIG. 47 is a block diagram showing a schematic configuration example of a capsule medical device and a receiving device according to the modification 4-1 of the fourth embodiment.

FIG. 46 is a schematic diagram showing a schematic configuration of a medical system 4A according to the modification 4-1. FIG. 47 is a block diagram showing a schematic configuration example of the capsule medical device 20A and a receiving device 430A in the modification 4-1. In the modification 4-1, the capsule medical device 20A in the modification 2-1 is used. The capsule medical device 20A has a plurality of magnetic sensors 23a and 23b as observation points.

As shown in FIG. 46, in the medical system 4A, as compared with the medical system 4 shown in FIG. 44, the capsule medical device 20 is replaced with the capsule medical device 20A, the receiving device 430 is replaced with the receiving device 430A, and the antenna 220 of the receiving device 430 is replaced with the sensor stand 320 and the antenna 120. The receiving device 430A is mounted, for example, on the floor or the like so as not to move. To the bed 341, the LC resonance circuit 222 as the signal source is fixed. The LC resonance circuit 222 is connected to the receiving device 430A via the cable 223.

As shown in FIG. 47, the receiving device 430A has, in addition to the configuration similar to that of the receiving device 430 shown in FIG. 45, a signal generation circuit 224A. In the receiving device 430A, in a configuration similar to the receiving device 430 shown in FIG. 45, the antenna 220 and the transmitting/receiving circuit 231 are replaced with the antenna 120 and the transmitting/receiving circuit 131, and the CPU 133 is replaced with the CPU 133A. That is, the receiving device 430A has a configuration almost similar to that of the receiving device 230A in the modification 2-1 except for the point that the antenna 120 and the LC resonance circuit 222 are fixed to the sensor stand 320, the bed 341, and the like.

That is, the CPU 133A specifies the orientation with respect to the reference direction Dg of the capsule medical device 20A (that is, the tilt of the specified direction Ui) by using the signal detection data added to the image data from the capsule medical device 20A.

In such a manner, in the modification 4-1, by fixing the LC resonance circuit 222 as the signal source in the real space, orientation data indicative of the orientation of the specified direction Ui with respect to the reference direction Dg which is set for the real space is generated. The other configuration is similar to that of any of the foregoing embodiments (including their modifications). Since the operation of the medical system 4A according to the modification 4-1 is similar to that of the modification 2-1, the detailed description will not be repeated.

With the configuration and operation as described above, in the modification 4-1, in a manner similar to the first embodiment, the orientations of a plurality of pieces of image data can be aligned by performing the rotation correction on image data on the basis of the orientation with respect to the reference direction Dg of the capsule medical device 20A at the time of imaging, so that the medical system 4A and the image processing method enabling reduced time and effort on diagnosis and improved accuracy of a diagnosis result can be realized.

Also in the modification 4-1, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Modification 4-2

As the signal source in the fourth embodiment, an ultrasound generation source can be also used. This case will be described in detail below as modification 4-2 of the fourth embodiment with reference to the drawings. In the following description, the same reference numerals are designated to components similar to those of any of the foregoing embodiments and their modifications for simplicity of explanation, and their detailed description will not be repeated.

Figure 48:
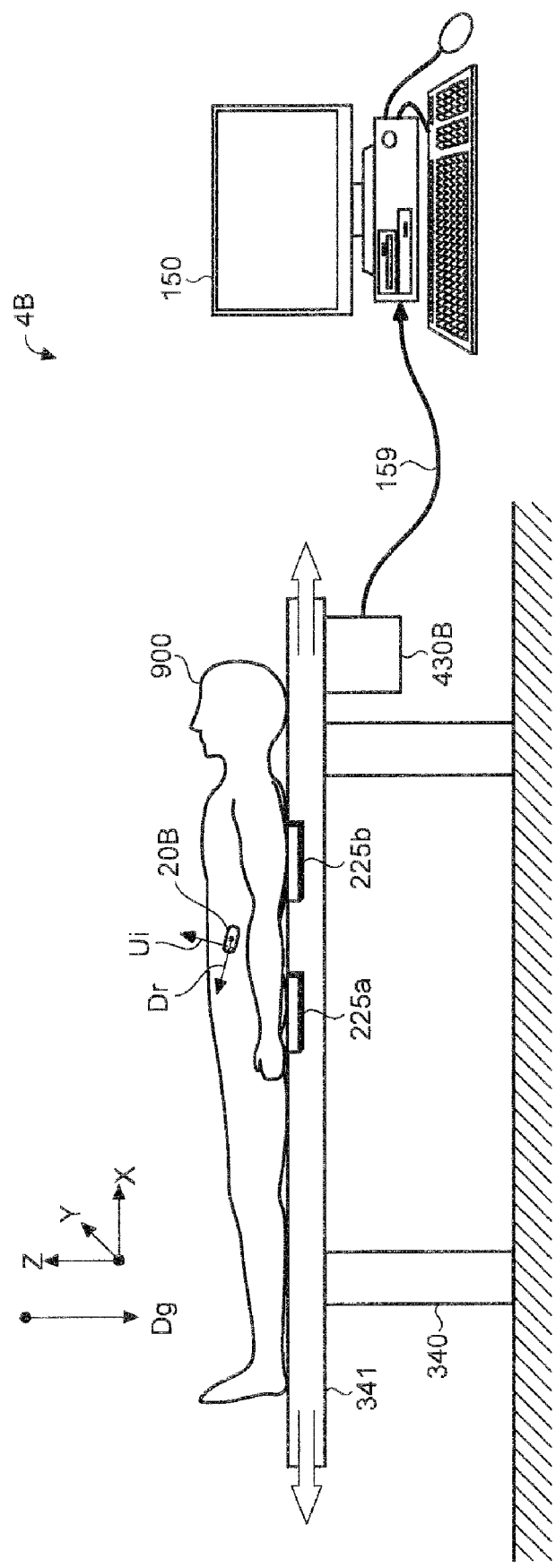
FIG. 48 is a schematic diagram showing a schematic configuration of a medical system according to modification 4-2 of the fourth embodiment.
Figure 49:
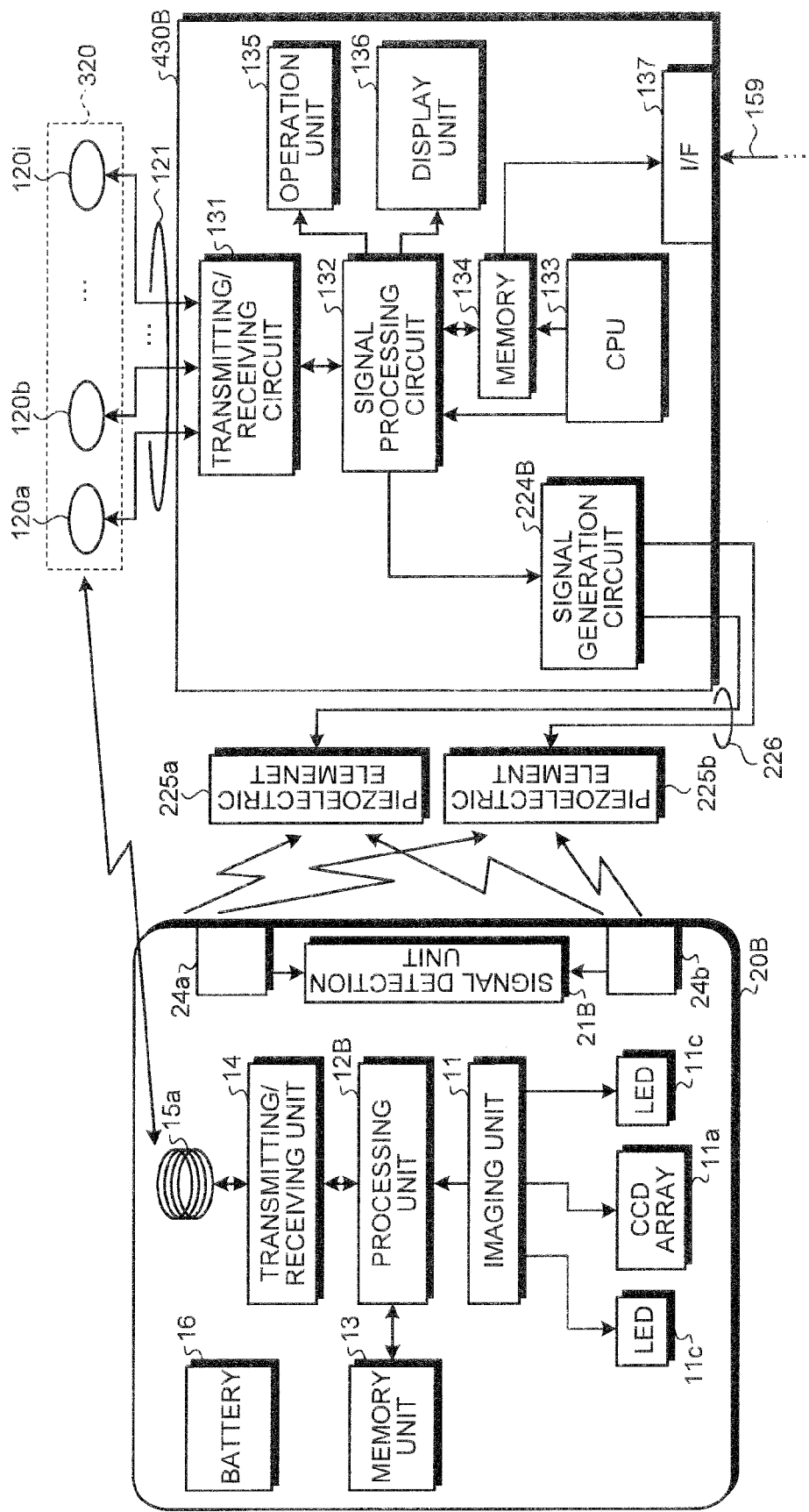
FIG. 49 is a block diagram showing a schematic configuration example of a capsule medical device and a receiving device according to the modification 4-2 of the fourth embodiment.

FIG. 48 is a schematic diagram showing a schematic configuration of a medical system 4B according to the modification 4-2. FIG. 49 is a block diagram showing a schematic configuration example of the capsule medical device 20B and a receiving device 430B according to the modification 4-2. In the modification 4-2, the capsule medical device 20B in the modification 2-2 is used. The capsule medical device 20B has a plurality of acoustic sensors 24a and 24b as observation points.

As shown in FIG. 48, in the medical system 4B, as compared with the medical system 4 shown in FIG. 44, the capsule medical device 20 is replaced with the capsule medical device 20B, and the receiving device 430 is replaced with the receiving device 430B, and the antenna 220 of the receiving device 430 is replaced with the sensor stand 320 and the antenna 120. The receiving device 430B is mounted, for example, on the floor or the like so as not to move. Near the face which comes into contact with the subject 900 in the bed 341, a plurality of piezoelectric elements 225a and 225b connected to the receiving device 430B via the cable 226 (refer to FIG. 49) are disposed.

As shown in FIG. 48, the receiving device 430B has, in addition to a configuration similar to that of the receiving device 430 shown in FIG. 45, the signal generation circuit 224B. In the receiving device 430B, in a configuration similar to that of the receiving device 430 shown in FIG. 45, the antenna 220 and the transmitting/receiving circuit 231 are replaced with the antenna 120 and the transmitting/receiving circuit 131, respectively. That is, the receiving device 430B has a configuration similar to that of the receiving device 230B according to the modification 2-2 except for the point that the antenna 120 and the LC resonance circuit are fixed to the sensor stand 320, the bed 341, and the like.

Therefore, the CPU 133 specifies the orientation with respect to the reference direction Dg of the capsule medical device 20B (that is, the tilt of the specified direction Ui) by using the signal detection data added to the image data from the capsule medical device 20B.

In such a manner, in the modification 4-2, by fixing the plurality of piezoelectric elements 225a and 225b as a signal source in the real space, orientation data indicative of the orientation of the specified direction Ui with respect to the reference direction Dg which is set for the real space is generated. The other configuration is similar to that of any of the foregoing embodiments (including their modifications). Since the operation of the medical system 4E according to the modification 4-2 is similar to that of the modification 2-2, the detailed description will not be repeated.

With the configuration and operation as described above, in the modification 4-2, in a manner similar to the first embodiment, the orientations of a plurality of pieces of image data can be aligned by performing the rotation correction on image data on the basis of the orientation with respect to the reference direction Dg of the capsule medical device 20B at the time of imaging, so that the medical system 4B and the image processing method enabling reduced time and effort on diagnosis and improved accuracy of a diagnosis result can be realized.

Also in the modification 4-2, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Fifth Embodiment

Although a configuration of generating any signal, such as the antenna 220, the LC resonance circuit 222, the piezoelectric elements 225a and 225b disposing any signal source is used as the signal source fixed in the real space in the fourth embodiment (including its modifications), the invention is not limited to the configuration. A physical phenomenon existing in the real space such as gravity, geomagnetism, or the like may be used. In the following, the case of using gravity in place of the signal source will be described in detail with reference to the drawings. In the following description, the same reference numerals are designated to components similar to those of the forgoing embodiment and its modifications for simplicity of explanation, and their detailed description will not be repeated.

Figure 50:
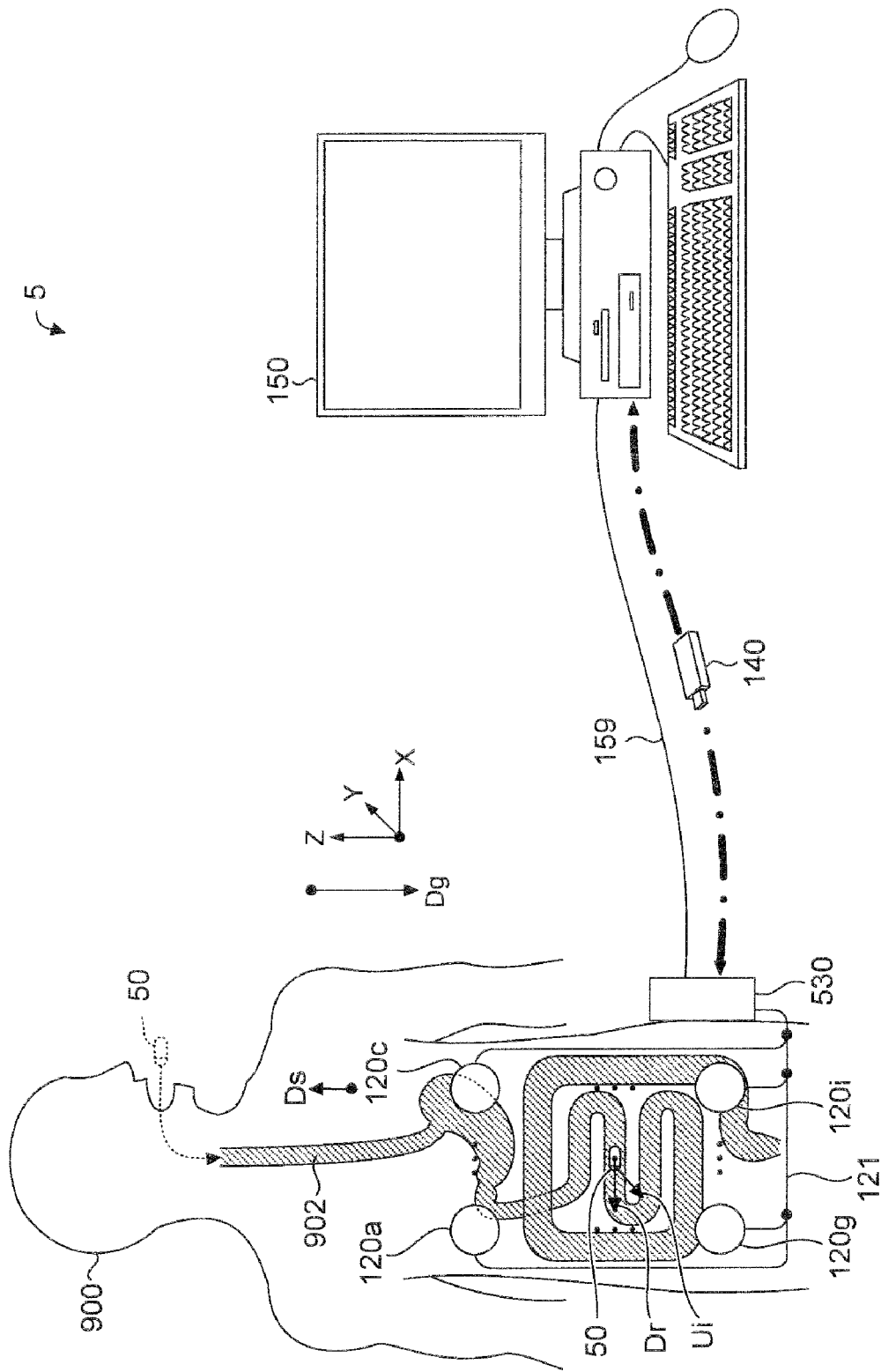
FIG. 50 is a schematic diagram showing a schematic configuration of a medical system according to a fifth embodiment.
Figure 51:
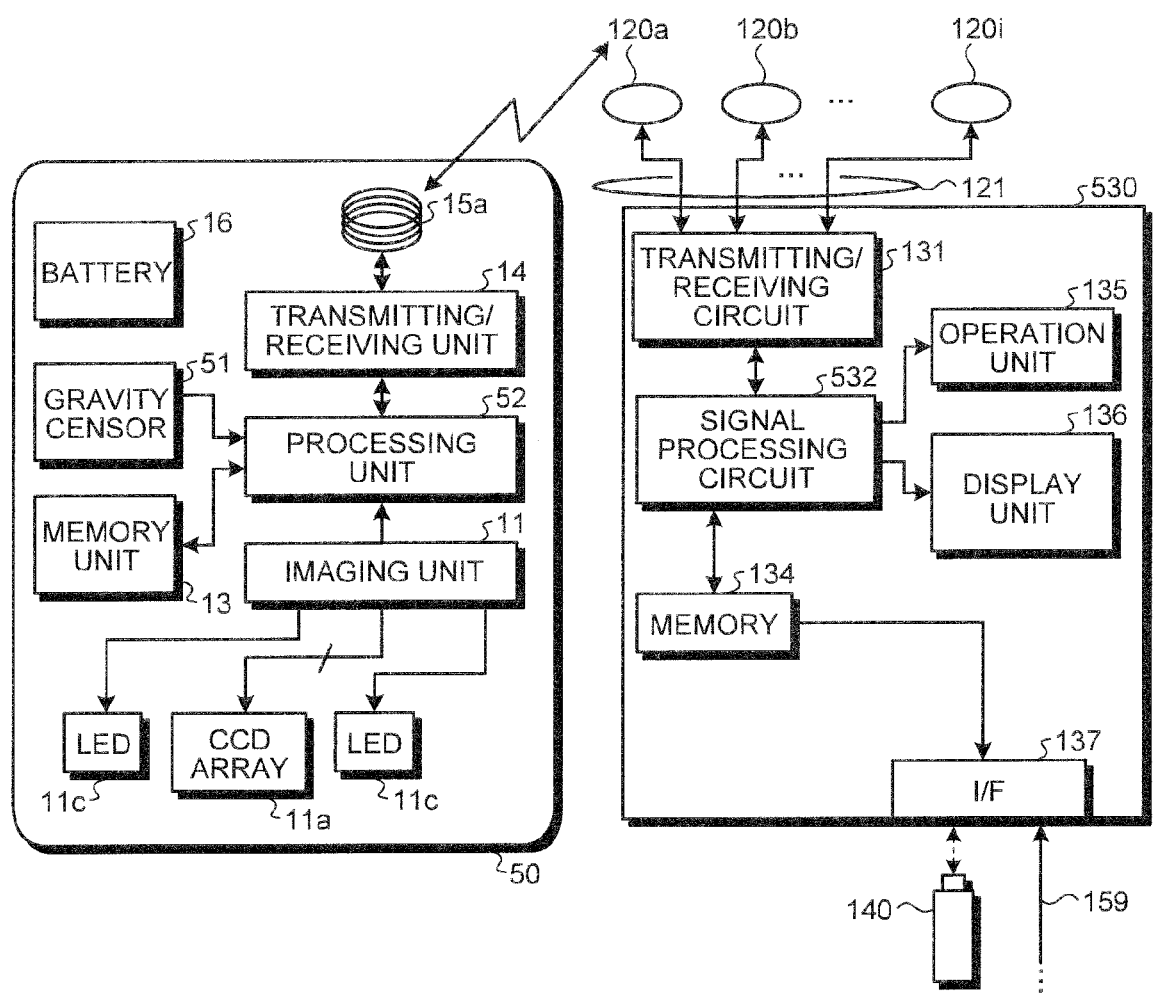
FIG. 51 is a block diagram showing a schematic configuration example of a capsule medical device and a receiving device according to the fifth embodiment.

FIG. 50 is a schematic diagram showing a schematic configuration of a medical system S according to the fifth embodiment. FIG. 51 is a block diagram showing an example of a schematic configuration of a capsule medical device 50 and a receiving device 530 according to the fifth embodiment.

As shown in FIG. 50, in the medical system 5, in comparison with the medical system 1 shown in FIG. 1, the capsule medical device 10 is replaced with the capsule medical device 50, and the receiving device 130 is replaced with the receiving device 530.

As shown in FIG. 51, the capsule medical device 50 has, in addition to a configuration similar to that of the capsule medical device 10 shown in FIG. 5, a gravity sensor 51.

The gravity sensor 51 is gravity direction detecting means for detecting the direction of gravity. Any acceleration sensor which can detect gravity and is small enough to be housed in the capsule medical device 50 such as a mechanical acceleration sensor using a coil, a spring, a plate, or the like, a semiconductor-type acceleration sensor using the Micro Electro Mechanical Systems (MEMS) technique, or the like may be used.

A processing unit 52 reads a voltage change occurring in the gravity sensor 51 as a detection signal and executes a predetermined process on the detection signal. The processing unit 52 adds, as orientation data, the detection signal subjected to the signal process to image data obtained at the same time or around the same time.

As the orientation data, data expressing the direction of gravity using the capsule medical device 50 as a reference by a vector can be used. By using the data expressing the direction of gravity by a vector (orientation data), the orientation of the capsule medical device 50 with respect to the reference direction Dg (that is, the orientation of the specified direction Ui with respect to the reference direction Dg) can be directly derived.

The present invention is not limited to the case. For example, by setting one of three axes of the gravity sensor in a direction perpendicular to the light reception face, a gravity sensor of two axes without the axis can be used as the gravity sensor 51. To the image data, a time stamp is also added in a manner similar to the first embodiment. The image data to which the signal detection data and the time stamp are added is transmitted by radio from the processing unit 52 via the transmitting/receiving unit 14 from the antenna 15a to the receiving device 530.

On the other hand, in the receiving device 530, as shown in FIG. 51, in a configuration similar to that of the receiving device 130 shown in FIG. 5, the signal processing circuit 132 is replaced with a signal processing circuit 532.

In the fifth embodiment, as described above, to image data received from the capsule medical device 50, the vector of the direction of gravity detected by the gravity sensor 51 is added as the orientation data. Therefore, in the fifth embodiment, the signal processing circuit 532 temporarily buffers the image data to which the input orientation data and the time stamp are added in the memory 134 or the like and, after that, transmits the image data as it is to the display device 150 via the interface 137.

As described above, in the fifth embodiment, the gravity which is stable in the real space is used as the sign for orientation detection, the gravity sensor 51 as the measurement point is disposed in the capsule medical device 50, and the orientation data indicative of the orientation with respect to the reference direction Ds of the specified direction Ui is generated on the basis of the vector of the direction of gravity measured by the gravity sensor 51. The other configuration is similar to that of any of the foregoing embodiments (including their modifications).

Figure 52:
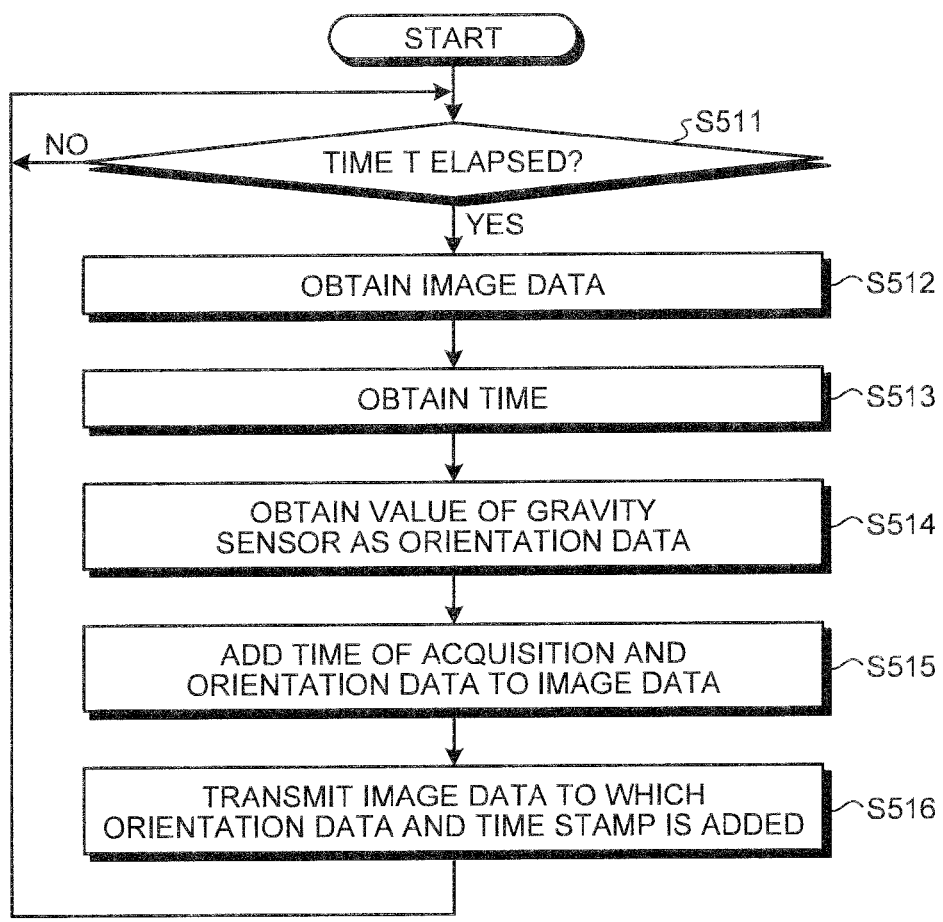
FIG. 52 is a flowchart showing a schematic configuration example of the capsule medical device according to the fifth embodiment.
Figure 53:
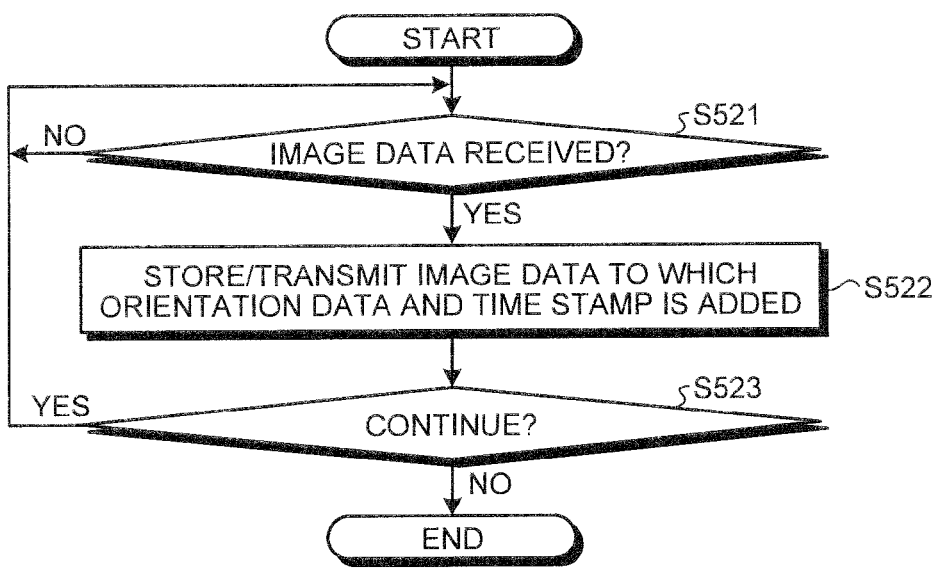
FIG. 53 is a flowchart showing an example of outline operation of the receiving device according to the fifth embodiment.

Next, the operation of the medical system 5 according to the fifth embodiment will now be described in detail with reference to the drawings. Since the operation of the display device 150 in the fifth embodiment is similar to that of the first embodiment, in the explanation, the operation of the capsule medical device 50 and the receiving device 530 will be described below. FIG. 52 is a flowchart showing an example of schematic operation of the capsule medical device 50 according to the fifth embodiment. FIG. 53 is a flowchart showing an example of schematic operation of the receiving device 530 according to the fifth embodiment.

As shown in FIG. 52, after startup, the capsule medical device 50 executes imaging operation periodically (for example, at time T (=0.5 second) intervals), thereby obtaining image data (steps S511 to S512). Subsequently, the capsule medical device 50 obtains time at which the image data is obtained (step S513). The capsule medical device 50 obtains a value detected by the gravity sensor 51 as orientation data (step S514). Subsequently, the capsule medical device 50 adds the obtained time as a time stamp to the image data and adds the obtained orientation data to the image data (step S515). Next, the capsule medical device 50 transmits, as a wireless signal, the image data to which the time stamp and the orientation data is added (step S516), and returns to the step S511. By such operation, the image data to which the time stamp and the orientation data is added is periodically transmitted by radio from the capsule medical device 50 to the receiving device 530. The operation of the capsule medical device 50 shown in FIG. 52 is continued until no power remains in the battery 16 in the capsule medical device 50.

On the other hand, as shown in FIG. 53, the receiving device 530, for example, always or periodically, monitors whether image data is received from the capsule medical device 50 (No in step S521). In the case where image data is received (Yes in step S521), the receiving device 530 temporarily buffers the received image data in the memory 134 or the like and, after that, either stores the image data into the portable recording medium 140 from the interface 137 or transmits the image data from the interface 137 to the display device 150 via the communication cable 159 (step S522). After that, the receiving device 530 determines whether the operation is continued, for example, whether an operation end instruction is received from the operation unit 135 (step S523). In the case of continuing the operation (Yes in step S523), the receiving device 530 returns to step S521 and repeats waiting of reception of image data. On the other hand, in the case where the operation is not continued (No in step S523), the operation is finished.

With the configuration and operation as described above, in the fifth embodiment, in a manner similar to the first embodiment, the orientations of a plurality of pieces of image data can be aligned by performing the rotation correction on image data on the basis of the orientation with respect to the reference direction Ds (gravity direction) of the capsule medical device 50 at the time of imaging, so that the medical system 5 and the image processing method enabling reduced time and effort on diagnosis and improved accuracy of a diagnosis result can be realized.

In the fifth embodiment, in the case of setting the reference direction Dg in the real space, the gravity can be used in place of the sign for orientation detection. As a result, using the gravity sensor 51 capable of detecting the gravity as almost the absolute reference which is not influenced by the posture and orientation of the subject 900, the orientation of the specified direction Ui with respect to the reference direction Dg can be detected directly. Thus, the configuration for orientation detection can be simplified, and the process in the receiving device 530 which will be described later can be lessened.

Also in the fifth embodiment, in a manner similar to the first embodiment (including its modifications) and the second embodiment (including its modifications), the reference direction Ds set for the subject 900 and the specified direction Ui can be made coincide with each other. It can be realized that, for example, by manually entering the posture of the subject 900 by the observer or by providing the subject 900 with a gravity sensor and performing automatic detection, a tilt (rotation amount) between the reference direction Ds set for the subject 900 and the reference direction Dg is obtained and, using the tilt (rotation amount) and the orientation (correction amount B) of the specified direction Ui with respect to the reference direction Dg, image data is rotation-corrected.

Sixth Embodiment

In the foregoing embodiments (including their modifications), the case of generating an image of the average color bar 60 from image data obtained by performing rotation correction on image data and assembling the generated average color bar 60 in a GUI screen (refer to FIG. 8) for providing the observer with the GUI function has been described. In the present invention, however, the image incorporated in the GUI screen is not limited to the average color bar 60. In the following, an image of a red detection result (hereinbelow, called a red indicator) will be taken as an example and will be described in detail as a sixth embodiment with reference to the drawings. In the following description, the sixth embodiment will be described using the first embodiment as a base. The invention, however, is not limited to the case. Obviously, the sixth embodiment can be applied to any of the foregoing embodiments and their modifications.

The red detection is detection of the region (width) and density of red in image data. Therefore, by visualizing a result of red detection on image data, the observer can visually recognize the amount and density of red included in the image data. By generating and displaying a GUI (red indicator) in which images of the red detection results are arranged along the time series of the image data), the observer can grasp a place where red appears most at a glance. As a result, the observer can easily find a region of bleeding, swelling, or the like.

Figure 54:
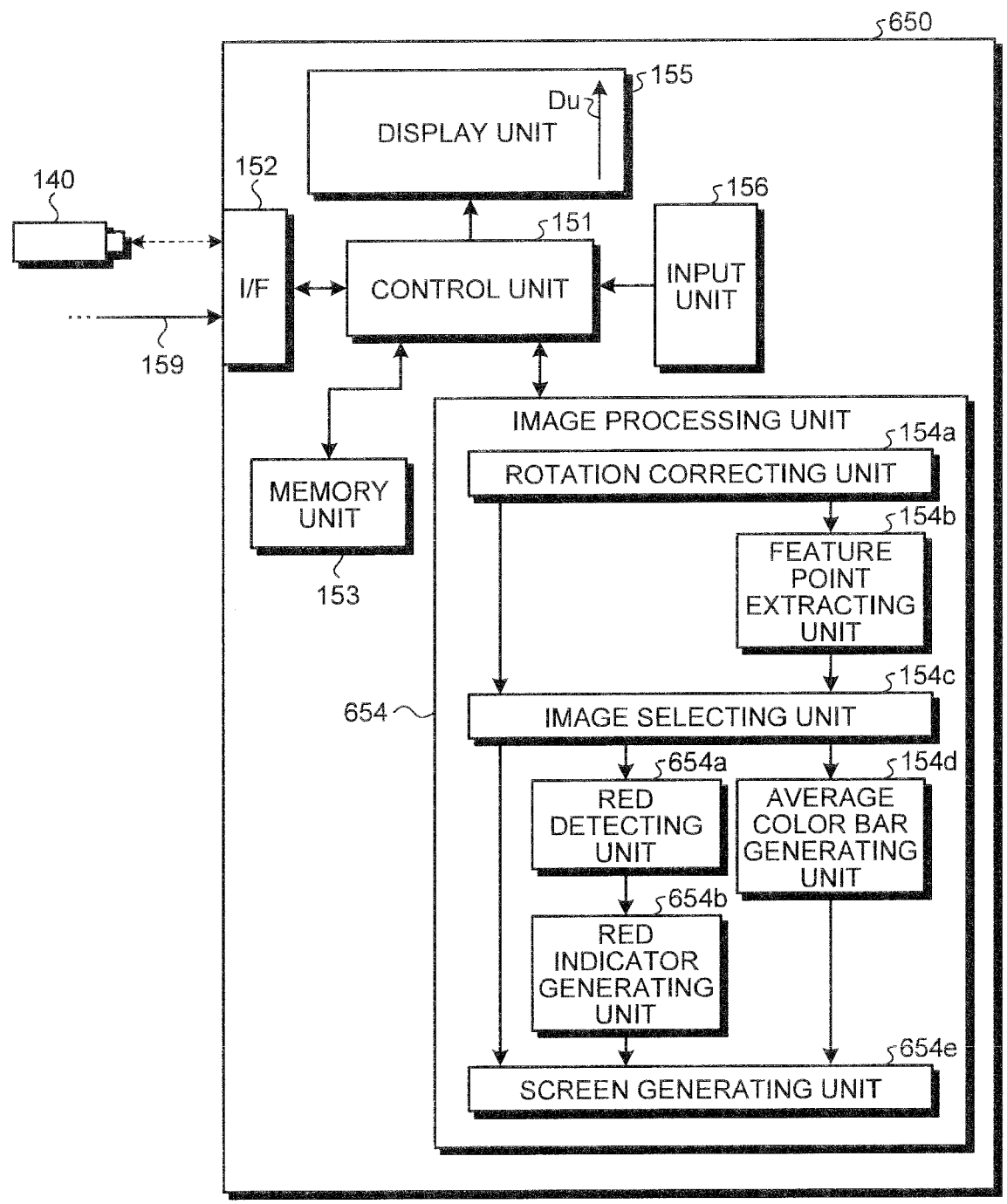
FIG. 54 is a block diagram showing an example of a schematic configuration of a display device according to a sixth embodiment.

A medical system according to the sixth embodiment is obtained by replacing the display device 150 (refer to FIG. 7) in the medical system 1 shown in FIG. 1 with a display device 650 shown in FIG. 54. FIG. 54 is a block diagram showing a schematic configuration example of the display device 650 according to the sixth embodiment. As obvious from comparison between FIGS. 54 and 7, in the display device 650, the image processing unit 154 in the display device 150 is replaced with an image processing unit 654.

As shown in FIG. 54, the image processing unit 654 has a configuration similar to that of the image processing unit 154 except that a red detecting unit 654a and a red indicator generating unit 654b are added and the screen generating unit 154e is replaced with a screen generating unit (screen generating means) 654e.

The red detecting unit 654a functions as red detecting means for detecting a red component included in image data subjected to rotation correction. Specifically, the red detecting unit 654a determines the amount and density red component included in image data subjected to the rotation correction selected by the image selecting unit 154c, and generates red data obtained by averaging them. The determination and averaging of the amount and density of the red component can be executed by using, for example, the value of the red component in the image data. The red detection may be performed in each of a plurality of (for example, four) division regions (for example, division regions A1 to A4) obtained, by dividing the image data.

The red data generated by the red detecting unit 654a is supplied as a red detection result to the red indicator generating unit 654b. The red indicator generating unit 654b is red image generating means for generating an image (red image) visually displaying a detection result of the red detecting unit 654a. In the embodiment, as a red image, a red indicator (refer to a red indicator 66 in FIG. 56) is used. Therefore, the red indicator generating unit 654b generates an image of the red indicator by using the red detection result and supplies the image to the screen generating unit 654e.

Figure 56:
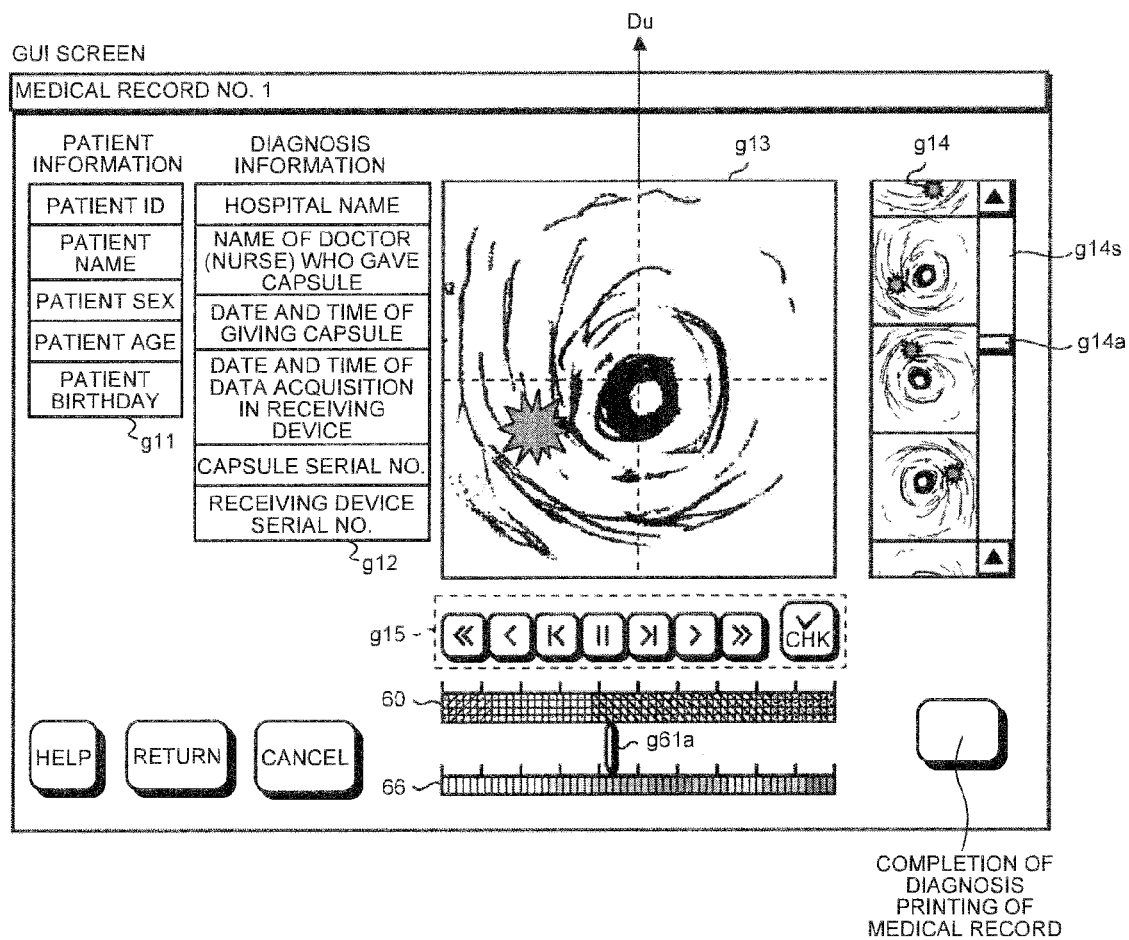
FIG. 56 is a diagram showing an example of a GUI screen generated by a screen generating unit according to the sixth embodiment.

The screen generating unit 654e generates a GUI screen as shown in FIG. 56 by using image data subjected rotation correction which is selected by the image selecting unit 154c, an image of the average color bar supplied from the average color bar generating unit 154d, and an image of the red indicator input from the red indicator generating unit 654b. The GUI screen generated according to the sixth embodiment will be described later.

Figure 55:
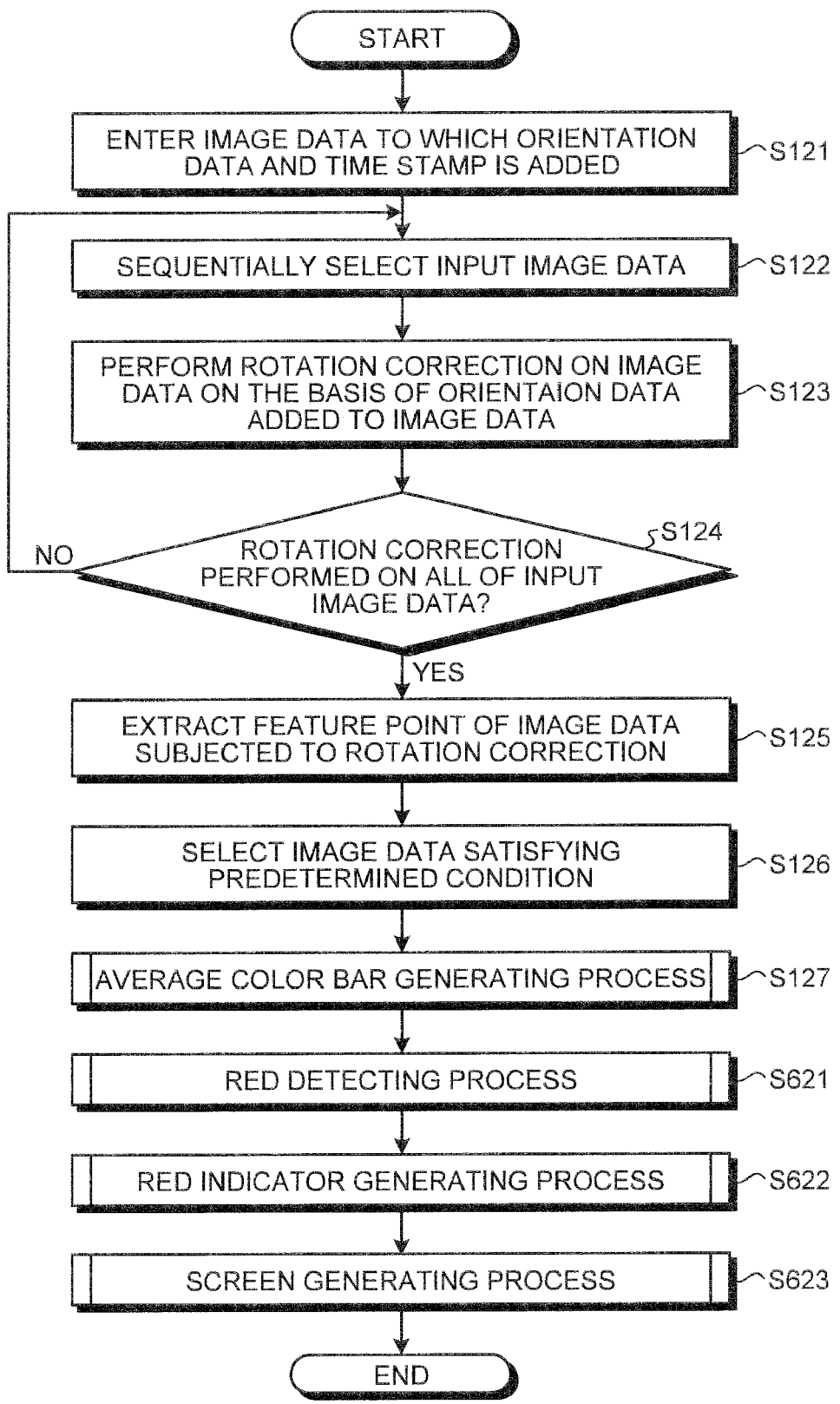
FIG. 55 is a flowchart showing an example of outline operation of the display device according to the sixth embodiment.

Using FIG. 55, the operation of the display device 650 according to the sixth embodiment will be described in detail. As shown in FIG. 55, first, the display device 650 takes steps similar to the steps described by using the steps S121 to S127 in FIG. 13 in the first embodiment, thereby executing the rotation correction on all of image data selected, and the process of generating an image of an average color bar. Next, the display device 650 executes a red detecting process in the red detecting unit 654a (step S621) and, subsequently, executes a process of generating an image of the red indicator from the red detection result in the red indicator generating unit 654b (step S622).

Next, the display device 650 makes the screen generating unit 654e execute the screen generating process for generating a GUI screen as shown in FIG. 56 by using the image data subjected to the rotation correction, selected in the image selecting unit 154c, the image of the average color bar supplied from the average color bar generating unit 154d, and an image of the red indicator supplied from the red indicator generating unit 654b (step S623) and, after that, finishes the process. The generated GUI screen is supplied to the display unit 155 via the control unit 151 and displayed to the observer. As a result, the observer is provided with the GUI function using the GUI screen and the input unit 156.

Using FIG. 56, the GUI screen generated by the screen generating unit 654e will be described in detail. As shown in FIG. 56, in the GUI screen generated by the screen generating unit 654e, like the GUI screen (refer to FIG. 8) generated by the screen generating unit 154e in the foregoing embodiments, patient information g11, diagnosis information g12, a main image display region g13, a sub image display region g14, a reproduction control button g15, and an average color bar 60 are incorporated. In the GUI screen, a red indicator 66 and a slider g61a indicative of the position on the average color bar 60 and the red indicator 66 in an image being displayed in the main image display region g13 while linking the average color bar 60 and the red indicator 66 are incorporated.

The length in the time base direction of the red indicator 66 is the same as that of the average color bar 60, and the red indicator 66 is disposed above or below the average color bar 60 in the screen. With the arrangement, the time base of the average color bar 60 and that of the red indicator 66 can be linked in appearance, so that it enables the observer to easily recognize a region in the average color bar 60, in which red appears often.

The color in a region corresponding to each of image data pieces in the red indicator 66 is graded according to the red detection result. Consequently, the observer can easily recognize a region in which red appears more often.

Modification 6-1

Figure 57:
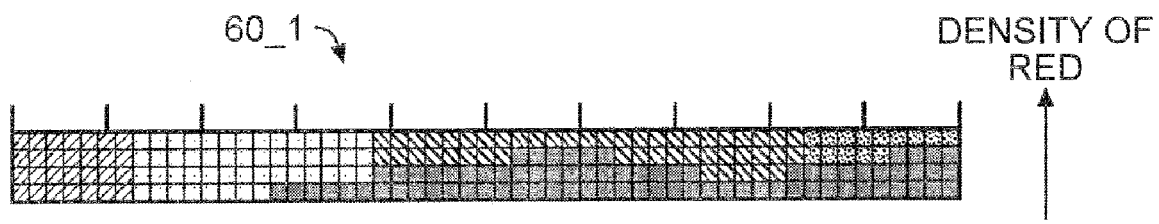
FIG. 57 is a diagram showing an example of an average color bar according to modification 6-1 of the sixth embodiment.

In the sixth embodiment, the case of visually displaying the red detection result by using the red indicator 66 (refer to FIG. 56) expressing the red detection result by a bar-shaped image has been described as an example. The present invention is not limited to the case but, for example, as shown in FIG. 57, the red detection result may be superimposed on the average color bar. FIG. 57 is a diagram showing an example of an average color bar 60_1 according to the modification 6-1 of the sixth embodiment. The average color bar 60_1 is obtained by superimposing an image expressing a red detection result by a histogram in the average color bar 60. Therefore, in the image of the red detection result, as shown in FIG. 57, the amount and density of red in image data is expressed by the height. The invention, however, is not limited to the expression. The red detection result may be expressed by a polygonal line.

For example, an image of the red detection result of image in which no red is detected or an average value of red data is smaller than a first threshold which is the minimum value is not drawn in the average color bar 60_1. An image of the red detection result of image data smaller than a second threshold as an intermediate value which is equal to or larger than the first threshold is superimposed in the lowest division region A1 in the corresponding image data part in the average color bar 60_1. Further, an image of the red detection result on image data in which the average value of red data is equal to or larger than the second threshold as the maximum value is superimposed in the entire corresponding image data part in the average color bar 60_1.

Modification 6-2

Figure 58:
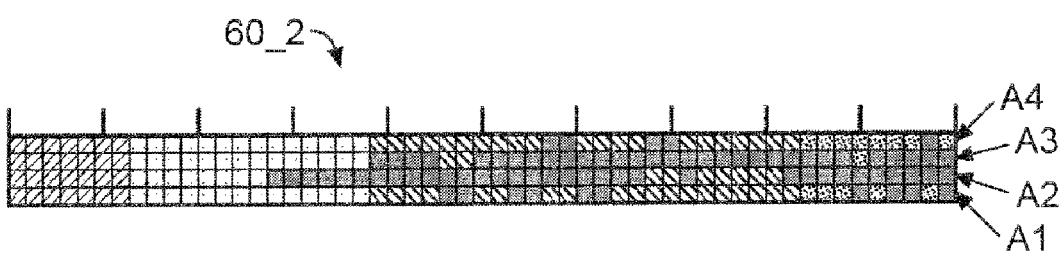
FIG. 58 is a diagram showing an example of an average color bar according to modification 6-2 of the sixth embodiment.

In the case of executing the red detection in each of the division regions A1 to A4 obtained by dividing image data into a plurality of (for example, four) pieces, images of the red detection results in the division regions A1 to A4 may be superimposed in an average color bar 602 in association with the division regions A1 to A4 dividing image data as shown in FIG. 58. With the arrangement, the observer can visually easily recognize a part in a region in which red is widely detected. FIG. 58 is a diagram showing an example of the average color bar 602 according to modification 6-2 of the sixth embodiment. The average color bar 60_2 is obtained by superimposing an image of the red detection result on the average color bar 60.

Modification 6-3

Figure 59:
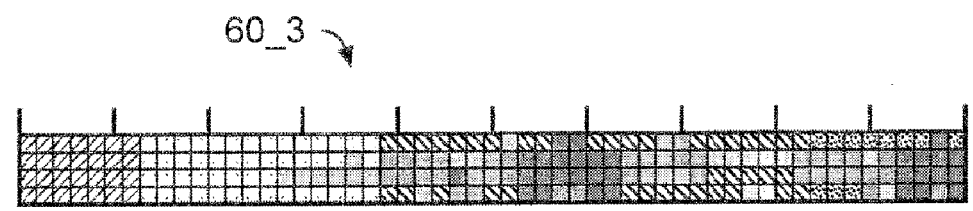
FIG. 59 is a diagram showing an example of an average color bar according to modification 6-3 of the sixth embodiment.

In the case of executing the red detection in each of the division regions A1 to A4 obtained by dividing image data into a plurality of (for example, four) pieces, images of the red detection results in the division regions A1 to A4 may be obtained by expressing the gradation of the red detection results on the division regions A1 to A4 by density of red. Further, images of the red detection results in the division regions A1 to A4 may be superimposed in an average color bar 60_3 in association with the division regions A1 to A4 dividing image data as shown in FIG. 59. With the arrangement, the observer can visually easily recognize density of red in a part in a region. FIG. 59 is a diagram showing an example of the average color bar 60_3 according to modification 6-3 of the sixth embodiment. The average color bar 60_3 is obtained by superimposing an image of the red detection result on the average color bar 60.

Seventh Embodiment

In the sixth embodiment (including its modifications), an image of a red detection result is linked and displayed on the average color bar 60. In the invention, an object which is linked and displayed on the average color bar is not limited to the red detection result. For example, a rotation amount used in the rotation correcting unit 154a can be also used. In the following, an example of this case will be described in detail with reference to the drawings as a seventh embodiment. In the following description, the seventh embodiment will be described using the first embodiment as a base. However, the invention is not limited to the case. Obviously, the seventh embodiment can be applied to any of the foregoing embodiments and their modifications.

Figure 60:
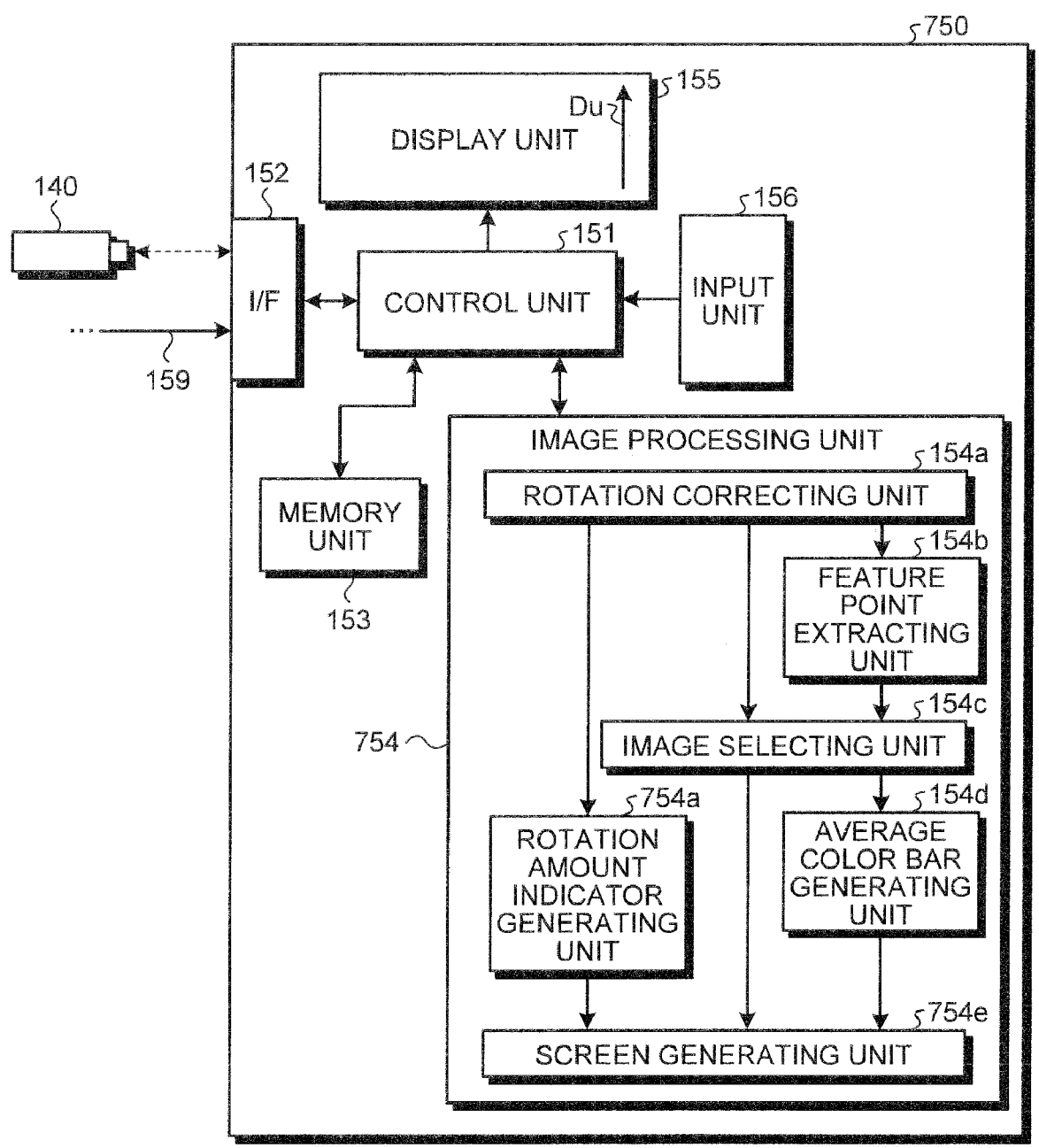
FIG. 60 is a block diagram showing an example of a schematic configuration of a display device according to a seventh embodiment.

The rotation amount is generated or specified on the basis of orientation data in the rotation correcting unit 154a of the image processing unit 154. Therefore, in the medical system according to the seventh embodiment, the display device 150 (refer to FIG. 7) in the medical system 1 shown in FIG. 1 is replaced with a display device 750 shown in FIG. 60. FIG. 60 is a block diagram showing a schematic configuration example of the display device 750 according to the seventh embodiment. As obvious from comparison between FIGS. 60 and 7, in the display device 750, the image processing unit 154 in the display device 150 is replaced with an image processing unit 754.

As shown in FIG. 60, the image processing unit 754 has a configuration similar to that of the image processing unit 154 except that a rotation amount indicator generating unit 754a is added and the screen generating unit 154e is replaced with a screen generating unit (screen generating means) 754e. The rotation correcting unit 154a according to the seventh embodiment supplies the generated or specified rotation amount to the rotation amount indicator generating unit 754a.

The rotation amount indicator generating unit 754a is rotation amount image generating means for generating an image (rotation amount image) visually displaying a rotation amount of each image data used at the time of rotation correction. In the embodiment, the rotation amount indicator (refer to a rotation amount indicator 68 in FIG. 62) is used as the rotation amount image. Therefore, the rotation amount indicator generating unit 754a generates an image of the rotation amount indicator using the input rotation amount and supplies the generated image to the screen generating unit 754e.

Figure 62:
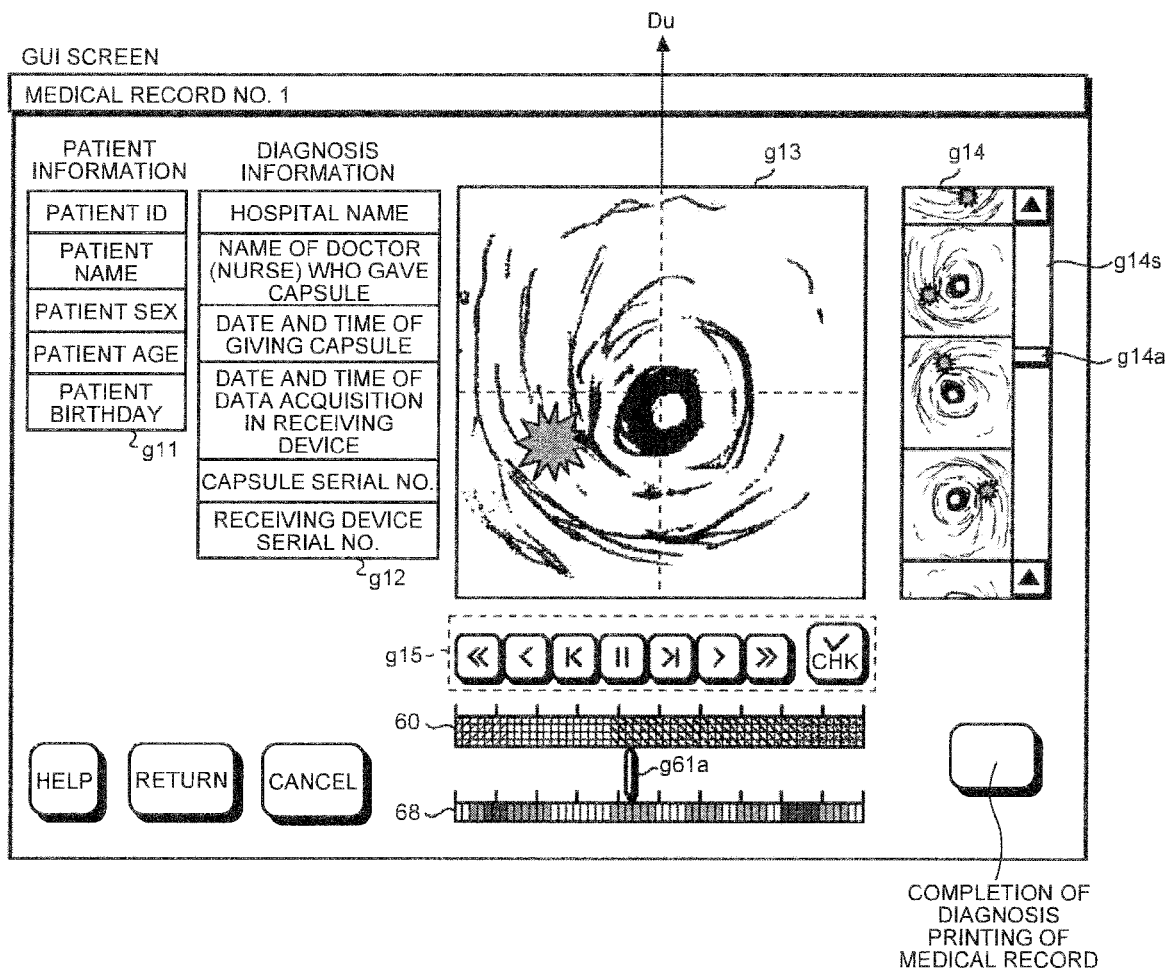
FIG. 62 is a diagram showing an example of a GUI screen generated by a screen generating unit according to the seventh embodiment.

The screen generating unit 754e generates a GUI screen as shown in FIG. 62 by using image data subjected to rotation correction which is selected by the image selecting unit 154c, an image of the average color bar supplied from the average color bar generating unit 154d, and an image of the rotation amount indicator input from the rotation amount indicator generating unit 754a. The GUI screen generated according to the seventh embodiment will be described later.

Figure 61:
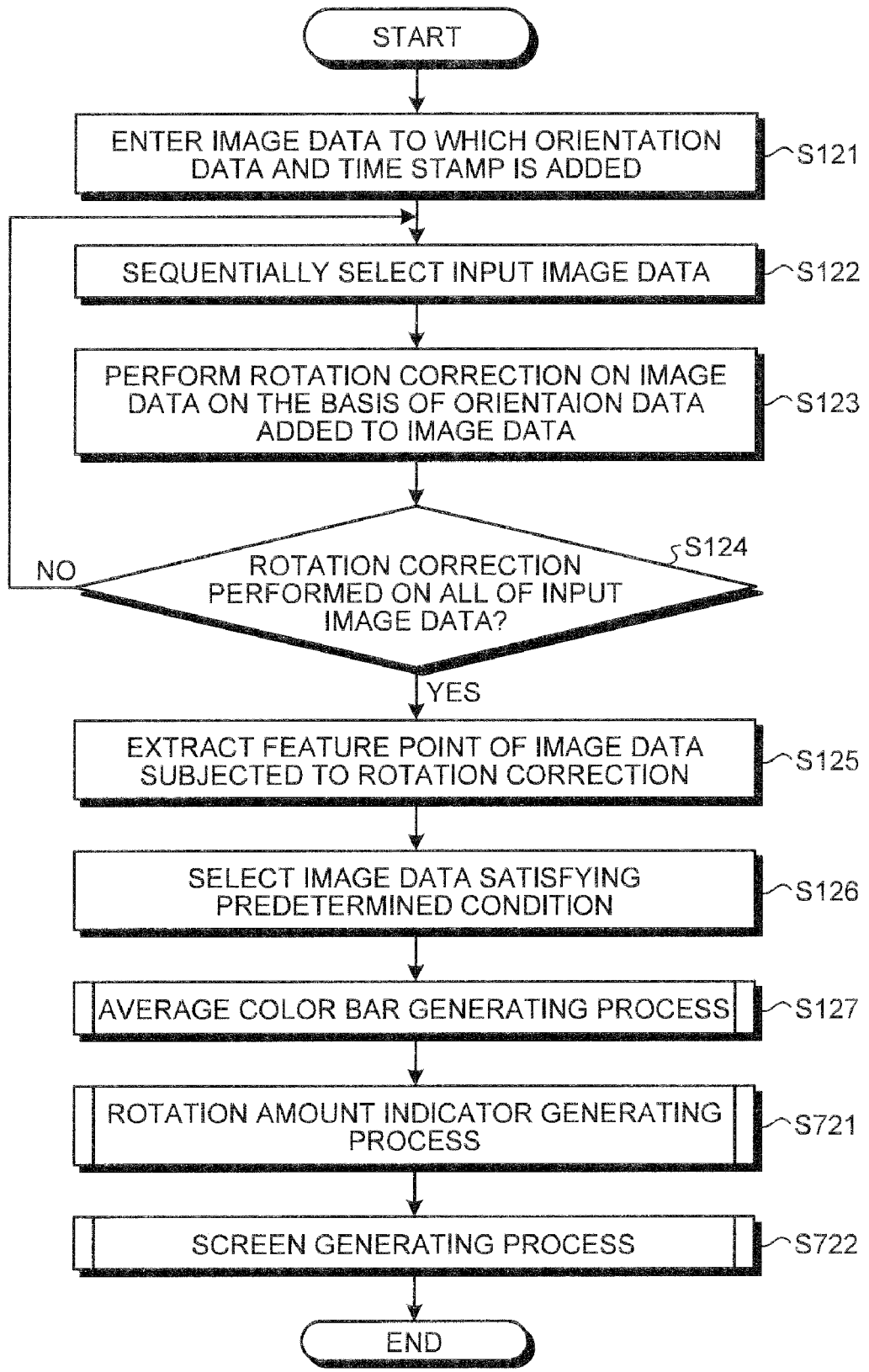
FIG. 61 is a flowchart showing an example of outline operation of the display device according to the seventh embodiment.

Using FIG. 61, the operation of the display device 750 according to the seventh embodiment will be described in detail. As shown in FIG. 61, first, the display device 750 takes steps similar to the steps described by using the steps S121 to S127 in FIG. 13 in the first embodiment, thereby executing the rotation correction on all of image data selected, and the process of generating an image of an average color bar. Next, the display device 750 executes a process of generating an image of a rotation amount indicator from the rotation amount in the rotation amount indicator generating unit 754a (step S721).

Next, the display device 750 makes the screen generating unit 754e execute the screen generating process for generating a GUI screen as shown in FIG. 62 by using the image data subjected to the rotation correction selected in the image selecting unit 154c, the image of the average color bar supplied from the average color bar generating unit 154d, and an image of the rotation amount indicator supplied from the rotation amount indicator generating unit 754a (step S722) and, after that, finishes the process. The generated GUI screen is supplied to the display unit 155 via the control unit 151 and displayed to the observer. As a result, the observer is provided with the GUI function using the GUI screen and the input unit 156.

Using FIG. 62, the GUI screen generated by the screen generating unit 754e will be described in detail. As shown in FIG. 62, in the GUI screen generated by the screen generating unit 754e, like the GUI screen (refer to FIG. 8) generated by the screen generating unit 154e in the foregoing embodiments, the patient information g11, the diagnosis information g12, the main image display region g13, the sub image display region g14, the reproduction control button g15, and the average color bar 60 are incorporated. In the GUI screen, the rotation amount indicator 68 is also incorporated.

The length in the time base direction of the rotation amount indicator 68 is the same as that of the average color bar 60, and the rotation amount indicator 68 is disposed above or below the average color bar 60 in the screen. With the arrangement, the time base of the average color bar 60 and that of the rotation amount indicator 68 can be linked in appearance, so that it enables the observer to easily recognize a region in the capsule medical device 10 largely rotates, in the average color bar 60.

The color in a region corresponding to each of image data pieces in the rotation amount indicator 68 is graded according to the rotation amount. Consequently, the observer can easily recognize a region in which the capsule medical device 10 largely rotates.

Modification 7-1

Figure 63:
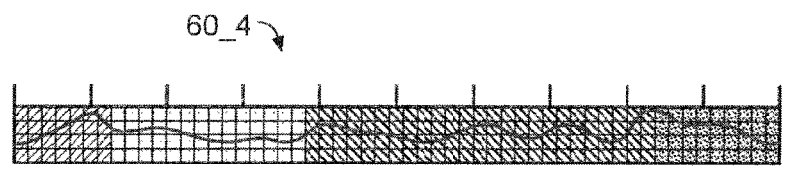
FIG. 63 is a diagram showing an example of an average color bar according to modification 7-1 of the seventh embodiment.

In the seventh embodiment, the case of visually displaying the rotation amount by using the rotation amount indicator 68 (refer to FIG. 62) expressing the rotation amount by a bar-shaped image has been described as an example. The present invention is not limited to the case but, for example, as shown in FIG. 63, the rotation amount may be superimposed on the average color bar. FIG. 63 is a diagram showing an example of an average color bar 604 according to the modification 7-1 of the seventh embodiment. The average color bar 60_4 is obtained by superimposing an image expressing a rotation amount by a polygonal line in the average color bar 60. Therefore, in the image of the rotation amount, as shown in FIG. 63, the rotation amount in each image data is expressed by the height of the polygonal line. The invention, however, is not limited to the expression. The rotation amount may be expressed by a histogram or the like.

The rotation amount may be averaged by rotation amounts in a predetermined number of successive image data pieces. In the case where the averaging is not performed, the observer can know sharpness of a change in the rotation amount from an image of the polygonal line of the rotation amount. In the case of performing the averaging, the observer can easily know the trend of a change in the rotation amount from the image of the polygonal line of the rotation amount.

Eighth Embodiment

Next, an eighth embodiment will be described in detail with reference to the drawings. In the following description, the eighth embodiment will be described using the first embodiment as a base. However, the invention is not limited to the description. Obviously, the eighth embodiment can be applied to any of the foregoing embodiments and their modifications.

Figure 64:
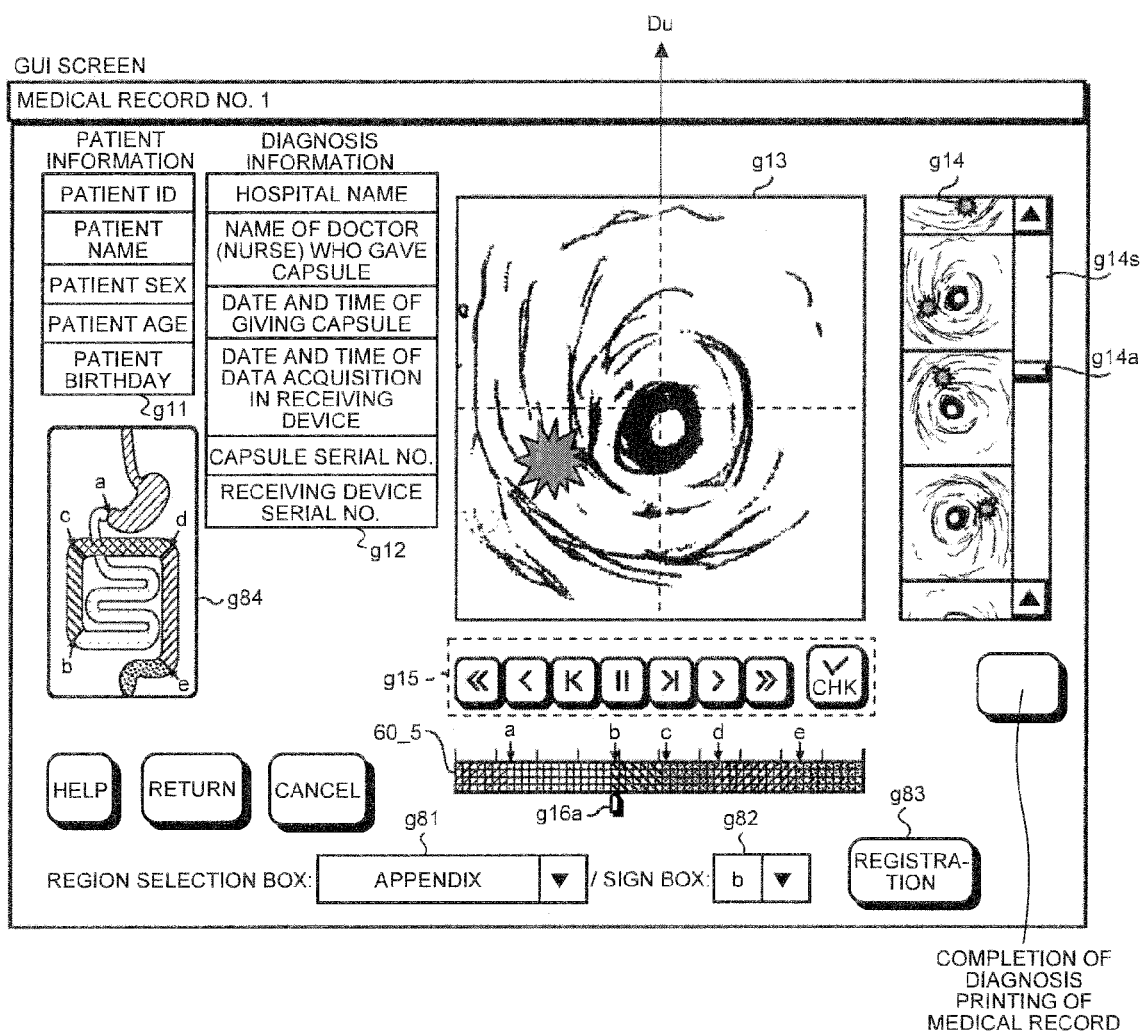
FIG. 64 is a diagram showing an example of a GUI screen according to an eighth embodiment.

The color and shape of the lumen in the subject 900 varies according to a region. The observer can recognize a region which is presently displayed in the main image display region g13 in the GUI screen by visually recognizing the average color bar 60 as shown in the foregoing embodiments (including their modifications). In the eighth embodiment, the GUI function enabling the observer can add an index of an arbitrary region to the average color bar 60 is provided for the observer by using a GUI screen (refer to FIG. 64) displayed in the display unit 155 and the input unit 156. FIG. 64 is a diagram showing an example of the GUI screen according to the eighth embodiment.

As shown in FIG. 64, in the GUI screen according to the eighth embodiment, like the GUI screen (refer to FIG. 8) according to the first embodiment, the patient information g11, the diagnosis information g12, the main image display region g13, the sub image display region g14, and the reproduction control button g15 are incorporated. In the embodiment, the average color bar 60 in FIG. 8 is replaced with the average color bar 60_5. In the GUI screen according to the eighth embodiment, a box (region selection box g81) for selecting an index added to the position of the slider g16a in the average color bar 60_5, a box (sign box g82) for selecting a sign displaying the selected index, and a registration button g83 for entering registration of the selected index and the sign are incorporated.

The observer selects, as an index, a target region from a pulldown menu provided in the region selection box g81. When any region is selected in the region selection box g81, in the sign box g82, the sign to be selected next is automatically selected in accordance with a predetermined order. The observer can change a sign to be selected by the pulldown menu provided in the sign box g82. The region selection box g81 may be constructed to directly enter a character string. Further, a sign may be designated in advance to an index selected in the region selection box g81.

After selecting the name of the region and the sign in such a manner, the observer clicks the registration button g83. The display device 750 enters the selected region and the sign as an index to the screen generating unit 754e in the image processing unit 754. The screen generating unit 754e adds the index to the average color bar 60_5 by using the input name of the region and the sign, generates an image for visually displaying the index (particularly, the sign), and adds the image to a corresponding part in the average color bar 60_5. The GUI screen in which the image of the index is added to the average color bar 60_5 is supplied to the display unit 155 and displayed to the observer. As a result, in the corresponding part in the average color bar 60_5, as shown in FIG. 64, the sign (for example, "a" to "e") indicating that the index is added is displayed. Consequently, the observer can easily know the region whose image data is presently displayed in the main image display region g13.

In the GUI screen according to the eighth embodiment, an image of the lumen in the subject 900 (hereinbelow, called organ image) g84 is incorporated. In the case where the subject 900 is a human, regions such as pylorus, appendix, hepatic flexure, splenic flexure, colon sigmoid, and the like do not depend on individuals but are almost the same in all of the subjects 900.

In the eighth embodiment, the organ image g84 is formed as an image of the general subject 900, and the position of the region in an image drawn by the organ image g84 is defined in advance. When the observer selects a region by using the region selection box g81 in the GUI screen shown in FIG. 64, an image (color, texture, or the like) of a region sandwiched by the region selected in the average color bar 60_5 and the region selected before is adhered to a corresponding interval in the lumen shape in the organ image g84. In the case where there is no image selected before, images (colors, textures, or the like) from the head to a corresponding region in the time base of the average color bar 60_5 are adhered to the organ image g84.

By the operation as described above, display similar to the average color bar 60_5 can be superimposed on the organ image g84 in the GUI screen according to the embodiment. As a result, the observer can easily recognize an average color in a region.

In the eighth embodiment, an index to be added to the average color bar 60_5 is selected/entered manually. However, the invention is not limited to the case. For example, a region may be automatically specified from the color or the like of the average color bar 60_5 and added as an index to the average color bar 60_5.

Modification 8-1

Figure 65:
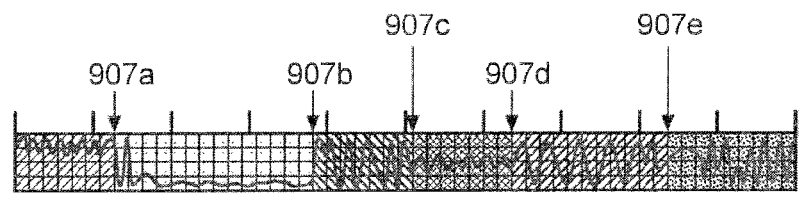
FIG. 65 is a diagram showing the relation between a region in a lumen through which a capsule medical device introduced in a subject passes and rotation amount.

The rotation amount and a change rate of the rotation amount of a capsule medical device introduced in the subject 900 change according to the shape of a lumen through which the device passes, that is, the region as shown in FIG. 65. FIG. 65 is a diagram showing the relation between the region in the lumen 902 through which the capsule medical device 10 introduced in the subject 900 passes and the rotation amount.

The region can be automatically specified on the basis of changes in the rotation amount and the change rate and added as an index to the average color bar 60_5. In the following, the case will be described in detail as modification 8-1 of the eighth embodiment with reference to the drawings. In the following description, the modification 8-1 will be described using the eighth embodiment as a base. However, the invention is not limited to the case. Obviously, the modification 8-1 can be applied, to any of the foregoing embodiments and their modifications.

Figure 66:
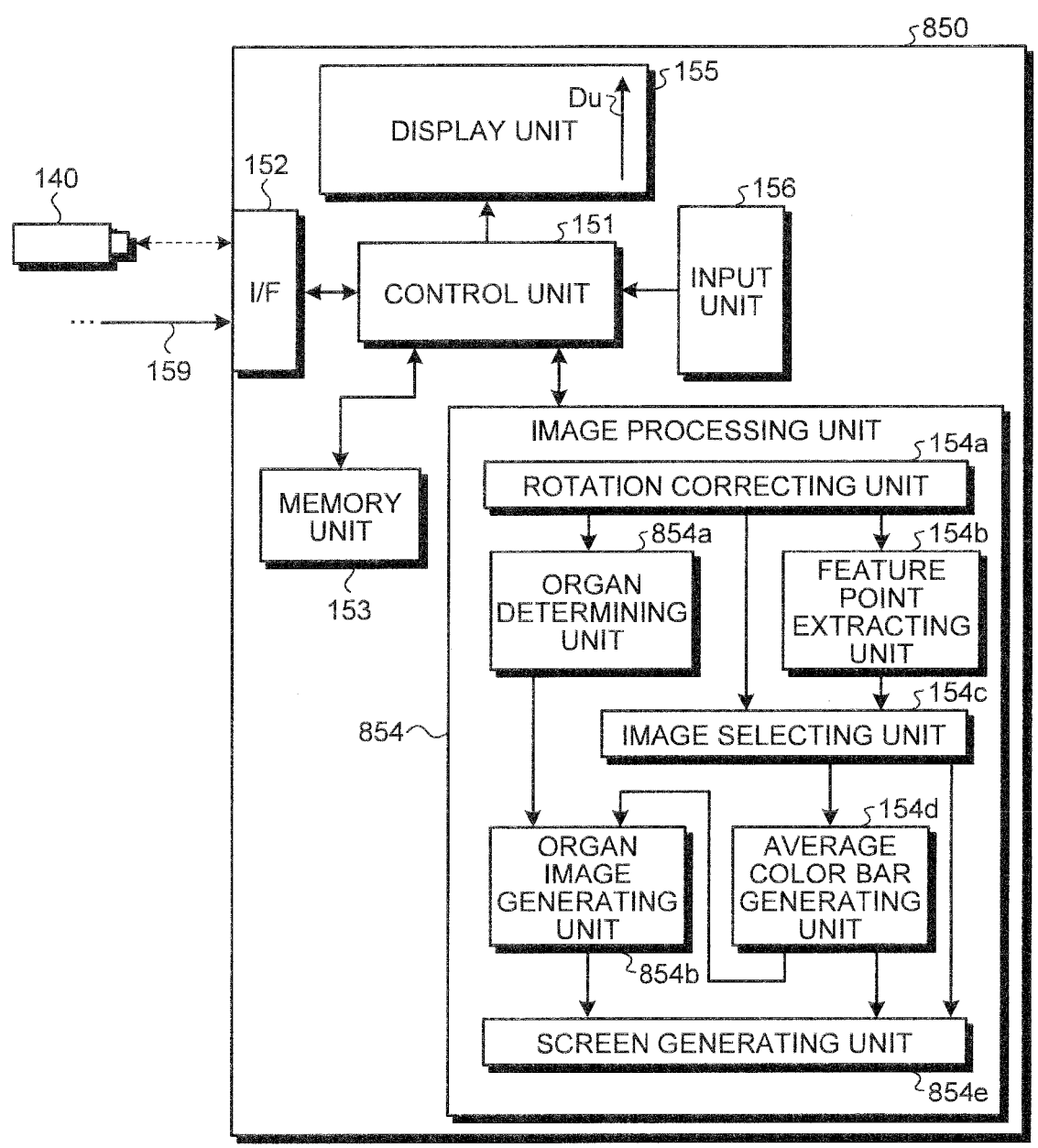
FIG. 66 is a block diagram showing an example of a schematic configuration of a display device according to modification 8-1 of an eighth embodiment.

In a medical system according to the modification 8-1, the display device 150 (refer to FIG. 7) in the medical system 1 shown in FIG. 1 cited in the eighth embodiment is replaced with a display device 850 shown in FIG. 66. FIG. 66 is a block diagram showing a schematic configuration example of the display device 850 according to the modification 8-1. As obvious from comparison between FIG. 66 and FIG. 7, in the display device 850, the image processing unit 154 in the display device 150 is replaced with an image processing unit 854.

As shown in FIG. 66, the image processing unit 854 has a configuration similar to that of the image processing unit 154 except that an organ determining unit (organ determining means) 854a and an organ image generating unit (organ image generating unit) 854b are added and the screen generating unit 154e is replaced with a screen generating unit (screen generating means) 854e. The rotation correcting unit 154a according to the modification 8-1 enters the generated or specified rotation amount to the organ determining unit 854a. The average color bar generating unit 154d enters the data of the average color in the regions generated to the organ image generating unit 854b.

The organ determining unit 854a functions as organ determining means for determining an organ positioned near the capsule medical device 10 when image data is obtained on the basis of the rotation amount of each image data used for rotation correction, and specifies image data at a timing when the capsule medical device 10 passes through each of the organs (for example, pylorus 907a, appendix 907b, hepatic flexure 907c, splenic flexure 907d, colon sigmoid 907e, and the like) from the input rotation amount and the change rate. The rotation amount is generated for each image data which is associated with each other.

The organ determining unit 854a specifies an image of an average color bar corresponding to a path between the organs from the image data (its ID) of each organ specified and an image of the average color bar entered from the average color bar generating unit 154d, and supplies the specified result to the organ image generating unit 854b. The image of the average color bar is obtained by connecting images of the average colors of image data pieces. With the image of the average color of image data, the ID of the corresponding image data is associated.

The organ image generating unit 854b matches the organ image preliminarily generated and the index added to the organ image with a specification result entered from the organ determining unit 854a, specifies data of the average color in the corresponding regions to the organ image of the regions matched, and adheres it to the organ image. In such a manner, an organ image similar to the organ image g84 in the GUI screen illustrated in FIG. 64 is automatically generated.

Modification 8-2

Figure 67:
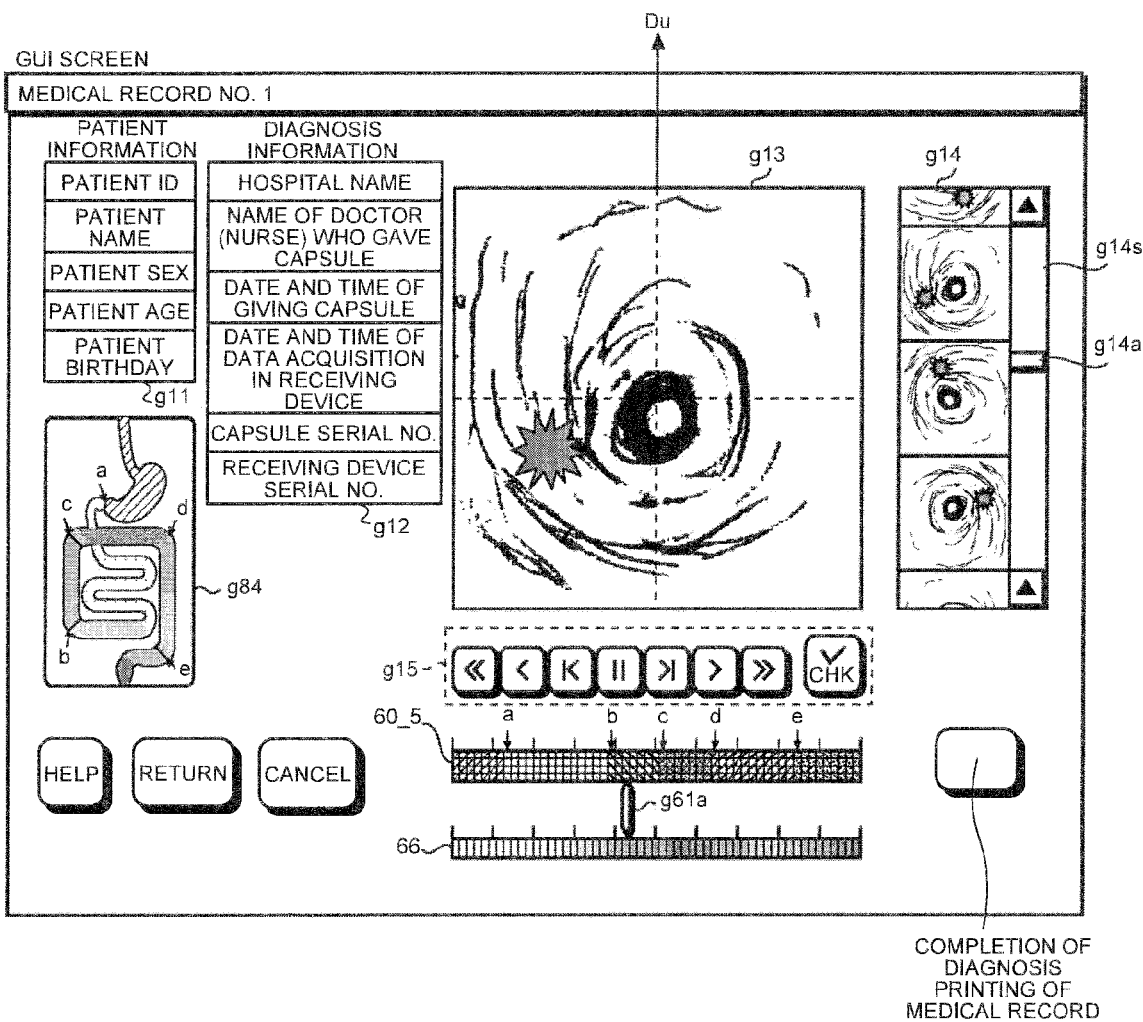
FIG. 67 is a diagram showing an example of a GUI screen according to modification 8-2 of the eighth embodiment.

On the organ image g84, not only an image of the average color but a red detection result may be also superimposed as shown in an organ image g84B incorporated in a GUI screen according to modification 8-2 of the eighth embodiment shown in FIG. 67.

Since an image processing unit which generates the organ image g84B can be easily reached from the image processing unit 654 shown in FIG. 54 and the image processing unit 854 shown in FIG. 66, its detailed description will not be given here. In the GUI screen shown in FIG. 67, the red indicator 66 is also incorporated.

Modification 8-3

Figure 68:
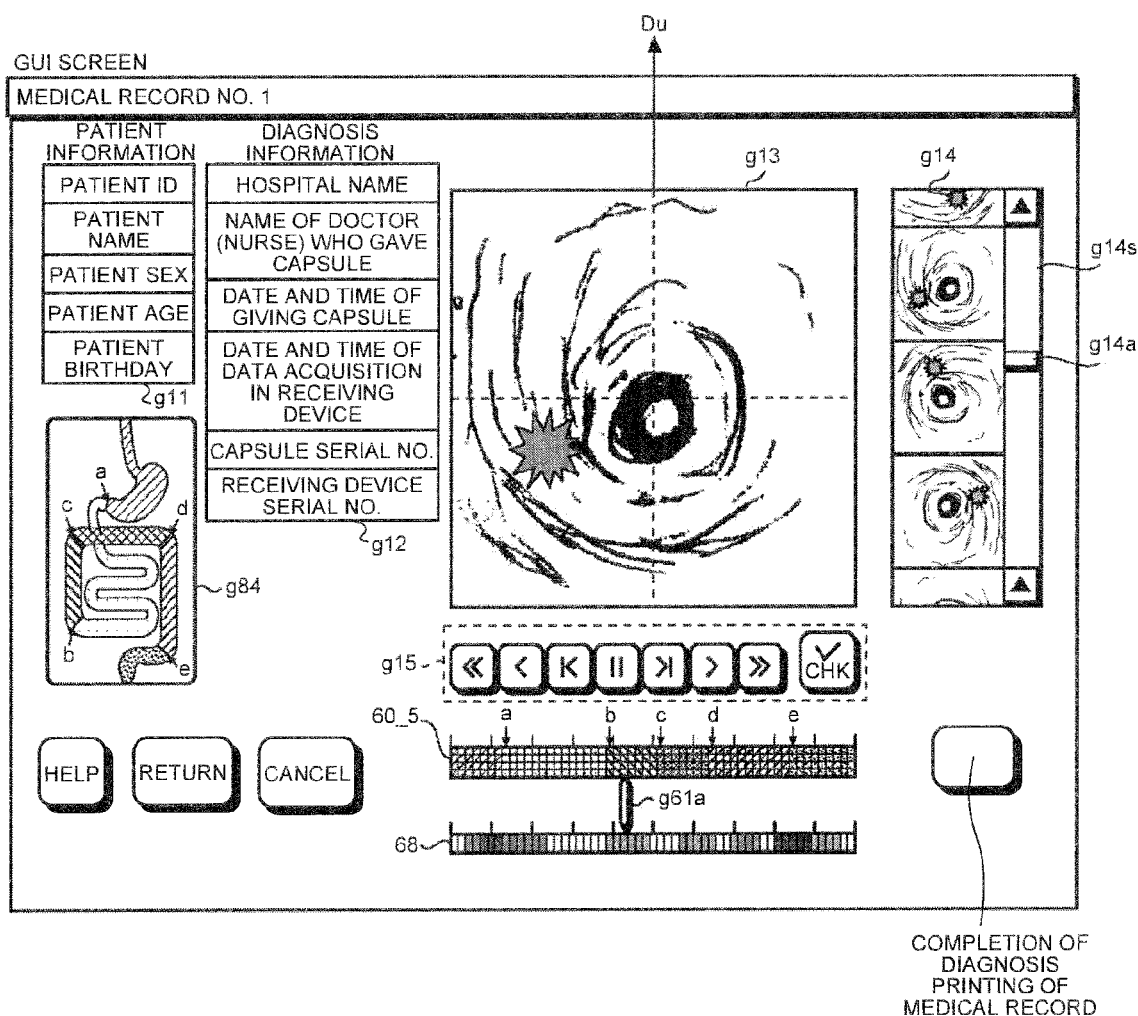
FIG. 68 is a diagram showing an example of a GUI screen according to modification 8-3 of the eighth embodiment.

Further, in the GUI screen (refer to FIG. 64) according to the embodiment, as shown in a GUI screen according to modification 8-3 shown in FIG. 68, for example, the rotation amount indicator 68 may be incorporated.

Ninth Embodiment

Figure 69:
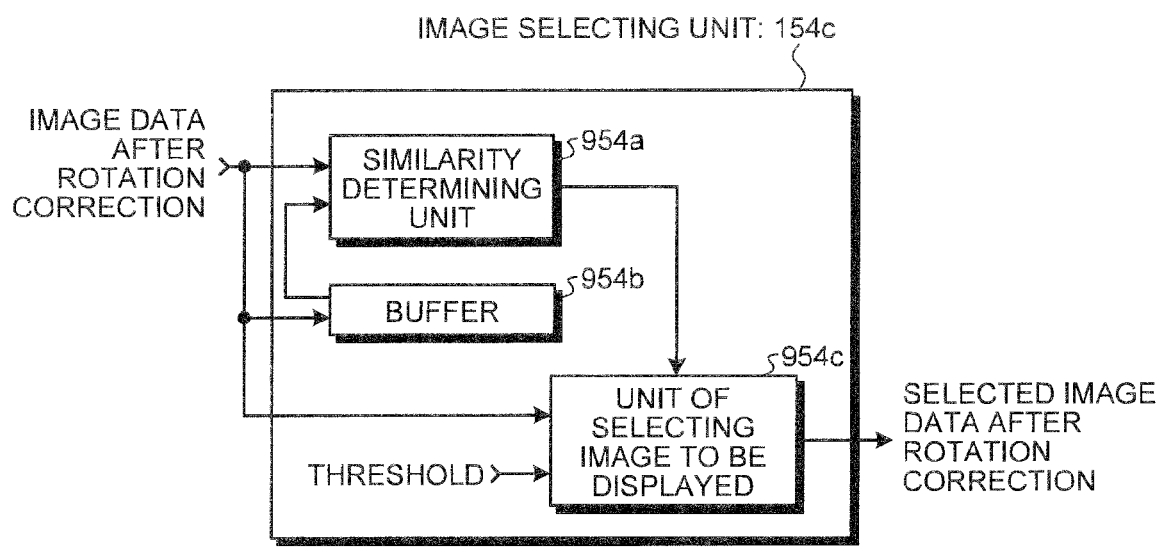
FIG. 69 is a block diagram showing an example of a schematic configuration of an image selecting unit according to a ninth embodiment.

More concrete description of the image selecting unit 154c in the foregoing embodiments (including their modifications) will be given below as a ninth embodiment with reference to drawings. FIG. 69 is a block diagram showing a schematic configuration example of the image selecting unit 154c according to the ninth embodiment.

As shown in FIG. 69, the image selecting unit 154c includes a buffer 954b for temporarily holding an image subjected to rotation correction which is entered last time, a similarity determining unit 954a for determining similarity of image data of this time to immediately preceding image data from an image subjected to rotation correction which is entered this time and an image subjected to rotation correction of last time which is held in the buffer 954b, and a unit 954c for selecting an image to be displayed, which selects image data subjected to rotation correction on the basis of the determination of the similarity by the similarity determining unit 954a.

The similarity determining unit 954a functions as similarity determining means for determining similarity between successive image data in a plurality of pieces of image data subjected to rotation correction. The similarity determining unit 954a obtains the difference between color component values pixel by pixel in the same position in image data subjected to rotation correction of last time read from the buffer 954b and image data subjected to rotation correction of this time, and obtains the sum of the differences of the color component values derived pixel by pixel in the entire screen. In the case where the sum of the differences of the color component values in the entire screen is smaller than a predetermined threshold, it is determined that the image data subjected to rotation correction of this time is image data similar to the image data subjected to rotation correction of last time, that is, image data of the same region. The determination result is supplied to the unit 954c of selecting an image to be displayed. On the other hand, in the case where the sum of the differences of the color component values in the entire screen of the image data subjected to rotation correction of last time and image data subjected to rotation correction of this time is equal to or larger than the predetermined threshold, it is determined that the image data subjected to rotation correction of this time is image data different from the image data subjected to rotation correction of last time, that is, image data of a different region. The determination result is supplied to the unit 954c of selecting an image to be displayed.

The unit 954c of selecting an image to be displayed functions as image data selecting means for selecting image data subjected to rotation correction and satisfying a predetermined condition from a plurality of pieces of image data subjected to rotation correction on the basis of the determination result of the similarity determining unit 954a. In the case where the determination result supplied from the similarity determining unit 954a indicates that image data subjected to rotation correction of this time is image data of a region different from that of image data subjected to rotation correction of last time, the unit 954c of selecting an image to be displayed selects the image data. That is, the image data is supplied to the average color bar generating unit 154d and the screen generating unit 154e. On the other hand, in the case where the determination result supplied from the similarity determining unit 954a indicates that image data subjected to rotation correction of this time is image data of the same region as that the image data subjected to rotation correction of last time, the unit 954c of selecting an image to be displayed discards the image data subjected to rotation correction of this time.

By constructing the image selecting unit 154c as described above, in the ninth embodiment, image data subjected to rotation correction of a region different from that of the image data subjected to rotation correction of last time can be preferentially selected and displayed. As a result, a number of image data pieces of the same region can be prevented from being continuously displayed, so that the observer can read the images more efficiently.

In the embodiment, by adjusting a threshold used at the time of determining similarity of successive images, the number of pieces of image data to be selected can be adjusted. As a result, the reproduction speed can be also adjusted.

Tenth Embodiment

Figure 70:
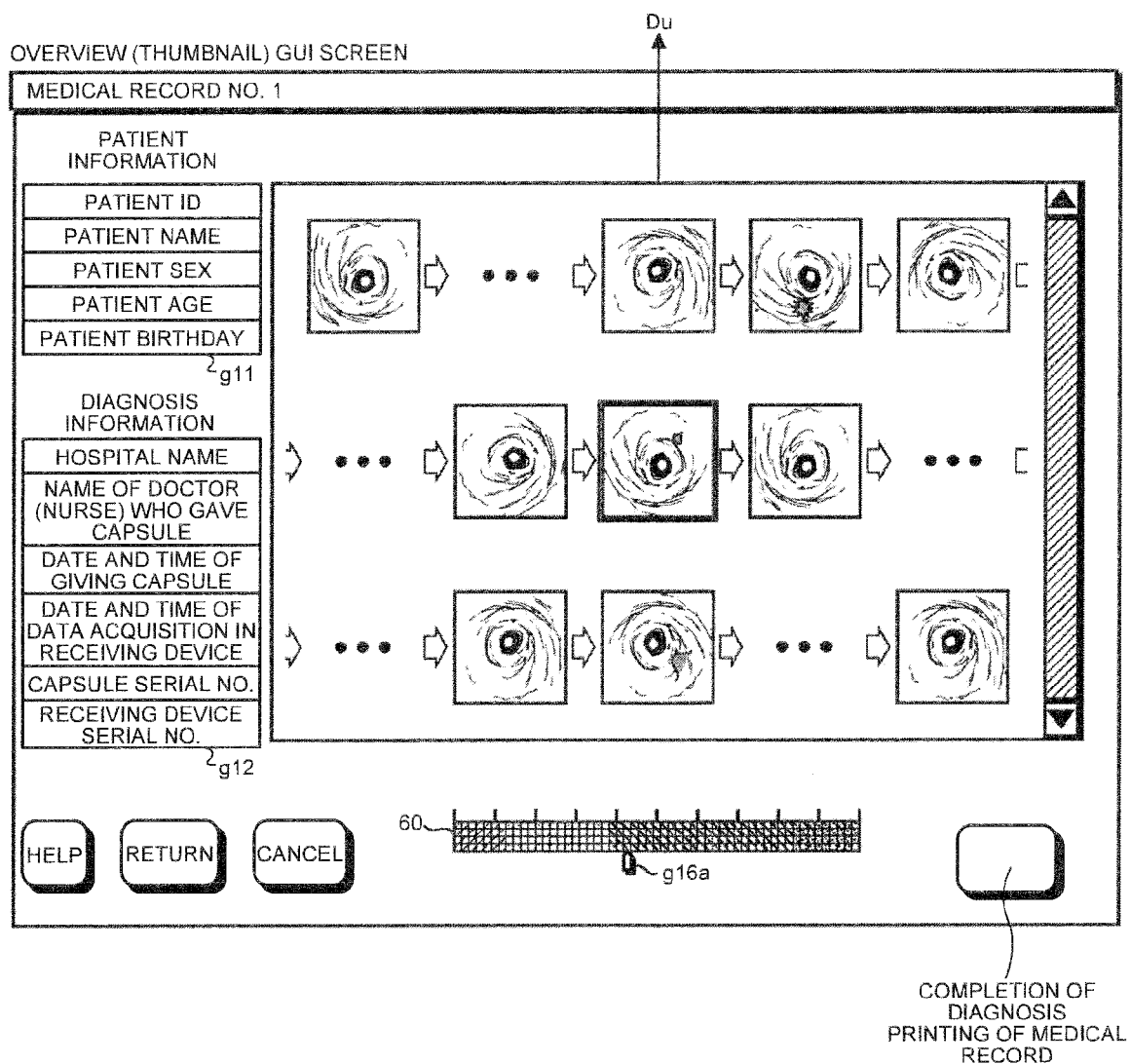
FIG. 70 is a diagram showing an example of a GUI screen according to a tenth embodiment.

The screen generating unit (154e, 654e, 754e, or 854e) in any of the foregoing embodiments (including their modifications) may form thumbnail images of image data subjected to rotation correction which is selected by the image selecting unit 154c and display a list of the images as shown in a GUI screen according to a tenth embodiment of FIG. 70 (also called "overview display"). That is, the screen generating unit 154e in the display device 150 may reduce the selected image data subjected to rotation correction and generate a GUI screen (refer to FIG. 70) displaying a list of reduced images.

Eleventh Embodiment

Figure 71:
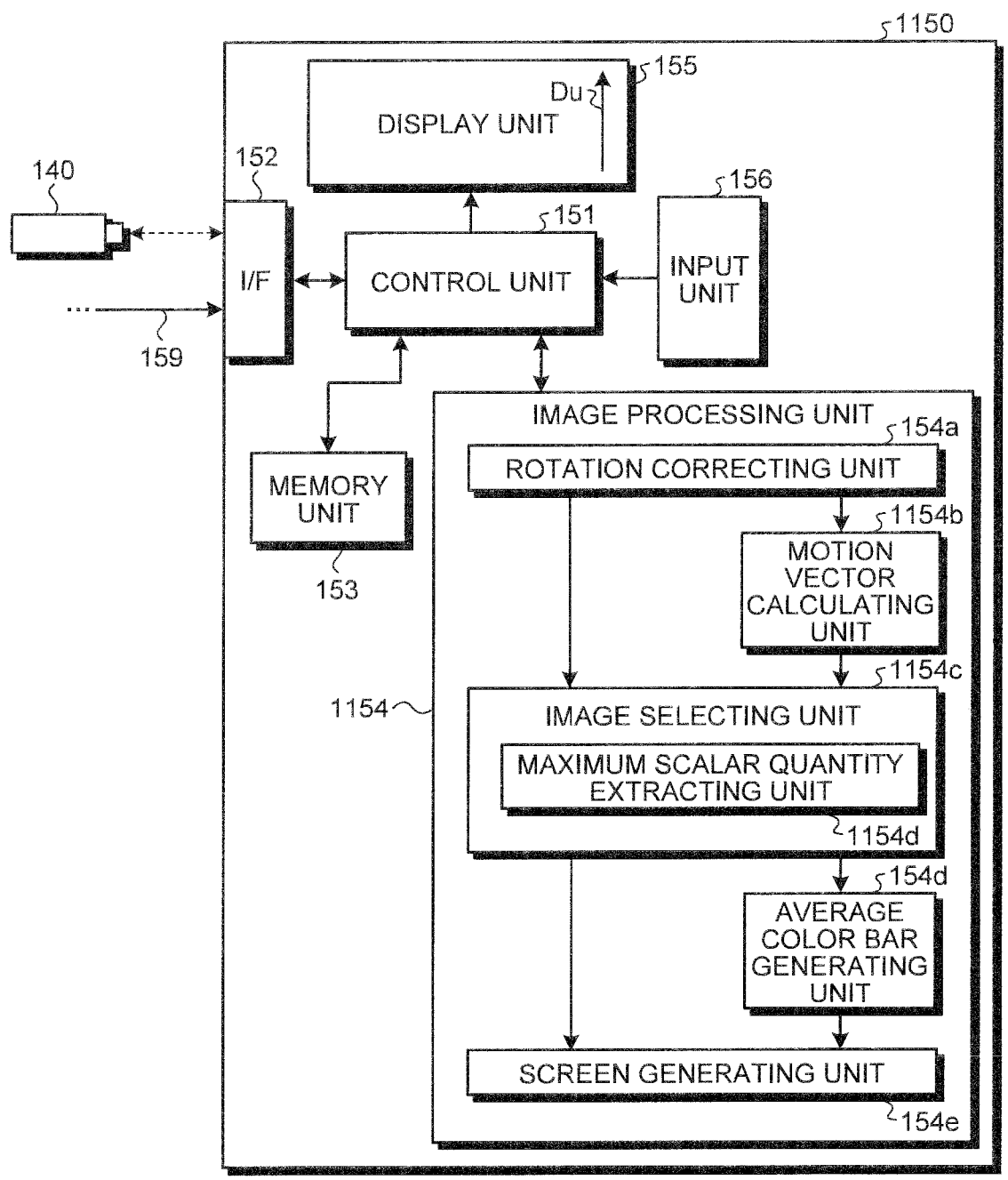
FIG. 71 is a block diagram showing an example of a schematic configuration of a display device according to an eleventh embodiment.

Another form of the display device 150 in any of the foregoing embodiments (including their modifications) will be described in detail below as an eleventh embodiment with reference to the drawings. FIG. 71 is a block diagram showing a schematic configuration example of a display device 1150 according to the eleventh embodiment. In the following description, the eleventh embodiment will be described using the first embodiment as a base. However, the invention is not limited to the case. Obviously, the eleventh embodiment can be applied to any of the foregoing embodiments and their modifications.

As shown in FIG. 71, the display device 1150 has a configuration similar to that of the display device 150 shown in FIG. 7 except that the image processing unit 154 is replaced with an image processing unit 1154.

As shown in FIG. 71, the image processing unit 1154 has a configuration similar to that of the image processing unit 154 except that the feature point extracting unit 154b is replaced with a motion vector calculating unit 1154b, and the image selecting unit 154c is replaced with an image selecting unit 1154c.

The motion vector calculating unit 1154b functions as motion vector calculating means for calculating a motion vector between successive image data in a plurality of pieces of image data subjected to rotation correction, calculates a motion vector in a region in the successive image data, and supplies the motion vector to the image selecting unit 1154c. The image selecting unit 1154c includes a maximum scalar quantity extracting unit 1154d (maximum scalar quantity extracting means) for extracting a value at which a scalar quantity is maximum in the motion vectors supplied from the motion vector calculating unit 1154b. The image selecting unit 1154c functions as image data selecting means for selecting image data subjected to the rotation correction and satisfying a predetermined condition, from a plurality of pieces of image data subjected to the rotation correction on the basis of a result of extraction by the maximum scalar quantity extracting unit 1154d.

For example, in the case where the maximum scalar quantity of the motion vector extracted by the maximum scalar quantity extracting unit 1154d is equal to or less than a predetermined threshold, the image selecting unit 1154c determines that image data of last time and image data of this time are captured from different regions and selects the image data of this time. That is, the image data is supplied to the average color bar generating unit 154d and the screen generating unit 154e. On the other hand, in the case where the maximum scalar amount of the motion vector extracted by the maximum scalar quantity extracting unit 1154d is larger than a predetermined threshold, the image selecting unit 1154c determines that image data of last time and image data of this time are captured from the same region and discards the image data of this time.

By constructing the image selecting unit 1154c as described above, in the eleventh embodiment, the image data subjected to rotation correction of a region different from that of the image data subjected to rotation correction of last time can be preferentially selected and displayed. As a result, a number of image data pieces of the same region can be prevented from being continuously displayed, so that the observer can read the images more efficiently.

In the embodiment, by adjusting a threshold used at the time of determining similarity of successive images, the number of pieces of image data to be selected can be adjusted. As a result, the reproduction speed can be also adjusted.

Twelfth Embodiment

Figure 72:
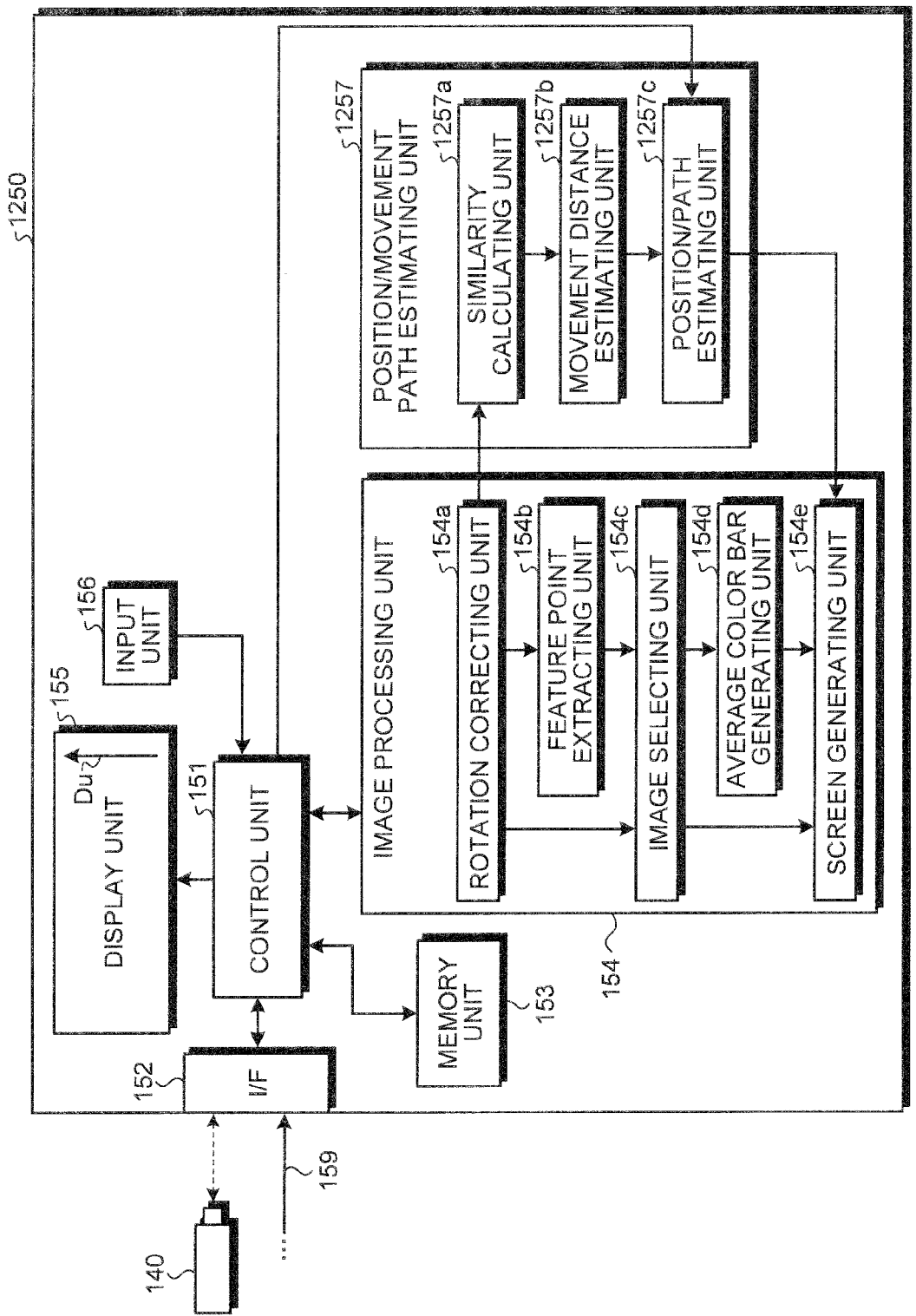
FIG. 72 is a block diagram showing an example of a schematic configuration of a display device according to a twelfth embodiment.

Another form of the display device 150 or 1150 in any of the foregoing embodiments (including their modifications) will be described in detail below as a twelfth embodiment with reference to the drawings. FIG. 72 is a block diagram showing a schematic configuration example of a display device 1250 according to the twelfth embodiment. In the following description, the twelfth embodiment will be described using the first and eighth embodiments as a base. However, the invention is not limited to the case. Obviously, the twelfth embodiment can be applied to any of the foregoing embodiments and their modifications.

As shown in FIG. 72, the display device 1250 has, in addition to a configuration similar to that of the display device 150 shown in FIG. 7, a position/movement path estimating unit 1257. In the twelfth embodiment, the image data subjected to rotation correction by the rotation correcting unit 154*a* in the image processing unit 154 is also supplied to the position/movement path estimating unit 1257.

The position/movement path estimating unit 1257 functions as position estimating means for estimating the position of the capsule medical device 10 at the time of obtaining image data on the basis of the rotation amount used for rotation correction on each image data, and includes a similarity calculating unit 1257*a* for calculating similarity of image data successively supplied from the rotation correcting unit 154*a*, a movement distance estimating unit 1257*b* for estimating a distance of movement of the capsule medical device 10 during imaging the successive image data on the basis of the similarity calculated by the similarity calculating unit 1257*a*, and a position/path estimating unit 1257*c* for estimating the position and a movement path of the capsule medical device 10 at the time of capturing image data of this time on the basis of the movement distance estimated by the movement distance estimating unit 1257*b*.

The image data subjected to rotation correction which is supplied from the rotation correcting unit 154*a* to the position/movement path estimating unit 1257 is supplied to the similarity calculating unit 1257*a*. The similarity calculating unit 1257*a* calculates similarity of successive image data in the input image data subjected to rotation correction and supplies the calculated similarity to the movement distance estimating unit 1257*b*. The similarity of successive image data can be calculated from, for example, a feature point, a motion vector, or the like of the image data.

The movement distance estimating unit 1257*b* estimates a distance of movement of the capsule medical device 10 at the time of capturing the successive image data on the basis of the input similarity and supplies the estimated movement distance to a position/path estimating unit 1257*c*. The movement distance can be estimated on the basis of, for example, a corresponding relation between similarity and distance which is obtained in advance by experiment, experience, simulation, or the like.

The position/path estimating unit 1257*c* estimates the position and movement path of the capsule medical device 10 at the time of capturing the image data of this time on the basis of the input movement distance and the position and the movement path of the capsule medical device 10 at the time of capturing image data of last time estimated last time, and supplies them to the screen generating unit 154*e* in the image processing unit 154. To the position/path estimating unit 1257*c*, information on the position and the movement path of the capsule medical device 10 may be separately supplied from the control unit 151 or the like. In the case where the information on the position and the movement path of the capsule medical device 10 is supplied separately, the position/path estimating unit 1257*c* corrects an error in the position and the movement path of the capsule medical device 10 estimated as described above, with the position and the movement path supplied separately. The error correction can be executed by, for example, a convergence calculation by iterative operation using the least square method.

Figure 73:
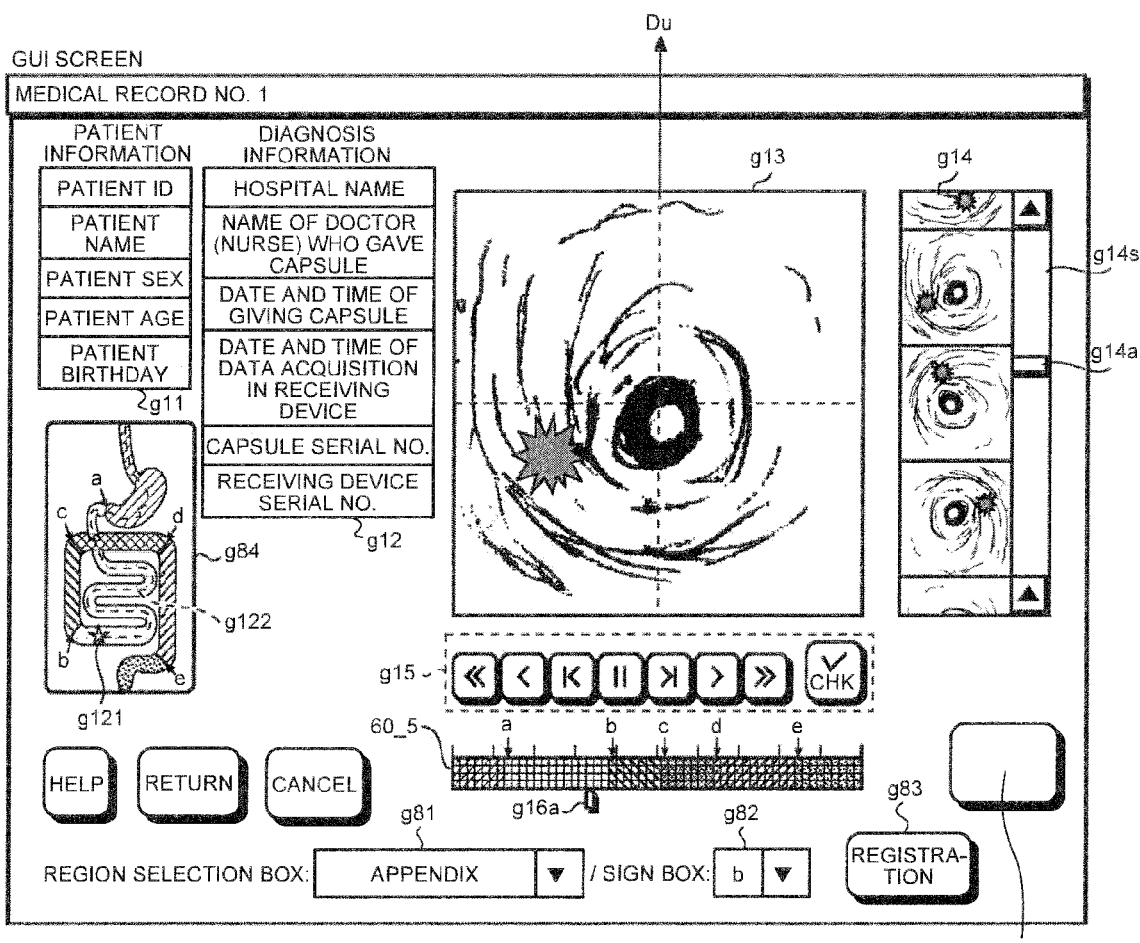
FIG. 73 is a diagram showing an example of a GUI screen according to the twelfth embodiment.

The position and the movement path at each of the imaging timings of the capsule medical device 10 estimated by the position/movement path estimating unit 1257 are supplied to, for example, the screen generating unit 154*e* in the image processing unit 154. The screen generating unit 154*e* generates, for example, a GUI screen as shown in FIG. 73 by using the position and the movement path of the capsule medical device 10 at each of the imaging timings. The GUI screen shown in FIG. 73 is obtained by, for example, applying the embodiment to the GUI screen according to the eighth embodiment.

As shown in the GUI screen of FIG. 73, in the twelfth embodiment, a marker g121 indicative of the position of the capsule medical device 10 at the timing of capturing the image data being displayed in the main image display region g13 and a path g122 of movement of the capsule medical device 10 until the image data is captured are superimposed on the organ image g84. With the image, the observer can easily know the position of the capsule medical device 10 and the movement locus until then at the time of capturing the image data being displayed from the organ image g84.

According to the embodiments, the orientations of a plurality of image data pieces can be aligned by performing rotation correction on image data on the basis of the orientation with reference to the reference direction of the body-insertable apparatus at the time of imaging, so that the image processing system, the external device of the same, and the image processing method realizing reduced time and labor at the time of diagnosis and improved accuracy of a diagnosis result can be realized.

The foregoing embodiments are just examples for carrying out the present invention. The invention is not limited to the embodiments. Obviously, various modifications according to specifications and the like are in the scope of the present invention. It is obvious from the above description that other various embodiments are possible within the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing system comprising:
a body-insertable apparatus including an imaging unit that captures inside of a subject and an output unit that outputs image data obtained by the imaging unit to the outside; and
an external device including
an input unit that receives the image data,
a first orientation specifying unit that specifies orientation of the body-insertable apparatus at the time of capturing the image data with respect to a reference direction,
a rotation correcting unit that performs rotation correction on image data which is received by the input unit based on the orientation specified by the first orientation specifying unit, thereby aligning orientations of a plurality of pieces of image data,
a screen generating unit that generates a screen displaying the image data subjected to the rotation correction in the rotation correcting unit,
an average color bar generating unit that calculates an average color of the image data subjected to the rotation correction in the rotation correcting unit, generates an image of the calculated average color, and generates an average color bar in which images of the generated average colors are connected in accordance with order of the image data, and an organ image generating unit that generates an organ image, as an image of an organ in the subject, obtained by superimposing the images of the average colors generated by the average color bar generating unit, wherein the screen generating unit generates the screen in which the average color bar generated by the average color bar generating unit is incorporated, and incorporates the organ image generated by the organ image generating unit into the screen.

2. The image processing system according to claim 1, wherein the first orientation specifying unit specifies orientation of the body-insertable apparatus using orientation of the subject as a reference.

3. The image processing system according to claim 1, wherein the first orientation specifying unit obtains orientation of the body-insertable apparatus using a real space as a reference.

4. The image processing system according to claim 1, wherein the external device further includes a directional antenna having directivity and an electromagnetic wave transmitting unit that transmits an electromagnetic wave via the directional antenna, the body-insertable apparatus further includes a plurality of antennas and a strength/phase detecting unit that detects strength and phase of the electromagnetic wave received by each antenna, the output unit adds the strength and phase of the electromagnetic wave detected by the strength/phase detecting unit to the image data and outputs the resultant data to the outside, the input unit supplies the strength and phase of the electromagnetic wave added to the image data to the first orientation specifying unit, and the first orientation specifying unit specifies the orientation of the body-insertable apparatus from the strength and phase of the electromagnetic wave supplied from the input unit.

5. The image processing system according to claim 4, wherein the external device further includes a second orientation specifying unit that specifies orientation of the subject, the reference direction is set for the subject, and the first orientation specifying unit performs rotation correction on the orientation of the body-insertable apparatus with respect to the specified reference direction with the orientation of the subject specified by the second orientation specifying unit.

6. The image processing system according to claim 1, wherein the body-insertable apparatus further includes a gravity direction detecting unit that detects a direction of gravity, the output unit adds the direction of gravity detected by the gravity direction detecting unit to the image data and outputs the resultant data to the outside, the input unit supplies the direction of gravity added to the image data to the first orientation specifying unit, and the first orientation specifying unit specifies orientation of the body-insertable apparatus from the direction of gravity supplied from the input unit.

7. The image processing system according to claim 1, wherein the average color bar generating unit calculates the average color in each of division regions obtained by dividing one piece of the image data, generates an image of the average color for each of the divided regions, and generates the average color bar so that images of the average color for corresponding division colors in the image data are arranged in parallel to a predetermined axis.

8. The image processing system according to claim 1, wherein the external device further includes a red detecting unit that detects a red component included in the image data subjected to the rotation correction; and a red image generating unit that generates a red image visually displaying a detection result of the red detecting unit, and the screen generating unit generates the screen in which the red image generated by the red image generating unit is incorporated.

9. The image processing system according to claim 8, wherein the organ image generating unit generates an organ image, as an image of an organ in the subject, obtained by superimposing images of the detection results generated by the red image generating unit, and the screen generating unit incorporates the organ image in the screen.

10. The image processing system according to claim 1, wherein the external device further includes a rotation amount image generating unit that generates a rotation amount image visually displaying a rotation amount used for the rotation correction for each of the image data, and the screen generating unit generates the screen in which the rotation amount image generated by the rotation amount image generating unit is incorporated.

11. The image processing system according to claim 1, wherein the external device further includes a position estimating unit that estimates position of the body-insertable apparatus at the time of obtaining the image data based on the rotation amount used for the rotation correction for each image data.

12. The image processing system according to claim 1, wherein the external device further includes a similarity determining unit that determines similarity of successive image data in a plurality of pieces of image data subjected to the rotation correction; and an image data selecting unit that selects image data subjected to the rotation correction, satisfying a predetermined condition from the plurality of pieces of image data subjected to the rotation correction based on a result of determination by the similarity determining unit.

13. The image processing system according to claim 1, wherein the external device further includes a motion vector calculating unit that calculates motion vectors of successive image data in the plurality of pieces of image data subjected to the rotation correction;

a maximum scalar quantity extracting unit that extracts a value at which a scalar quantity is maximum in the motion vectors calculated by the motion vector calculating unit; and an image data selecting unit that selects image data subjected to the rotation correction, satisfying a predetermined condition, from a plurality of pieces of image data subjected to the rotation correction based on a result of extraction by the maximum scalar quantity extracting unit.

14. The image processing system according to claim 1, wherein the screen generating unit generates a screen displaying a list of reduction images obtained by reducing the image data subjected to the rotation correction.

15. An external device comprising:
an input unit that receives image data obtained by a body-insertable apparatus including an imaging unit that captures inside of a subject;
an orientation specifying unit that specifies orientation of the body-insertable apparatus at the time of capturing the image data with respect to a reference direction;
a rotation correcting unit that performs rotation correction on image data which is received by the input unit based on the orientation specified by the orientation specifying unit, thereby aligning orientations of a plurality of pieces of image data;
a screen generating unit that generates a screen displaying the image data subjected to the rotation correction in the rotation correcting unit;
an average color bar generating unit that calculates an average color of the image data subjected to the rotation correction in the rotation correcting unit, generates an image of the calculated average color, and generates an average color bar in which images of the generated average colors are connected in accordance with order of the image data; and
an organ image generating unit that generates an organ image, as an image of an organ in the subject, obtained by superimposing the images of the average colors generated by the average color bar generating unit,
wherein the screen generating unit generates the screen in which the average color bar generated by the average color bar generating unit is incorporated, and incorporates the organ image generated by the organ image generating unit in the screen.

16. An image processing method comprising:
receiving image data obtained by a body-insertable apparatus including an imaging unit that captures inside of a subject;
specifying orientation of the body-insertable apparatus at the time of capturing the image data with respect to a reference direction;
performing rotation correction on the image data based on the specified orientation, thereby aligning orientations of a plurality of pieces of image data;
generating a screen displaying the image data subjected to the rotation correction;
calculating an average color of the image data subjected to the rotation correction, generating an image of the calculated average color, and generating an average color bar in which images of the generated average colors are connected in accordance with order of the image data; and
generating an organ image, as an image of an organ in the subject, obtained by superimposing the images of the average colors generated at the generating the average color bar,
wherein the generating the screen, includes generating the screen in which the generated average color bar is incorporated, and incorporating the generated organ image.

17. An image processing system comprising:
a body-insertable apparatus including an imaging means for capturing inside of a subject and an output means for outputting image data obtained by the imaging unit to the outside; and
an external device including
an input means for receiving the image data,
an orientation specifying means for specifying orientation of the body- insertable apparatus at the time of capturing the image data with respect to a reference direction,
a rotation correcting means for performing rotation correction on image data which is received by the input means based on the orientation specified by the orientation specifying means, thereby aligning orientations of a plurality of pieces of image data,
a screen generating means for generating a screen displaying the image data subjected to the rotation correction by the rotation correcting means,
an average color bar generating means for calculating an average color of the image data subjected to the rotation correction by the rotation correcting means, generating an image of the calculated average color, and generating an average color bar in which images of the generated average colors are connected in accordance with order of the image data, and
an organ image generating means for generating an organ image, as an image of an organ in the subject, obtained by superimposing the images of the average colors generated by the average color bar generating means,
wherein the screen generating means generates the screen in which the average color bar generated by the average color bar generating means is incorporated, and incorporates the organ image generated by the organ image generating means into the screen.

* * * * *